United States Patent
Glick et al.

(10) Patent No.: US 10,556,903 B2
(45) Date of Patent: Feb. 11, 2020

(54) NLRP3 MODULATORS

(71) Applicant: INNATE TUMOR IMMUNITY, INC., Princeton, NJ (US)

(72) Inventors: Gary D. Glick, Ann Arbor, MI (US);
Shomir Ghosh, Brookline, MA (US);
William R. Roush, Jupiter, FL (US);
Edward James Olhava, Newton, MA (US)

(73) Assignee: Innate Tumor Immunity, Inc., Princeton, NJ (US)

( * ) Notice: Subject to any disclaimer, the term of this patent is extended or adjusted under 35 U.S.C. 154(b) by 0 days.

(21) Appl. No.: 16/093,990

(22) PCT Filed: Apr. 19, 2017

(86) PCT No.: PCT/US2017/028384
§ 371 (c)(1),
(2) Date: Oct. 16, 2018

(87) PCT Pub. No.: WO2017/184746
PCT Pub. Date: Oct. 26, 2017

(65) Prior Publication Data
US 2019/0127367 A1    May 2, 2019

Related U.S. Application Data

(60) Provisional application No. 62/460,519, filed on Feb. 17, 2017, provisional application No. 62/324,626, filed on Apr. 19, 2016.

(51) Int. Cl.
| | | |
|---|---|---|
| *C07D 471/04* | (2006.01) | |
| *A61K 31/437* | (2006.01) | |
| *A61K 31/4709* | (2006.01) | |
| *A61K 31/506* | (2006.01) | |
| *A61K 31/5377* | (2006.01) | |
| *A61K 45/06* | (2006.01) | |

(52) U.S. Cl.
CPC .......... *C07D 471/04* (2013.01); *A61K 31/437* (2013.01); *A61K 31/4709* (2013.01); *A61K 31/506* (2013.01); *A61K 31/5377* (2013.01); *A61K 45/06* (2013.01)

(58) Field of Classification Search
CPC ............................ C07D 471/04; C07D 519/00
See application file for complete search history.

(56) References Cited

U.S. PATENT DOCUMENTS

| | | | |
|---|---|---|---|
| 5,389,640 A | 2/1995 | Gerster et al. | |
| 6,348,462 B1 | 2/2002 | Gerster et al. | |
| 7,091,214 B2 | 8/2006 | Hays et al. | |
| 7,598,382 B2 | 10/2009 | Hays et al. | |
| 7,858,637 B2 | 12/2010 | Averett | |
| 8,017,779 B2 * | 9/2011 | Merrill ................. | C07D 471/14 546/82 |
| 8,728,486 B2 | 5/2014 | David et al. | |
| 9,295,732 B2 | 3/2016 | Lioux et al. | |
| 2007/0259881 A1 | 11/2007 | Dellaria, Jr. et al. | |
| 2009/0069314 A1* | 3/2009 | Kshirsagar .......... | C07D 471/04 514/232.8 |
| 2017/0217960 A1 | 8/2017 | Ferguson | |

FOREIGN PATENT DOCUMENTS

| | | |
|---|---|---|
| EP | 0 145 340 A2 | 6/1985 |
| EP | 2 674 170 A1 | 12/2018 |
| JP | 11-80156 A | 4/1997 |
| WO | WO1993/05042 A1 | 3/1993 |
| WO | WO2002/24225 A1 | 3/2002 |
| WO | WO2004/058759 A1 | 7/2004 |
| WO | WO2005/018555 A2 | 3/2005 |
| WO | WO2005/020999 A1 | 3/2005 |
| WO | WO2005/025583 A2 | 3/2005 |
| WO | WO2005/051317 A2 | 6/2005 |
| WO | WO2005/076783 A2 | 8/2005 |
| WO | WO2005/123079 A2 | 12/2005 |
| WO | WO2005/123080 A2 | 12/2005 |
| WO | WO2006/009832 A1 | 1/2006 |
| WO | WO2006/031878 A2 | 3/2006 |
| WO | WO2006/065280 A2 | 6/2006 |

(Continued)

OTHER PUBLICATIONS

U.S. Appl. No. 15/898,258, filed Feb. 16, 2018, Glick, et al.

(Continued)

*Primary Examiner* — Valerie Rodriguez-Garcia
(74) *Attorney, Agent, or Firm* — Jing G. Sun

(57) ABSTRACT

This disclosure features compounds of Formula I, or a pharmaceutically acceptable salt thereof:

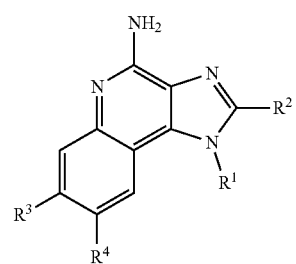

in which $R^1$, $R^2$, $R^3$, and $R^4$ are as defined herein. These compounds are modulators of NLRP3, which are useful, e.g., for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human). This disclosure also features compositions as well as other methods of using and making the same.

5 Claims, No Drawings

(56) References Cited

FOREIGN PATENT DOCUMENTS

| WO | WO2006/073940 A2 | 7/2006 |
|---|---|---|
| WO | WO2006/091394 A2 | 8/2006 |
| WO | WO2006/091567 A2 | 8/2006 |
| WO | WO2006/098852 A2 | 9/2006 |
| WO | WO2007/079086 A1 | 7/2007 |
| WO | WO2010/088924 A1 | 8/2010 |
| WO | WO2013/033345 A1 | 3/2013 |
| WO | WO2015/095780 A1 | 6/2015 |
| WO | WO2016/004875 A1 | 1/2016 |
| WO | WO2016/034085 A1 | 3/2016 |
| WO | WO2016/055812 A1 | 4/2016 |
| WO | WO2017/040670 A1 | 3/2017 |

OTHER PUBLICATIONS

U.S. Appl. No. 16/094,000, filed Oct. 16, 2018, Glick, et al.

Baldwin, Alex G. et al., "Inhibiting the Inflammasome: A Chemical Perspective", Journal of Medicinal Chemistry, vol. 59, pp. 1691-1710 (2016).

Bauernfeind, F. et al., "Of inflammasomes and pathogens—sensing of microbes by the inflammasome", EMBO Molecular Medicine, vol. 5, pp. 814-826 (2013).

Chaput, Catherine et al., "NOD-like receptors in lung diseases" Frontiers in Immunology, vol. 4, Article 393 pp. 1-12 (2013).

Chen, Lih-Chyang et al., "Tumour inflammasome-derived IL-1β recruits neutrophils and improves local recurrence-free survival in EBV-induced nasopharyngeal carcinoma", EMBO Molecular Medicine, vol. 4, pp. 1276-1293 (2012).

Fuertes, Mercedes B. et al., "Type I interferon response and innate immune sensing of cancer", Trends in Immunology, vol. 34(2), pp. 67-73 (2013).

Gerster, John F. et al., "Synthesis and Structure—Activity-Relationships of 1H-Imidazo[4,5-c]quinolones That Induce Interferon Production", J. Med Chemistry, vol. 48, pp. 3481-3491 (2005).

Hirota, Jeremy A. et al., "The airway epithelium nucleotide-binding domain and leucine-rich repeat protein 3 inflammasome is activated by urban particulate matter", J. Allergy Clinical Immunology, vol. 129, pp. 1116-1125 (2012).

Lin, Chu et al., "Inflammasomes in Inflammation-Induced Cancer", Frontiers in Immunology, vol. 8, Article 271, pp. 1-22 (2017).

Ma, Zhifeng et al., "Augmentation of Immune Checkpoint Cancer Immunotherapy with IL18" Clinical Cancer Research, vol. 22(12), pp. 2969-2980 (2016).

Ting, Jenny P.Y. et al., "The NLR Gene Family: A Standard Nomenclature", Immunity, vol. 28, pp. 285-287 (2008).

Tse, Brian Wan-Chi et al., "IL-18 Inhibits Growth of Murine Orthotopic Prostate Carcinomas via Both Adaptive and Innate Immune Mechanisms", PLOS One, vol. 6(9), pp. 1-12 (2011).

CAS Registry No. 1027225-83-7 entered Jun. 11, 2008.

\* cited by examiner

NLRP3 MODULATORS

This application is a 371 of International Application No. PCT/US2017/028384 filed on Apr. 19, 2017, which claims the benefit of priority of U.S. Provisional Application 62/324,626, filed Apr. 19, 2016 and U.S. Provisional Application 62/460,519, filed Feb. 17, 2017, each of which is incorporated herein by reference in its entirety.

TECHNICAL FIELD

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human). This disclosure also features compositions as well as other methods of using and making the same.

BACKGROUND

Nucleotide-binding oligomerization domain-like receptors ("NLRs") include a family of intracellular receptors that detects pathogen-associated molecular patterns ("PAMPs") and endogenous molecules (see, e.g., P.-Y. Ting, et al., "The NLR gene family: a standard nomenclature," *Immunity*, vol. 28, no. 3, pp. 285-287, 2008).

NLRPs represent a subfamily of NLRs that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., C. Chaput, et al., "NOD-like receptors in lung diseases," *Frontiers in Immunology*, vol. 4, article 393, 2013). These complexes typically include one or two NLR proteins, the adapter molecule apoptosis associated speck-like containing a CARD domain (ASC) and pro-caspase-1 F (see, e.g., Bauernfeind and V. Hornung, "Of inflammasomes and pathogens—sensing of microbes by the inflammasome," *EMBO Molecular Medicine*, vol. 5, no. 6, pp. 814-826, 2013).

One such inflammasome is formed by the NLRP3 scaffold, the ASC adaptor and caspase-1 (see, e.g., J. A. Hirota, et al., "The airway epithelium nucleotide-binding domain and leucine-rich repeat protein 3 inflammasome is activated by urban particulate matter," *Journal of Allergy and Clinical Immunology*, vol. 129, no. 4, pp. 1116.e6-1125.e6, 2012), and its expression is believed to be induced by inflammatory cytokines and TLR agonists in myeloid cells and human bronchial epithelial cells (Id). The NLRP3 inflammasome is believed to mediate the caspase-1-dependent conversion of pro-IL-1β and pro-IL-18 to IL-1β and IL-18. Further, IL-1β and IL-18 have been shown to play an important role in the treatment of various types of cancer (see, e.g., *EMBO Mol Med.* 2012 4:1276 and *PLoS One* 2011 6:e24241). IL-18 has been shown to override resistance to checkpoint inhibitors in colon cancer tumor models (see *Clin. Cancer Res.* 2016 Jan. 11. pii: clincanres.1655.2015).

SUMMARY

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human). This disclosure also features compositions as well as other methods of using and making the same.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In one aspect, compounds of Formula I, or a pharmaceutically acceptable salt thereof, are featured:

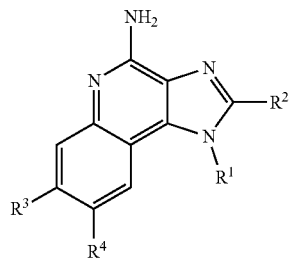

in which $R^1$, $R^2$, $R^3$, and $R^4$ can be as defined anywhere herein.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which repressed or impaired NLRP3 signaling contributes to the pathology and/or symptoms and/or progression of the disease (e.g., cancer, e.g., a refractory cancer).

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment of a disease in which repressed or impaired NLRP3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which repressed or impaired NLRP3 signaling contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment that include administering to a subject a chemical entity described herein (e.g., a compound described generically or specifically herein or a pharmaceutically acceptable salt thereof or compositions containing the same), wherein the chemical entity is administered in an amount effective to treat a disease in which repressed or impaired NLRP3 signaling contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof; e.g., chemotherapy that includes administering one or more (e.g., two, three, four, five, six, or more) additional chemotherapeutic agents. Non-limiting examples of additional chemotherapeutic agents is selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine Taxol, Paclltaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from the group consisting of CTLA-4, PD-1, PD-L1, PD-1—PD-L1, PD-1—PD-L2, T cell immunoglobulin and mucin 3 (TIM3 or HAVCR2), Galectin 9—TIM3, Phosphatidylserine—TIM3, lymphocyte activation gene 3 protein (LAG3), MHC class II—LAG3, 4-IBB-4-IBB ligand, OX40-OX40 ligand, GITR, GITR ligand—GITR, CD27, CD70-CD27, TNFRSF25, TNFRSF25-TL A, CD40L, CD40-CD40 ligand, HVEM-LIGHT-LTA, HVEM, HVEM—BTLA, HVEM—CD160, HVEM—LIGHT, HVEM-BTLA-CD160, CD80, CD80—PDL-1, PDL2—CD80, CD244, CD48—CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86—CD28, CD86—CTLA, CD80—CD28, Phosphatidylserine, TIM3, Phosphatidylserine—TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-$\beta$ (TGF$\beta$), CD39, CD73 Adenosine-CD39-CD73, and CXCR4-CXCL12.

The subject can have cancer; e.g., the subject has undergone and/or is undergoing and/or will undergo one or more cancer therapies.

Non-limiting examples of cancer include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In other embodiments, the mammal has been identified as having a cancer or an infectious disease. Representative infectious diseases include, without limitation, *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, *Burkholderi* infection, Buruli ulcer, *Calicivirus* infection, camptobacteriosis, candidiasis, cat-scratch disease, cellulitis, Chagas disease, chancroid, chickenpox, chikungunya, chlamydia, *Chlamy-* dophila pneumoniae infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, *Desmodesmus* infection, deintamoebiasis, diphtheria, diphyllobothriasis, dracunculiasis, ebola hemorrhagic fever, echinococcosis, ehrlichiosis, enterobiasis, *Enterococcus* infection, *Enterovirus* infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, a variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, staphylococcal infection, strongyloidiasis, subacute sclerosing panencephalitis, syphilis, taeniasis, tetanus, tinea barbae, tinea capitis, tinea corporis, tinea cruris, tinea manum, tinea nigra, tinea pedis, tinea unguium, tinea versicolor, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

The chemical entity can be administered intratumorally.
The chemical entity can be administered systemically.
The methods can further include identifying the subject.
Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed; Rowe et al., Eds.; The Pharmaceutical Press and the American Pharmaceutical Association: 2009; *Handbook of Pharmaceutical Additives*, 3rd ed; Ash and Ash Eds.; Gower Publishing Company: 2007; *Pharmaceutical Preformulation and Formulation*, 2nd ed; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, a citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a branched or unbranched divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, so wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkylene" as used herein refers to divalent cycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocycloalkylene" refers to divalent heterocyclyl.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human). This disclosure also features compositions as well as other methods of using and making the same.

Formula I Compounds

In one aspect, compounds of Formula I, or a pharmaceutically acceptable salt thereof are featured:

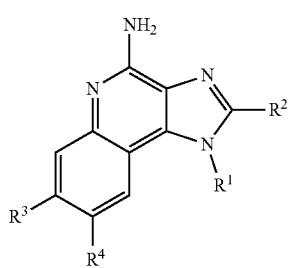

(I)

wherein:
$R^1$ is:
(i) hydrogen;
(ii) X—$R^5$, wherein X is an unbranched $C_{2-6}$ alkylene, and $R^5$ is hydrogen, —OH, $C_{1-4}$ alkoxy, —$C_{1-4}$ haloalkoxy, $CO_2R^a$; —$CONR^bR^c$, cyano, or —$NR^bR^c$;
(iii) ($C_{1-3}$ alkylene)aryl, wherein the aryl is optionally substituted with from 1-3 $R^d$; or
(iv) ($C_{1-3}$ alkylene)heteroaryl including from 5-6 ring atoms, wherein from 1-4 ring atoms are each independently selected from the group consisting of nitrogen, oxygen and sulfur, and wherein the heteroaryl is optionally substituted with from 1-3 $R^d$;

$R^2$ is:
(i) Y—$R^6$, wherein:
Y is $C_{2-8}$ alkylene, which is optionally substituted with from 1-4 $R^e$; and
$R^6$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur;
OR
(ii) —$(Y^1)_n$—$Y^2$—$(Y^3)_p$—$R^6$, wherein:
each of n and p is independently 0 or 1;
each of $Y^1$ and $Y^3$ is, independently, $C_{1-3}$ alkylene, which is optionally substituted with from 1-2 $R^e$,
$Y^2$ is $C_{3-6}$ cycloalkylene or heterocycloalkylene including from 3-8 ring atoms, wherein from 1-2 ring atoms are each independently selected from the group consisting of N, N($R^f$) and oxygen, and wherein $Y^2$ is optionally further substituted with from 1-4 $R^g$, and
$R^6$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur;
OR
(iii) —$Z^1$—$Z^2$—$Z^3$—$R^7$, wherein:
$Z^1$ is $C_{1-3}$ alkylene, which is optionally substituted with from 1-6 F,
$Z^2$ is —N($R^f$)—, —O—, or —S—;
$Z^3$ is $C_{2-5}$ alkylene, which is optionally substituted with from 1-6 F, and
$R^7$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur;

$R^3$ and $R^4$ are each independently selected from the group consisting of:
(i) hydrogen;
(ii) halo;
(iii) cyano;
(iv) $CO_2R^a$;
(v) $CONR^bR^c$;
(vi) $C_{1-4}$ alkyl;
(vii) $C_{1-4}$ haloalkyl;
(viii) $C_{1-4}$ alkoxy; and
(ix) $C_{1-4}$ haloalkoxy;

$R^a$ is:
(i) H;
(ii) $C_{1-6}$ alkyl optionally substituted with from 1-2 substituents independently selected from —OH, —$NH_2$, —NH($C_{1-3}$ alkyl), —N($C_{1-3}$ alkyl)$_2$, —N(H)(C(=O)$C_{1-3}$ alkyl), or cyano;
(iii) $C_{3-6}$ cycloalkyl optionally substituted with from 1-4 substituents independently selected from $C_{1-6}$ alkyl, $C_{1-4}$ haloalkyl, F, Cl, Br, —OH, $C_{1-4}$ alkoxy, and $C_{1-4}$ haloalkoxy; or
(iv) benzyl, wherein the phenyl portion is optionally substituted with from 1-4 substituents independently selected from $C_{1-6}$ alkyl, $C_{1-4}$ haloalkyl, F, Cl, Br, —OH, $C_{1-4}$ alkoxy, $C_{1-4}$ haloalkoxy, cyano, $CO_2(C_{1-6}$ alkyl); —$CONR^jR^k$, and —$NR^jR^k$;

each occurrence of $R^b$ and $R^c$ is independently selected from the group consisting of: H, $C_{1-4}$ alkyl, —C(O)($C_{1-4}$ alkyl), —C(O)O($C_{1-4}$ alkyl), —S(O)$_{1-2}$($R^h$), —C(O)$NR^jR^k$, —OH, and $C_{1-4}$ alkoxy; or $R^b$ and $R^c$, together with the nitrogen atom to which each is attached forms heterocyclyl including from 3-10 ring atoms, wherein from 1-3 ring atoms are each independently selected from the group consisting of N(R$^f$), O, and S, and wherein the heterocyclyl is optionally further substituted with from 1-4 R$^g$, each occurrence of R$^d$ is independently selected from the group consisting of:
(i) halo;
(ii) cyano;
(iii) C$_{1-4}$ alkyl optionally substituted with from 1-2 substituents independently selected from —OH, C$_{1-4}$ alkoxy, C$_{1-4}$ haloalkoxy, —CO$_2$R$^a$; —CONR$^b$R$^c$, cyano, and —NR$^b$R$^c$;
(iv) C$_{2-6}$ alkenyl;
(v) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl including from 3-10 ring atoms, wherein from 1-3 ring atoms are each independently selected from the group consisting of nitrogen, oxygen and sulfur, wherein the heterocyclyl is optionally substituted with from 1-4 independently selected C$_{1-4}$ alkyl;
(xi) —(C$_{0-3}$ alkylene)-phenyl optionally substituted with from 1-3 R$^m$;
(xii) —(C$_{0-3}$ alkylene)-heteroaryl including from 3-10 ring atoms, wherein from 1-3 ring atoms are each independently selected from the group consisting of nitrogen, oxygen and sulfur, wherein the heteroaryl is optionally substituted with from 1-3 R$^m$;
(xiii) —S(O)$_{1-2}$(R$^h$); and
(xiv) —NR$^b$R$^c$;

each occurrence of R$^e$ is independently selected from the group consisting of: F, —OH, C$_{1-4}$ alkoxy, C$_{1-4}$ haloalkoxy, CO$_2$R$^a$; —OC(O)R$^h$, —CONR$^b$R$^c$, and —NR$^b$R$^c$;

each occurrence of R$^f$ is independently selected from the group consisting of: H, C$_{1-4}$ alkyl, —C(O)(C$_{1-4}$ alkyl), —C(O)O(C$_{1-4}$ alkyl), —C(O)NR$^j$R$^k$, —S(O)$_{1-2}$R$^h$, —OH, and C$_{1-4}$ alkoxy;

each occurrence of R$^g$ is independently selected from the group consisting of: C$_{1-6}$ alkyl, C$_{1-4}$ haloalkyl, F, —OH, C$_{1-4}$ alkoxy, C$_{1-4}$ haloalkoxy, CO$_2$R$^a$; —CONR$^j$R$^k$, and —NR$^j$R$^k$;

each occurrence of R$^h$ is independently selected from the group consisting of: C$_{1-6}$ alkyl, C$_{1-4}$ haloalkyl, C$_{1-4}$ alkoxy, C$_{1-4}$ haloalkoxy, phenyl optionally substituted with from 1-3 R$^m$, and heteroaryl including from 3-10 ring atoms, wherein from 1-3 ring atoms are each independently selected from the group consisting of nitrogen, oxygen and sulfur, wherein the heteroaryl is optionally substituted with from 1-3 R$^m$;

each occurrence of R$^j$ and R$^k$ is independently selected from the group consisting of: H and C$_{1-4}$ alkyl; and each occurrence of R$^m$ is independently selected from the group consisting of: C$_{1-6}$ alkyl, C$_{1-4}$ haloalkyl, F, Cl, Br, —OH, C$_{1-4}$ alkoxy, C$_{1-4}$ haloalkoxy, cyano, CO$_2$R$^a$; —CONR$^j$R$^k$, and —NR$^j$R$^k$.

In another aspect, compounds of Formula I, or a pharmaceutically acceptable salt thereof are featured:

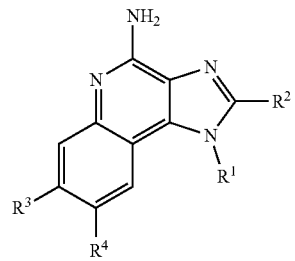

(I)

wherein:
R$^1$ is:
(i) H
(ii) X—R$^5$, wherein X is an unbranched C$_{1-6}$ alkylene, and R$^5$ is hydrogen, —OH, C$_{1-4}$ alkoxy, —C$_{1-4}$ haloalkoxy, CO$_2$R$^a$, —CONR$^b$R$^c$; cyano, or —NR$^b$R$^c$;
(iii) (C$_{1-3}$ alkylene)aryl, wherein the aryl is optionally substituted with from 1-3 R$^d$; or
(iv) (C$_{1-3}$ alkylene)heteroaryl including from 5-6 ring atoms, wherein from 1-4 ring atoms are each independently selected from the group consisting of nitrogen, oxygen and sulfur, and wherein the heteroaryl is optionally substituted with from 1-3 R$^d$;

R$^2$ is:
(i) Y—R$^6$, wherein:
Y is C$_{2-8}$ alkylene, which is optionally substituted with from 1-4 R$^e$; and
R$^6$ is —OH, CO$_2$R$^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur;
OR
(ii) —(Y$^1$)$^n$—Y$^2$—(Y$^3$)$_p$—R$^{6'}$, wherein:
each of n and p is independently 0 or 1;
each of Y$^1$ and Y$^3$ is, independently, C$_{1-3}$ alkylene, which is optionally substituted with from 1-2 R$^e$,
Y$^2$ is C$_{3-6}$ cycloalkylene or heterocycloalkylene including from 3-8 ring atoms, wherein from 1-2 ring atoms are each independently selected from the group consisting of N, N(R$^f$) and oxygen, and wherein Y$^2$ is optionally further substituted with from 1-4 R$^g$, and
R$^{6'}$ is H, —OH, CO$_2$R$^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur, wherein R$^{6'}$ cannot be H when Y$^2$ is C$_{3-6}$ cycloalkylene optionally substituted with from 1-4 R$^g$;
OR
(iii) —Z$^1$—Z$^2$—Z$^3$—R$^7$, wherein:
Z$^1$ is C$_{1-3}$ alkylene, which is optionally substituted with from 1-6 F,
Z$^2$ is —N(R$^f$)—, —O—, or —S—;
Z$^3$ is C$_{2-85}$ alkylene, which is optionally substituted with from 1-6 F, and
R$^7$ is —OH, CO$_2$R$^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur;

R$^3$ and R$^4$ are each independently selected from the group consisting of:
(i) hydrogen;
(ii) halo;
(iii) cyano;
(iv) CO$_2$R$^a$;

(v) CONR$^b$R$^c$;
(vi) C$_{1-4}$ alkyl, optionally substituted with from 1-2 substituents independently selected from —OH, C$_{1-4}$ alkoxy, C$_{1-4}$ haloalkoxy, —CO$_2$R$^a$; —CONR$^b$R$^c$, cyano, and —NR$^b$R$^c$;
(vii) C$_{1-4}$ haloalkyl;
(viii) C$_{1-4}$ alkoxy;
(ix) C$_{1-4}$ haloalkoxy;
(x) —(C$_{1-3}$ alkylene)$_y$-C$_{5-8}$ cycloalkyl, wherein the cycloalkyl is optionally substituted with from 1-4 independently selected R$^g$, wherein y is 0 or 1;
(xi) —(C$_{1-3}$ alkylene)$_y$-heterocyclyl including from 5-8 ring atoms, wherein from 1-3 ring atoms are each independently selected from the group consisting of N(R$^f$), O, and S, wherein the heterocyclyl is optionally substituted with from 1-4 substituents independently selected from oxo and R$^g$, wherein y is 0 or 1;
(xii) —(C$_{1-3}$ alkylene)$_y$-phenyl optionally substituted with from 1-4 R$^d$, wherein y is 0 or 1;
(xiii) —(C$_{1-3}$ alkylene)$_y$-heteroaryl including from 5-10 ring atoms, wherein from 1-4 ring atoms are each independently selected from the group consisting of N, N(R$^f$), O, and S, wherein the heteroaryl is optionally substituted with from 1-3 R$^d$, wherein y is 0 or 1;
(xiv) —Y—(C$_6$-C$_{10}$ aryl) optionally substituted with from 1-4 R$^d$, wherein Y is 0 or S;
(xv) —Y-heteroaryl including from 5-10 ring atoms, wherein from 1-3 ring atoms are each independently selected from the group consisting of N, N(R$^f$), O, and S, wherein the heteroaryl is optionally substituted with from 1-3 R$^d$, wherein Y is O or S;
(xvi) —SO$_2$(C$_{1-6}$ alkyl); and
(xvii) —NR$^b$R$^c$;
R$^a$ is:
(i) H;
(ii) C$_{1-6}$ alkyl optionally substituted with from 1-2 substituents independently selected from —OH, —NR$^j$R$^k$; —N(H)(C(=O)C$_{1-4}$ alkyl), —N(H)(C(=O)OC$_{1-4}$ alkyl), —CO$_2$(C$_{1-6}$ alkyl); —CONR$^j$R$^k$, or cyano;
(iii) C$_{3-6}$ cycloalkyl optionally substituted with from 1-4 substituents independently selected from C$_{1-4}$ alkyl, C$_{1-4}$ haloalkyl, F, Cl, Br, —NR$^j$R$^k$; —N(H)(C(=O)C$_{1-4}$ alkyl), —N(H)(C(=O)OC$_{1-4}$ alkyl), —CO$_2$(C$_{1-4}$ alkyl); —CONR$^j$R$^k$, —OH, C$_{1-4}$ alkoxy, and C$_{1-4}$ haloalkoxy; or
(iv) benzyl, wherein the phenyl portion is optionally substituted with from 1-4 substituents independently selected from C$_{1-6}$ alkyl, C$_{1-4}$ haloalkyl, F, Cl, Br, —OH, C$_{1-4}$ alkoxy, C$_{1-4}$ haloalkoxy, —N(H)(C(=O)C$_{1-4}$ alkyl), —N(H)(C(=O)OC$_{1-4}$ alkyl), cyano, —CO$_2$(C$_{1-6}$ alkyl); —CONR$^j$R$^k$, and —NR$^j$R$^k$;
(v) C$_{6-10}$ aryl optionally substituted with from 1-3 R$^m$;
(vi) heteroaryl including from 5-10 ring atoms, wherein from 1-3 ring atoms are each independently selected from the group consisting of nitrogen, oxygen and sulfur, wherein so the heteroaryl is optionally substituted with from 1-3 R$^m$;
each occurrence of R$^b$ and R$^c$ is independently selected from the group consisting of: R$^a$; —C(O)(R$^a$), —C(O)O(R$^a$), —S(O)$_{1-2}$(R$^h$), and —C(O)NR$^j$R$^k$; or R$^b$ and R$^c$, together with the nitrogen atom to which each is attached forms heterocyclyl including from 3-10 ring atoms, wherein from 1-3 ring atoms are each independently selected from the group consisting of N(R$^f$), O, and S, and wherein the heterocyclyl is optionally further substituted with from 1-4 R$^g$,
each occurrence of R$^d$ is independently selected from the group consisting of:

(i) halo;
(ii) cyano;
(iii) C$_{1-6}$ alkyl optionally substituted with from 1-2 substituents independently selected from —OH, C$_{1-4}$ alkoxy, C$_{1-4}$ haloalkoxy, —CO$_2$R$^a$; —CONR$^b$R$^c$, cyano, and —NR$^b$R$^c$;
(iv) C$_{2-6}$ alkenyl;
(v) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl including from 3-10 ring atoms, wherein from 1-3 ring atoms are each independently selected from the group consisting of nitrogen, oxygen and sulfur, wherein the heterocyclyl is optionally substituted with from 1-4 independently selected C$_{1-4}$ alkyl;
(xi) —(C$_{0-3}$ alkylene)-phenyl optionally substituted with from 1-3 R$^m$;
(xii) —(C$_{0-3}$ alkylene)-heteroaryl including from 3-10 ring atoms, wherein from 1-3 ring atoms are each independently selected from the group consisting of nitrogen, oxygen and sulfur, wherein the heteroaryl is optionally substituted with from 1-3 R$^m$;
(xiii) —S(O)$_{1-2}$(R$^h$); and
(xiv) —NR$^b$R$^c$;
(xv) —OH;
(xvi) —S(O)$_{1-2}$(NR$^b$R$^c$); and
(xvii) —C$_{1-4}$ thioalkoxy;
each occurrence of R$^e$ is independently selected from the group consisting of: F, —OH, C$_{1-4}$ alkoxy, C$_{1-4}$ haloalkoxy, CO$_2$R$^a$; —OC(O)R$^h$, —CONR$^b$R$^c$, and —NR$^b$R$^c$;
each occurrence of R$^f$ is independently selected from the group consisting of: H, C$_{1-4}$ alkyl, —C(O)(C$_{1-4}$ alkyl), —C(O)O(C$_{1-4}$ alkyl), —C(O)NR$^j$R$^k$, —S(O)$_{1-2}$R$^h$, —OH, and C$_{1-4}$ alkoxy;
each occurrence of R$^g$ is independently selected from the group consisting of: C$_{1-6}$ alkyl, C$_{1-4}$ haloalkyl, F, —OH, C$_{1-4}$ alkoxy, C$_{1-4}$ haloalkoxy, CO$_2$R$^a$; —CONR$^j$R$^k$, and —NR$^j$R$^k$;
each occurrence of R$^h$ is independently selected from the group consisting of: C$_{1-6}$ alkyl, C$_{1-4}$ haloalkyl, C$_{1-4}$ alkoxy, C$_{1-4}$ haloalkoxy, phenyl optionally substituted with from 1-3 R$^m$, and heteroaryl including from 3-10 ring atoms, wherein from 1-3 ring atoms are each independently selected from the group consisting of nitrogen, oxygen and sulfur, wherein the heteroaryl is optionally substituted with from 1-3 R$^m$;
each occurrence of R$^j$ and R$^k$ is independently selected from the group consisting of: H and C$_{1-4}$ alkyl;
each occurrence of R$^m$ is independently selected from the group consisting of: C$_{1-6}$ alkyl, C$_{1-4}$ haloalkyl, F, Cl, Br, —OH, C$_{1-4}$ alkoxy, C$_{1-4}$ haloalkoxy, cyano, CO$_2$R$^a$; —CONR$^j$R$^k$, and —NR$^j$R$^k$; and
(i) provided when Y$^1$ is CH$_2$, then R$^1$ cannot be (C$_{1-3}$ alkylene)heteroaryl including 5 ring atoms, wherein from 1-4 ring atoms are each independently selected from the group consisting of nitrogen, oxygen and sulfur, and wherein the heteroaryl is optionally substituted with from 1-3 R$^d$.

In some embodiments, it is provided that one of R$^3$ and R$^4$ is other than hydrogen.

Variable R$^2$

—Y—R$^6$

In some embodiments, R$^2$ is Y—R$^6$, wherein:
Y is C$_{2-8}$ alkylene, which is optionally substituted with from 1-4 R$^e$; and
R$^6$ is —OH, CO$_2$R$^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur.

In some embodiments, Y is unbranched $C_{2-6}$ (e.g., $C_{2-4}$, $C_{2-3}$, $C_2$) alkylene, which is optionally substituted with from 1-4 (e.g., 1-2, 1) $R^e$. In certain embodiments, Y is unbranched $C_{2-6}$ (e.g., $C_{2-4}$, $C_{2-3}$, $C_2$) alkylene, which is unsubstituted (e.g., $C_2$ alkylene or $C_3$ alkylene; e.g., $C_3$ alkylene).

In other embodiments, Y is branched $C_{3-6}$ (e.g., $C_{4-6}$, $C_{5-6}$) alkylene, which is optionally substituted with from 1-4 (e.g., 1-2, 1) $R^e$. In certain embodiments, Y has the formula, R—CH(CH$_3$)—R$^6$, in which R is $C_{1-4}$ alkylene. In certain embodiments, Y is a branched $C_{2-3}$ alkylene. In certain embodiments, Y is a $C_2$ alkylene with the formula —CH(CH$_3$)—. In certain embodiments, Y is a $C_3$ alkylene with the formula —C(CH$_3$)$_2$—.

In some embodiments, $R^6$ is —OH, CO$_2$R$^a$;—or —NR$^b$R$^c$.

In certain embodiments, $R^6$ is —NR$^b$R$^c$.

In certain of these embodiments, each occurrence of $R^b$ and $R^c$ is independently selected from the group consisting of: H, $C_{1-4}$ alkyl, —C(O)(C$_{1-4}$ alkyl), —C(O)O(C$_{1-4}$ alkyl), —S(O)$_{1-2}$(R$^h$), —C(O)NR$^j$R$^k$, —OH, and $C_{1-4}$ alkoxy.

In certain of these embodiments, each occurrence of $R^b$ and $R^c$ is independently selected from the group consisting of: H, $C_{1-4}$ alkyl, —C(O)(C$_{1-4}$ alkyl), —C(O)O(C$_{1-4}$ alkyl), —S(O)$_{1-2}$(R$^h$), and —C(O)NR$^j$R$^k$.

In certain of these embodiments, each occurrence of $R^b$ and $R^c$ is independently selected from the group consisting of: H, $C_{1-4}$ alkyl, and —C(O)(C$_{1-4}$ alkyl).

In certain of these embodiments, each occurrence of $R^b$ and $R^c$ is independently selected from the group consisting of: H and $C_{1-4}$ alkyl. For example, $R^6$ can be —NH$_2$, —N(H)(C$_{1-4}$ alkyl) (e.g., —NHCH$_3$) or —N(C$_{1-4}$ alkyl)$_2$ (e.g., —N(CH$_3$)$_2$).

In certain of these embodiments, each occurrence of $R^b$ and $R^c$ is independently selected from the group consisting of: H and —C(O)(C$_{1-4}$ alkyl). For example, one of $R^b$ and $R^c$ is H, and the other is —C(O)(C$_{1-4}$ alkyl) (e.g., —C(O)(CH$_3$).

In certain of these embodiments, each occurrence of $R^b$ and $R^c$ is independently selected from the group consisting of: $C_{1-4}$ alkyl and —C(O)(C$_{1-4}$ alkyl). For example, one of $R^b$ and $R^c$ is $C_{1-4}$ alkyl (e.g., CH$_3$), and the other is —C(O)(C$_{1-4}$ alkyl) (e.g., —C(O)(CH$_3$).

In certain embodiments, $R^6$ is CO$_2$R$^a$.

In certain of these embodiments, $R^a$ is $C_{1-6}$ alkyl optionally substituted with —OH, —NH$_2$, —NH(C$_{1-3}$ alkyl), —N(C$_{1-3}$ alkyl)$_2$, —N(H)(C(=O)C$_{1-3}$ alkyl), or cyano.

In certain of these embodiments, $R^a$ is unsubstituted $C_{1-6}$ alkyl (e.g., CH$_3$ or CH$_2$CH$_3$).

In certain embodiments, $R^6$ is —OH (in certain embodiments, $R^2$ is —CH$_2$CH$_2$CH$_2$OH).

—(Y$^1$)$_n$—Y$^2$—(Y$^3$)$_p$—R$^{6'}$

In some embodiments, $R^2$ is —(Y$^1$)$_n$—Y$^2$—(Y$^3$)$_p$—R$^{6'}$, wherein:
  each of n and p is independently 0 or 1;
  each of Y$^1$ and Y$^3$ is, independently, $C_{1-3}$ alkylene, which is optionally substituted with from 1-2 R$^e$,
  Y$^2$ is $C_{3-6}$ cycloalkylene or heterocycloalkylene including from 3-8 ring atoms, wherein from 1-2 ring atoms are each independently selected from the group consisting of N, N(R$^f$) and oxygen, and wherein Y$^2$ is optionally further substituted with from 1-4 R$^g$, and
  R$^{6'}$ is —OH, CO$_2$R$^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur.

In some embodiments, $R^2$ is —(Y$^1$)$_n$—Y$^2$—(Y$^3$)$_p$—R$^{6'}$, wherein:
  each of n and p is independently 0 or 1;
  each of Y$^1$ and Y$^3$ is, independently, $C_{1-3}$ alkylene, which is optionally substituted with from 1-2 R$^e$,
  Y$^2$ is $C_{3-6}$ cycloalkylene or heterocycloalkylene including from 3-8 ring atoms, wherein from 1-2 ring atoms are each independently selected from the group consisting of N, N(R$^f$) and oxygen, and wherein Y$^2$ is optionally further substituted with from 1-4 R$^g$, and
  R$^{6'}$ is H, —OH, CO$_2$R$^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur, wherein R$^{6'}$ cannot be H when Y$^2$ is $C_{3-6}$ cycloalkylene optionally substituted with from 1-4 R$^g$;

In some embodiments, n is 0.

In some embodiments, n is 1. In certain of these embodiments, Y$^1$ is CH$_2$.

In some embodiments, Y$^2$ is $C_{3-6}$ (e.g., $C_{3-5}$, $C_{3-4}$) cycloalkylene optionally substituted with from 1-4 R$^g$. In certain embodiments, p is 0. In certain embodiments, p is 1; in certain of these embodiments, Y$^3$ is $C_{1-2}$ alkylene.

In some embodiments, Y$^2$ is heterocycloalkylene including from 3-8 (e.g., 5-8, 6-8, 7-8, 4-6, 5-6) ring atoms, wherein from 1-2 (e.g., 1) ring atoms are each independently selected from the group consisting of N, N(R$^f$), and oxygen, and wherein Y$^2$ is optionally further substituted with from 1-4 R$^g$.

In some embodiments, Y$^2$ is heterocycloalkylene including from 3-6 (e.g., 4-6, 5-so 6) ring atoms, wherein from 1-2 (e.g., 1) ring atoms are each independently selected from the group consisting of N, N(R$^f$), and oxygen, and wherein Y$^2$ is optionally further substituted with from 1-4 R$^g$.

In certain embodiments, Y$^2$ is heterocycloalkylene including from 3-6 (e.g., 4-6, 5-6) ring atoms, wherein from 1-2 ring atoms are each independently selected from the group consisting of N and N(R$^f$), and wherein Y$^2$ is optionally further substituted with from 1-4 R$^g$.

In certain embodiments, Y$^2$ is heterocycloalkylene including from 3-6 (e.g., 4-6, 5-6) ring atoms, wherein 1 ring atom is N(R$^f$), and wherein Y$^2$ is optionally further substituted with from 1-4 R$^g$.

In certain embodiments, Y$^2$ is heterocycloalkylene including from 3-6 (e.g., 4-6, 5-6) ring atoms, wherein 1 ring atom is N, and wherein Y$^2$ is optionally further substituted with from 1-4 R$^g$. In certain of these embodiments, the ring atom N is attached to Y$^1$, when present, or the imidazole ring of formula (I). In other of these embodiments, the ring atom N is attached to Y$^3$, when present, or R$^6$. In certain embodiments, p is 0. In certain embodiments, p is 1; in certain of these embodiments, Y$^3$ is $C_{2-3}$ alkylene. In still other embodiments, the ring atom N is attached to the imidazole ring of formula (I). In still other embodiments, the ring atom N is attached to R$^6$. In another embodiment, n is 0, p is 0, and the ring atom N is attached to R$^6$.

In some —(Y$^1$)$_n$—Y$^2$—(Y$^3$)$_p$—R$^{6'}$ embodiments, R$^{6'}$ can be as defined above in conjunction with variable Y. In certain embodiments, R$^{6'}$ can be H.

—Z$^1$—Z$^2$—Z$^3$—R$^7$

In some embodiments, $R^2$ is —Z$^1$—Z$^2$—Z$^3$—R$^7$, wherein:
  Z$^1$ is unbranched or branched $C_{1-3}$ alkylene, which is optionally substituted with from 1-6 F,
  Z$^2$ is —N(R$^f$)—, —O—, or —S—;
  Z$^3$ is unbranched or branched $C_{2-5}$ alkylene, which is optionally substituted with from 1-6 F, and $R^7$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur;

In some embodiments, $Z^1$ is $CH_2$.

In some embodiments, $Z^2$ is —O—, or —S— (e.g., —O—).

In some embodiments, $Z^2$ is —N($R^f$)—. For example, $Z^2$ can be —NH—, —N($C_{1-4}$ alkyl)-, or —NC(O)($C_{1-4}$ alkyl)- (e.g., —NC(O)($CH_3$)—).

In some embodiments, $Z^3$ is $C_{2-3}$ alkylene.

In some embodiments, $R^7$ is —OH, $CO_2R^a$;—or —$NR^bR^c$.

In certain embodiments, $R^7$ is —$NR^bR^c$.

In certain of these embodiments, each occurrence of $R^b$ and $R^c$ is independently selected from the group consisting of: H, $C_{1-4}$ alkyl, —C(O)($C_{1-4}$ alkyl), —C(O)O($C_{1-4}$ alkyl), —S(O)$_{1-2}$($R^h$), —C(O)$NR^jR^k$, —OH, and $C_{1-4}$ alkoxy.

In certain of these embodiments, each occurrence of $R^b$ and $R^c$ is independently selected from the group consisting of: H, $C_{1-4}$ alkyl, —C(O)($C_4$ alkyl), —C(O)O($C_{1-4}$ alkyl), —S(O)$_{1-2}$($R^h$), and —C(O)$NR^jR^k$.

In certain of these embodiments, each occurrence of $R^b$ and $R^c$ is independently selected from the group consisting of: H, $C_{1-4}$ alkyl, and —C(O)($C_{1-4}$ alkyl).

In certain of these embodiments, each occurrence of $R^b$ and $R^c$ is independently selected from the group consisting of: H and $C_{1-4}$ alkyl. For example, $R^6$ can be —$NH_2$, —N(H)($C_{1-4}$ alkyl) (e.g., —$NHCH_3$) or —N($C_{1-4}$ alkyl)$_2$ (e.g., —N($CH_3$)$_2$).

In certain of these embodiments, each occurrence of $R^b$ and $R^c$ is independently selected from the group consisting of: H and —C(O)($C_{1-4}$ alkyl). For example, one of $R^b$ and $R^c$ is H, and the other is —C(O)($C_{1-4}$ alkyl) (e.g., —C(O)($CH_3$)).

In certain of these embodiments, each occurrence of $R^b$ and $R^c$ is independently selected from the group consisting of: $C_{1-4}$ alkyl and —C(O)($C_{1-4}$ alkyl). For example, one so of $R^b$ and $R^c$ is $C_{1-4}$ alkyl (e.g., $CH_3$), and the other is —C(O)($C_{1-4}$ alkyl) (e.g., —C(O)($CH_3$)).

In certain embodiments, $R^7$ is $CO_2R^a$.

In certain of these embodiments, $R^a$ is $C_{1-6}$ alkyl optionally substituted with —OH, —$NH_2$, —NH($C_{1-3}$ alkyl), —N($C_{1-3}$ alkyl)$_2$, —N(H)(C(=O)$C_{1-3}$ alkyl), or cyano.

In certain of these embodiments, $R^a$ is unsubstituted $C_{1-6}$ alkyl (e.g., $CH_3$ or $CH_2CH_3$).

In certain embodiments, $R^7$ is —OH.

Variables $R^3$ and $R^4$

In some embodiments, $R^3$ and $R^4$ are each independently selected from the group consisting of:
(i) hydrogen;
(ii) halo;
(iii) cyano;
(iv) $CO_2R^a$; and
(v) $CONR^bR^c$.

In certain embodiments, $R^3$ and $R^4$ are each independently selected from the group consisting of:
(i) hydrogen;
(ii) halo; and
(iv) $CO_2R^a$.

In some embodiments, one of $R^3$ and $R^4$ is hydrogen, and the other is a substituent other than hydrogen.

In certain embodiments, one of $R^3$ and $R^4$ is hydrogen, and the other is halo or $CO_2R^a$.

In certain embodiments, one of $R^3$ and $R^4$ is hydrogen, and the other is halo (e.g., Br).

In certain embodiments, one of $R^3$ and $R^4$ is hydrogen, and the other is $CO_2R^a$.

In certain of these embodiments, $R^a$ is $C_{1-4}$ alkyl optionally substituted with —OH, —$NH_2$, —NH($C_{1-3}$ alkyl), —N($C_{1-3}$ alkyl)$_2$, —N(H)(C(=O)$C_{1-3}$ alkyl), or cyano.

In certain of these embodiments, $R^a$ is unsubstituted $C_{1-4}$ alkyl (e.g., $CH_3$ or $CH_2CH_3$).

In some embodiments, $R^3$ is a substituent other than hydrogen, and $R^4$ is hydrogen.

In certain embodiments, $R^3$ is halo or $CO_2R^a$, and $R^4$ is hydrogen.

In certain embodiments, $R^3$ is halo (e.g., Br), and $R^4$ is hydrogen.

In certain embodiments, $R^3$ is $CO_2R^a$, and $R^4$ is hydrogen.

In certain of these embodiments, $R^a$ is $C_{1-6}$ alkyl optionally substituted with —OH, —$NH_2$, —NH($C_{1-3}$ alkyl), —N($C_{1-3}$ alkyl)$_2$, —N(H)(C(=O)$C_{1-3}$ alkyl), or cyano.

In certain of these embodiments, $R^a$ is unsubstituted $C_{1-6}$ alkyl (e.g., $CH_3$ or $CH_2CH_3$).

In some embodiments, $R^3$ is hydrogen, and $R^4$ is hydrogen.

In some embodiments, each of $R^3$ and $R^4$ is independently selected from the group consisting of:
(i) H;
(ii) halo;
(iii) cyano;
(vi) —($C_{0-3}$ alkylene)-$C_{3-10}$ cycloalkyl, wherein the cycloalkyl is optionally substituted with from 1-4 independently selected $R^f$;
(vii) —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;
(viii) —($C_{0-3}$ alkylene)-$C_{6-10}$ aryl optionally substituted with from 1-4 $R^g$;
(ix) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and
(xiv) $C_{1-4}$ haloalkyl.

In some embodiments, one of $R^3$ and $R^4$ (e.g., $R^3$) is:
(ii) halo;
(iii) cyano;
(vi) —($C_{0-3}$ alkylene)-$C_{3-10}$ cycloalkyl, wherein the cycloalkyl is optionally substituted with from 1-4 independently selected $R^f$;
(vii) —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;
(viii) —($C_{0-3}$ alkylene)-$C_{6-10}$ aryl optionally substituted with from 1-4 $R^g$;
(ix) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and
(xiv) $C_{1-4}$ haloalkyl; and the other (e.g., $R^4$) is H.

In some embodiments, one of $R^3$ and $R^4$ (e.g., $R^3$) is —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, In certain embodiments, one of $R^3$ and $R^4$ (e.g., $R^3$) is heteroaryl including from 5-6 ring atoms, wherein from 1-4 ring atoms are each independently selected from the group consisting of N, N($R^e$), O, and S, wherein the heteroaryl is optionally substituted with from 1-2 $R^g$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from the group consisting of N and N($R^e$), wherein the heteroaryl is optionally substituted with from 1-2 $R^g$; and the other (e.g., $R^4$) is H.

In certain embodiments, one of $R^3$ and $R^4$ (e.g., $R^3$) is heteroaryl including 5 ring atoms, wherein from 1 ring atom is independently selected from the group consisting of O and S (e.g., S), wherein the heteroaryl is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^g$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^g$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^g$; and the other (e.g., $R^4$) is H. In certain embodiments, one of $R^3$ and $R^4$ (e.g., $R^3$) is pyrazolyl, optionally substituted with from 1-2 $R^g$; and the other (e.g., $R^4$) is H.

In certain embodiments, one of $R^3$ and $R^4$ (e.g., $R^3$) is C-linked pyrazolyl, optionally substituted with from 1-2 $R^g$; and the other (e.g., $R^4$) is H.

In certain embodiments, one of $R^3$ and $R^4$ (e.g., $R^3$) is N-linked pyrazolyl, optionally substituted with from 1-2 $R^g$; and the other (e.g., $R^4$) is H.

In certain embodiments, one of $R^3$ and $R^4$ (e.g., $R^3$) is furyl or thienyl, optionally substituted with from 1-2 $R^g$; and the other (e.g., $R^4$) is H.

In certain embodiments, one of $R^3$ and $R^4$ (e.g., $R^3$) is thienyl, optionally substituted with from 1-2 $R^g$; and the other (e.g., $R^4$) is H.

In some embodiments, one of $R^3$ and $R^4$ (e.g., $R^3$) is —($C_{0-3}$ alkylene)-$C_{6-10}$ aryl, wherein the aryl is optionally substituted with from 1-3 $R^g$; and the other (e.g., $R^4$) is H.

In certain embodiments, one of $R^3$ and $R^4$ (e.g., $R^3$) is $C_{1-10}$ aryl (e.g., phenyl), optionally substituted with from 1-3 $R^g$; and the other (e.g., $R^4$) is H.

In some embodiments, one of $R^3$ and $R^4$ (e.g., $R^3$) is —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$ (e.g., oxo), and the other (e.g., $R^4$) is H.

Variable $R^1$

In some embodiments, $R^1$ is hydrogen.

In some embodiments, $R^1$ is X—$R^5$, wherein X is unbranched chain $C_4$ alkylene, and $R^5$ is hydrogen, —OH, $C_{1-4}$ alkoxy, —$C_{1-4}$ haloalkoxy, $CO_2R^a$; —$CONR^bR^c$, cyano, or —$NR^bR^c$.

In some embodiments, X is unbranched chain $C_{2-4}$ alkylene. In some embodiments, X is unbranched chain $C_{5-6}$ alkylene.

In some embodiments, $R^5$ is —OH, $C_{1-4}$ alkoxy, —$C_{1-4}$ haloalkoxy, $CO_2R^a$; or —$NR^bR^c$.

In certain embodiments, $R^5$ is —OH, $C_{1-4}$ alkoxy, —$C_{1-4}$ haloalkoxy, or $CO_2R^a$.

In certain embodiments, $R^5$ is $C_{1-4}$ alkoxy or —$C_{1-4}$ haloalkoxy (e.g., $C_{1-4}$ alkoxy, e.g., $OCH_3$).

In certain embodiments, $R^5$ is $CO_2R^a$.

In some embodiments, $R^5$ is H. In certain of these embodiments, $R^1$ is unsubstituted $C_{1-2}$ alkyl (e.g., $CH_3$).

In certain of these embodiments, R is $C_{1-6}$ alkyl optionally substituted with —OH, —$NH_2$, —NH($C_{1-3}$ alkyl), —N($C_{1-3}$ alkyl)$_2$, —N(H)(C(=O)$C_{1-3}$ alkyl), or cyano.

In certain of these embodiments, $R^a$ is unsubstituted $C_{1-6}$ alkyl (e.g., $CH_3$ or $CH_2CH_3$).

In some embodiments, $R^1$ is:

(iii) ($C_{1-3}$ alkylene)aryl, wherein the aryl is optionally substituted with from 1-3 $R^d$; or (iv) ($C_{1-3}$ alkylene)heteroaryl including from 5-6 ring atoms, wherein from 1-4 ring atoms are each independently selected from the group consisting of nitrogen, oxygen and sulfur, and wherein the heteroaryl is optionally substituted with from 1-3 $R^d$.

In certain embodiments, $R^1$ is ($C_{1-3}$ alkylene)aryl, wherein the aryl is optionally substituted with from 1-3 (e.g., 2, 1) $R^d$.

In certain embodiments, $R^1$ is ($C_{1-3}$ alkylene)phenyl, wherein the phenyl is optionally substituted with from 1-3 (e.g., 2, 1) $R^d$.

In certain embodiments, $R^1$ is ($C_{1-3}$ alkylene)aryl, wherein the aryl is substituted with from 1-3 (e.g., 2, 1) $R^d$.

In certain embodiments, $R^1$ is ($C_{1-3}$ alkylene)phenyl, wherein the phenyl is substituted with from 1-3 (e.g., 2, 1) $R^d$.

In certain embodiments, $R^1$ is ($C_{1-3}$ alkylene)phenyl, wherein the phenyl is substituted with 1 $R^d$.

In certain of these embodiments, $R^d$, or at least one $R^d$ is $C_{1-4}$ (e.g., $C_{1-4}$, $C_{1-3}$, $C_{1-2}$, $C_1$) alkyl optionally substituted with from 1-2 substituents independently selected from —OH, $C_{1-4}$ alkoxy, $C_{1-4}$ haloalkoxy, —$CO_2R^a$; —$CONR^bR^c$, cyano, and —$NR^bR^c$.

In certain of these embodiments, $R^d$, or at least one $R^d$ is $C_{1-6}$ (e.g., $C_{1-4}$, $C_{1-3}$, $C_{1-2}$, $C_1$) alkyl substituted with from 1-2 substituents independently selected from —OH, $C_{1-4}$ alkoxy, $C_{1-4}$ haloalkoxy, —$CO_2R^a$; —$CONR^bR^c$, cyano, and —$NR^bR^c$. By way of example, $R^d$ can be —$CH_2NR^bR^c$, e.g., —$CH_2NH_2$.

Non-Limiting Combinations

[1] In some embodiments:

$R^2$ is Y—$R^6$, wherein:

Y is $C_{2-8}$ alkylene, which is optionally substituted with from 1-4 $R^e$; and $R^6$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur; and $R^1$ is hydrogen.

In some of these embodiments, each of $R^3$ and $R^4$ is independently selected from the group consisting of:

(i) H;

(ii) halo;

(iii) cyano;

(vi) —($C_{0-3}$ alkylene)-$C_{3-10}$ cycloalkyl, wherein the cycloalkyl is optionally substituted with from 1-4 independently selected $R^f$;

(vii) —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;

(viii) —($C_{0-3}$ alkylene)-$C_{6-10}$ aryl optionally substituted with from 1-4 $R^g$;

(ix) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and (xiv) $C_{1-4}$ haloalkyl.

In some embodiments, one of $R^3$ and $R^4$ (e.g., $R^3$) is:

(ii) halo;

(iii) cyano;

(vi) —($C_{0-3}$ alkylene)-$C_{3-10}$ cycloalkyl, wherein the cycloalkyl is optionally substituted with from 1-4 independently selected $R^f$;

(vii) —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;

(viii) —($C_{0-3}$ alkylene)-$C_{6-10}$ aryl optionally substituted with from 1-4 $R^g$;

(ix) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and (xiv) $C_{1-4}$ haloalkyl; and the other (e.g., $R^4$) is H.

In some embodiments, one of $R^3$ and $R^4$ (e.g., $R^3$) is —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, In certain embodiments, one of $R^3$ and $R^4$ (e.g., $R^3$) is heteroaryl including from 5-6 ring atoms, wherein from 1-4 ring atoms are each independently selected from the group consisting of N, N($R^e$), O, and S, wherein the heteroaryl is optionally substituted with from 1-2 $R^g$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from the group consisting of N and N($R^e$), wherein the heteroaryl is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^g$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^g$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^g$; and the other (e.g., $R^4$) is H. In certain embodiments, one of $R^3$ and $R^4$ (e.g., $R^3$) is pyrazolyl, optionally substituted with from 1-2 $R^g$; and the other (e.g., $R^4$) is H.

In certain embodiments, one of $R^3$ and $R^4$ (e.g., $R^3$) is C-linked pyrazolyl, optionally substituted with from 1-2 $R^g$; and the other (e.g., $R^4$) is H.

In certain embodiments, one of $R^3$ and $R^4$ (e.g., $R^3$) is N-linked pyrazolyl, optionally substituted with from 1-2 $R^g$; and the other (e.g., $R^4$) is H.

In some embodiments, one of $R^3$ and $R^4$ (e.g., $R^3$) is —($C_{0-3}$ alkylene)-$C_{6-10}$ aryl, wherein the aryl is optionally substituted with from 1-3 $R^g$; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^g$; and the other (e.g., $R^4$) is H.

In some embodiments, one of $R^3$ and $R^4$ (e.g., $R^3$) is —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from the group consisting of $N(R^e)$, O, and S, wherein the heterocyclyl is optionally substituted with from 1-4 independently selected $R^f$ (e.g., oxo), and the other (e.g., $R^4$) is H.

[2] In some embodiments:

$R^2$ is $Y-R^6$, wherein:

Y is $C_{2-8}$ alkylene, which is optionally substituted with from 1-4 $R^e$; and $R^6$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur;

$R^1$ is hydrogen; and $R^3$ and $R^4$ are each independently selected from the group consisting of:

(i) hydrogen;

(ii) halo; and (iv) $CO_2R^a$.

In certain of these embodiments, one of $R^3$ and $R^4$ is other than hydrogen.

[3] In some embodiments:

$R^2$ is $Y-R^6$, wherein:

Y is $CO_2$ alkylene, which is optionally substituted with from 1-4 $R^e$; and $R^6$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur; and $R^1$ is $X-R^5$, wherein X is unbranched chain $C_{2-6}$ alkylene, and $R^5$ is hydrogen, —OH, $C_{1-4}$ alkoxy, —$C_{1-4}$ haloalkoxy, $CO_2R^a$; —$CONR^bR^c$, cyano, or —$NR^bR^c$.

In some embodiments, each of $R^3$ and $R^4$ is independently selected from the group consisting of:

(i) H;

(ii) halo;

(iii) cyano;

(vi) —$(C_{0-3}$ alkylene)-$C_{3-10}$ cycloalkyl, wherein the cycloalkyl is optionally substituted with from 1-4 independently selected $R^f$;

(vii) —$(C_{0-3}$ alkylene)-heterocyclyl including from 3-10 ring atoms, wherein from 1-3 ring atoms are each independently selected from the group consisting of $N(R^e)$, O, and S, wherein the heterocyclyl is optionally substituted with from 1-4 independently selected $R^f$;

(viii) —$(C_{0-3}$ alkylene)-$C_{6-10}$ aryl optionally substituted with from 1-4 $R^g$;

(ix) —$(C_{0-3}$ alkylene)-heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and (xiv) $C_{1-4}$ haloalkyl.

In some embodiments, one of $R^3$ and $R^4$ (e.g., $R^3$) is:

(ii) halo;

(iii) cyano;

(vi) —$(C_{0-3}$ alkylene)-$C_{3-10}$ cycloalkyl, wherein the cycloalkyl is optionally substituted with from 1-4 independently selected $R^f$;

(vii) —$(C_{0-3}$ alkylene)-heterocyclyl including from 3-10 ring atoms, wherein from 1-3 ring atoms are each independently selected from the group consisting of $N(R^e)$, O, and S, wherein the heterocyclyl is optionally substituted with from 1-4 independently selected $R^f$;

(viii) —$(C_{0-3}$ alkylene)-$C_{6-10}$ aryl optionally substituted with from 1-4 $R^g$;

(ix) —$(C_{0-3}$ alkylene)-heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and (xiv) $C_{1-4}$ haloalkyl; and the other (e.g., $R^4$) is H.

In some embodiments, one of $R^3$ and $R^4$ (e.g., $R^3$) is —$(C_{0-3}$ alkylene)-heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, In certain embodiments, one of $R^3$ and $R^4$ (e.g., $R^3$) is heteroaryl including from 5-6 ring atoms, wherein from 1-4 ring atoms are each independently selected from the group consisting of N, $N(R^e)$, O, and S, wherein the heteroaryl is optionally substituted with from 1-2 $R^g$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from the group consisting of N and $N(R^e)$, wherein the heteroaryl is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^g$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^g$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^g$; and the other (e.g., $R^4$) is H. In certain embodiments, one of $R^3$ and $R^4$ (e.g., $R^3$) is pyrazolyl, optionally substituted with from 1-2 $R^g$; and the other (e.g., $R^4$) is H.

In certain embodiments, one of $R^3$ and $R^4$ (e.g., $R^3$) is C-linked pyrazolyl, optionally substituted with from 1-2 $R^g$; and the other (e.g., $R^4$) is H.

In certain embodiments, one of $R^3$ and $R^4$ (e.g., $R^3$) is N-linked pyrazolyl, optionally substituted with from 1-2 $R^g$; and the other (e.g., $R^4$) is H.

In some embodiments, one of $R^3$ and $R^4$ (e.g., $R^3$) is —$(C_{0-3}$ alkylene)-$C_{6-10}$ aryl, wherein the aryl is optionally substituted with from 1-3 $R^g$; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^g$; and the other (e.g., $R^4$) is H.

In some embodiments, one of $R^3$ and $R^4$ (e.g., $R^3$) is —$(C_{0-3}$ alkylene)-heterocyclyl including from 3-10 ring atoms, wherein from 1-3 ring atoms are each independently selected from the group consisting of $N(R^e)$, O, and S, wherein the heterocyclyl is optionally substituted with from 1-4 independently selected $R^f$; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from the group consisting of $N(R^e)$, O, and S, wherein the heterocyclyl is optionally substituted with from 1-4 independently selected $R^f$ (e.g., oxo), and the other (e.g., $R^4$) is H.

[4] In some embodiments:
$R^2$ is Y—$R^6$, wherein:
Y is $C_{2-8}$ alkylene, which is optionally substituted with from 1-4 $R^e$; and
$R^6$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur;
$R^1$ is X—$R^5$, wherein X is unbranched chain $C_{2-6}$ alkylene, and $R^5$ is hydrogen, —OH, $C_{1-4}$ alkoxy, —$C_{1-4}$ haloalkoxy, $CO_2R^a$; —$CONR^bR^c$, cyano, or —$NR^bR^c$; and
$R^3$ and $R^4$ are each independently selected from the group consisting of:
(i) hydrogen;
(ii) halo; and
(iv) $CO_2R^a$.

In certain of these embodiments, one of $R^3$ and $R^4$ is other than hydrogen.

[5] In some embodiments:
$R^2$ is Y—$R^6$, wherein:
Y is $C_{2-8}$ alkylene, which is optionally substituted with from 1-4 $R^e$; and
$R^6$ is —OH, $CO_2R^a$; —$CONR^bR^c$, —$NR^bR^c$, or heteroaryl including from 5-6 ring atoms, wherein from 1-4 ring atoms are each independently selected from the group consisting of nitrogen, oxygen and sulfur; and
$R^1$ is:
(iii) ($C_{1-3}$ alkylene)aryl, wherein the aryl is optionally substituted with from 1-3 $R^d$; or
(iv) ($C_{1-3}$ alkylene)heteroaryl including from 5-6 ring atoms, wherein from 1-4 ring atoms are each independently selected from the group consisting of nitrogen, oxygen and sulfur, and wherein the heteroaryl is optionally substituted with from 1-3 $R^d$.

In some embodiments, each of $R^3$ and $R^4$ is independently selected from the group consisting of:
(i) H;
(ii) halo;
(iii) cyano;
(vi) —$(C_{0-3}$ alkylene)-$C_{3-10}$ cycloalkyl, wherein the cycloalkyl is optionally substituted with from 1-4 independently selected $R^f$;

(vii) —$(C_{0-3}$ alkylene)-heterocyclyl including from 3-10 ring atoms, wherein from 1-3 ring atoms are each independently selected from the group consisting of $N(R^e)$, O, and S, wherein the heterocyclyl is optionally substituted with from 1-4 independently selected $R^f$;
(viii) —$(C_{0-3}$ alkylene)-$C_{6-10}$ aryl optionally substituted with from 1-4 $R^g$;
(ix) —$(C_{0-3}$ alkylene)-heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and
(xiv) $C_{1-4}$ haloalkyl.

In some embodiments, one of $R^3$ and $R^4$ (e.g., $R^3$) is:
(ii) halo;
(iii) cyano;
(vi) —$(C_{0-3}$ alkylene)-$C_{3-10}$ cycloalkyl, wherein the cycloalkyl is optionally substituted with from 1-4 independently selected $R^f$;
(vii) —$(C_{0-3}$ alkylene)-heterocyclyl including from 3-10 ring atoms, wherein from 1-3 ring atoms are each independently selected from the group consisting of $N(R^e)$, O, and S, wherein the heterocyclyl is optionally substituted with from 1-4 independently selected $R^f$;
(viii) —$(C_{0-3}$ alkylene)-$C_{6-10}$ aryl optionally substituted with from 1-4 $R^g$;
(ix) —$(C_{0-3}$ alkylene)-heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and
(xiv) $C_{1-4}$ haloalkyl; and the other (e.g., $R^4$) is H.

In some embodiments, one of $R^3$ and $R^4$ (e.g., $R^3$) is —$(C_{0-3}$ alkylene)-heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from the group consisting of N, $N(R^e)$, O, and S, wherein the heteroaryl is optionally substituted with from 1-3 $R^g$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, In certain embodiments, one of $R^3$ and $R^4$ (e.g., $R^3$) is heteroaryl including from 5-6 ring atoms, wherein from 1-4 ring atoms are each independently selected from the group consisting of N, $N(R^e)$, O, and S, wherein the heteroaryl is optionally substituted with from 1-2 $R^g$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from the group consisting of N and N($R^e$), wherein the heteroaryl is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^g$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^g$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^g$; and the other (e.g., $R^4$) is H. In certain embodiments, one of $R^3$ and $R^4$ (e.g., $R^3$) is pyrazolyl, optionally substituted with from 1-2 $R^g$; and the other (e.g., $R^4$) is H.

In certain embodiments, one of $R^3$ and $R^4$ (e.g., $R^3$) is C-linked pyrazolyl, optionally substituted with from 1-2 $R^g$; and the other (e.g., $R^4$) is H.

In certain embodiments, one of $R^3$ and $R^4$ (e.g., $R^3$) is N-linked pyrazolyl, optionally substituted with from 1-2 $R^g$; and the other (e.g., $R^4$) is H.

In some embodiments, one of $R^3$ and $R^4$ (e.g., $R^3$) is —($C_{0-3}$ alkylene)-$C_{6-10}$ aryl, wherein the aryl is optionally substituted with from 1-3 $R^g$; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^g$; and the other (e.g., $R^4$) is H.

In some embodiments, one of $R^3$ and $R^4$ (e.g., $R^3$) is —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$ (e.g., oxo), and the other (e.g., $R^4$) is H.

[6] In some embodiments:
$R^2$ is Y—$R^6$, wherein:
Y is $C_{2-8}$ alkylene, which is optionally substituted with from 1-4 $R^e$; and
$R^6$ is —OH, $CO_2R^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur;
$R^1$ is:
(iii) ($C_{1-3}$ alkylene)aryl, wherein the aryl is optionally substituted with from 1-3 $R^d$; or
(iv) ($C_{1-3}$ alkylene)heteroaryl including from 5-6 ring atoms, wherein from 1-4 ring atoms are each independently selected from the group consisting of nitrogen, oxygen and sulfur, and wherein the heteroaryl is optionally substituted with from 1-3 $R^d$. and
$R^3$ and $R^4$ are each independently selected from the group consisting of:
(i) hydrogen;
(ii) halo; and
(iv) $CO_2R^a$.

In certain of these embodiments, one of $R^3$ and $R^4$ is other than hydrogen.

[7] In some embodiments:
$R^2$ is —($Y^1$)$_n$—$Y^2$—($Y^3$)$_p$—$R^{6'}$, wherein:
each of n and p is independently 0 or 1;
each of $Y^1$ and Y is, independently, $C_{1-3}$ alkylene, which is optionally substituted with from 1-2 $R^e$,
$Y^2$ is $C_{3-6}$ cycloalkylene or heterocycloalkylene including from 3-8 ring atoms, wherein from 1-2 ring atoms are each independently selected from the group consisting of N, N($R^f$) and oxygen, and wherein $Y^2$ is optionally further substituted with from 1-4 $R^g$, and
$R^{6'}$ is —OH, $CO_2R^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur;
and $R^1$ is hydrogen.

[8] In some embodiments:
$R^2$ is —($Y^1$)$_n$—$Y^2$—($Y^3$)$_p$—$R^{6'}$, wherein:
each of n and p is independently 0 or 1;
each of $Y^1$ and $Y^3$ is, independently, $C_{1-3}$ alkylene, which is optionally substituted with from 1-2 $R^e$,
$Y^2$ is $C_{3-6}$ cycloalkylene or heterocycloalkylene including from 3-8 ring atoms, wherein from 1-2 ring atoms are each independently selected from the group consisting of N, N($R^f$) and oxygen, and wherein $Y^2$ is optionally further substituted with from 1-4 $R^g$, and
$R^{6'}$ is H, —OH, $CO_2R^a$; —CONR$^b$R$^c$, —NR$^b$R$^c$, or heteroaryl including from 5-6 ring atoms, wherein from 1-4 ring atoms are each independently selected from the group consisting of nitrogen, oxygen and sulfur, wherein $R^{6'}$ cannot be H when $Y^2$ is $C_{3-6}$ cycloalkylene optionally substituted with from 1-4 $R^g$;
and $R^1$ is hydrogen or unsubstituted $C_{1-2}$ alkyl (e.g., $CH_3$).

In some embodiments of combination [7] and [8], each of $R^3$ and $R^4$ is independently selected from the group consisting of:
(i) H;
(ii) halo;
(iii) cyano;
(vi) —($C_{0-3}$ alkylene)-$C_{3-10}$ cycloalkyl, wherein the cycloalkyl is optionally substituted with from 1-4 independently selected $R^f$;
(vii) —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;
(viii) —($C_{0-3}$ alkylene)-$C_{6-10}$ aryl optionally substituted with from 1-4 $R^g$;
(ix) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and
(xiv) $C_{1-4}$ haloalkyl.

In some embodiments, one of $R^3$ and $R^4$ (e.g., $R^3$) is:
(ii) halo;
(iii) cyano;
(vi) —($C_{0-3}$ alkylene)-$C_{3-10}$ cycloalkyl, wherein the cycloalkyl is optionally substituted with from 1-4 independently selected $R^f$;
(vii) —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$;
(viii) —($C_{0-3}$ alkylene)-$C_{6-10}$ aryl optionally substituted with from 1-4 $R^g$;

(ix) —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and (xiv) $C_{1-4}$ haloalkyl; and the other (e.g., $R^4$) is H.

In some embodiments, one of $R^3$ and $R^4$ (e.g., $R^3$) is —($C_{0-3}$ alkylene)-heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from the group consisting of N, N($R^e$), O, and S, wherein the heteroaryl is optionally substituted with from 1-3 $R^g$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, In certain embodiments, one of $R^3$ and $R^4$ (e.g., $R^3$) is heteroaryl including from 5-6 ring atoms, wherein from 1-4 ring atoms are each independently selected from the group consisting of N, N($R^e$), O, and S, wherein the heteroaryl is optionally substituted with from 1-2 $R^g$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from the group consisting of N and N($R^e$), wherein the heteroaryl is optionally substituted with from 1-2 $R^g$; and the other (e.g., $R^4$) is H.

In certain embodiments, one of $R^3$ and $R^4$ (e.g., $R^3$) is heteroaryl including 5 ring atoms, wherein from 1 ring atom is independently selected from the group consisting of O and S (e.g., S), wherein the heteroaryl is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^g$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^g$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^g$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^g$; and the other (e.g., $R^4$) is H. In certain embodiments, one of $R^3$ and $R^4$ (e.g., $R^3$) is pyrazolyl, optionally substituted with from 1-2 $R^g$; and the other (e.g., $R^4$) is H.

In certain embodiments, one of $R^3$ and $R^4$ (e.g., $R^3$) is C-linked pyrazolyl, optionally substituted with from 1-2 $R^g$; and the other (e.g., $R^4$) is H.

In certain embodiments, one of $R^3$ and $R^4$ (e.g., $R^3$) is N-linked pyrazolyl, optionally substituted with from 1-2 $R^g$; and the other (e.g., $R^4$) is H.

In certain embodiments, one of $R^3$ and $R^4$ (e.g., $R^3$) is furyl or thienyl, optionally substituted with from 1-2 $R^g$; and the other (e.g., $R^4$) is H.

In certain embodiments, one of $R^3$ and $R^4$ (e.g., $R^3$) is thienyl, optionally substituted with from 1-2 $R^g$; and the other (e.g., $R^4$) is H.

In some embodiments, one of $R^3$ and $R^4$ (e.g., $R^3$) is —($C_{0-3}$ alkylene)-$C_{6-10}$ aryl, wherein the aryl is optionally substituted with from 1-3 $R^g$; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^g$; and the other (e.g., $R^4$) is H.

In some embodiments, one of $R^3$ and $R^4$ (e.g., $R^3$) is —($C_{0-3}$ alkylene)-heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from the group consisting of N($R^e$), O, and S, wherein the heterocyclyl is optionally substituted with from 1-4 independently selected $R^f$ (e.g., oxo), and the other (e.g., $R^4$) is H.

Embodiments of any one of combinations [1]-[8] can include one or more of the following features.

Y can be unbranched $C_{2-6}$ (e.g., $C_{2-4}$, $C_{2-3}$, $C_2$) alkylene, which is optionally substituted with from 1-4 (e.g., 1-2, 1) $R^e$. In certain embodiments, Y is unbranched $C_{2-6}$ (e.g., $C_{2-4}$, $C_{2-3}$, $C_2$) alkylene, which is unsubstituted (e.g., $C_2$ alkylene or $C_3$ alkylene; e.g., $C_3$ alkylene).

$R^6$ can be —OH, $CO_2R^a$;—or —$NR^bR^c$.

$R^6$ can be —$NR^bR^c$.

Each occurrence of $R^b$ and $R^c$ can be independently selected from the group consisting of: H, $C_{1-4}$ alkyl, —C(O)($C_{1-4}$ alkyl), —C(O)O($C_{1-4}$ alkyl), —S(O)$_{1-2}$($R^h$), —C(O)$NR^jR^k$, —OH, and $C_{1-4}$ alkoxy.

Each occurrence of $R^b$ and $R^c$ can be independently selected from the group consisting of: H, $C_{1-4}$ alkyl, —C(O)($C_{1-4}$ alkyl), —C(O)O($C_{1-4}$ alkyl), —S(O)$_{1-2}$($R^h$), and —C(O)$NR^jR^k$.

Each occurrence of $R^b$ and $R^c$ can be independently selected from the group consisting of: H, $C_{1-4}$ alkyl, and —C(O)($C_{1-4}$ alkyl).

Each occurrence of $R^b$ and $R^c$ can be independently selected from the group consisting of: H and $C_{1-4}$ alkyl. For example, $R^6$ can be —$NH_2$, —N(H)($C_{1-4}$ alkyl) (e.g., —$NHCH_3$) or —N($C_{1-4}$ alkyl)$_2$ (e.g., —N($CH_3$)$_2$).

Each occurrence of $R^b$ and $R^c$ can be independently selected from the group consisting of: H and —C(O)($C_{1-4}$ alkyl). For example, one of $R^b$ and $R^c$ is H, and the other is —C(O)($C_{1-4}$ alkyl) (e.g., —C(O)($CH_3$)).

Each occurrence of $R^b$ and $R^c$ can be independently selected from the group consisting of: $C_{1-4}$ alkyl and —C(O)($C_{1-4}$ alkyl). For example, one of $R^b$ and $R^c$ is $C_{1-4}$ alkyl (e.g., $CH_3$), and the other is —C(O)($C_{1-4}$ alkyl) (e.g., —C(O)($CH_3$)).

$R^6$ can be $CO_2R^a$. $R^a$ can be $C_{1-6}$ alkyl optionally substituted with —OH, —$NH_2$, —NH($C_{1-3}$ alkyl), —N($C_{1-3}$ alkyl)$_2$, —N(H)(C(=O)$C_{1-3}$ alkyl), or cyano; e.g., $R^a$ can be unsubstituted $C_{1-6}$ alkyl (e.g., $CH_3$ or $CH_2CH_3$).

$R^6$ can be —OH (in certain embodiments, $R^2$ is —$CH_2CH_2CH_2OH$).

X can be unbranched chain $C_{2-4}$ alkylene. In some embodiments, X is unbranched chain $C_{5-6}$ alkylene.

$R^5$ can be —OH, $C_{1-4}$ alkoxy, —$C_{1-4}$ haloalkoxy, $CO_2R^a$; or —$NR^bR^c$.

$R^5$ can be —OH, $C_{1-4}$ alkoxy, —$C_{1-4}$ haloalkoxy, or $CO_2R^a$.

$R^5$ can be $C_{1-4}$ alkoxy or —$C_{1-4}$ haloalkoxy (e.g., $C_{1-4}$ alkoxy, e.g., $OCH_3$).

$R^5$ can be $CO_2R^a$. R can be $C_{1-6}$ alkyl optionally substituted with —OH, —$NH_2$, —$NH(C_{1-3}$ alkyl), —$N(C_{1-3}$ alkyl)$_2$, —N(H)(C(=O)$C_{1-3}$ alkyl), or cyano; e.g., $R^a$ can be unsubstituted $C_{1-6}$ alkyl (e.g., $CH_3$ or $CH_2CH_3$).

$R^5$ can be H; e.g., $R^1$ can be unsubstituted $C_{1-2}$ alkyl (e.g., $CH_3$).

$R^1$ can be ($C_{1-3}$ alkylene)aryl, wherein the aryl is optionally substituted with from 1-3 (e.g., 2, 1) $R^d$.

$R^1$ can be ($C_{1-3}$ alkylene)phenyl, wherein the phenyl is optionally substituted with from 1-3 (e.g., 2, 1) $R^d$.

$R^1$ can be ($C_{1-3}$ alkylene)aryl, wherein the aryl is substituted with from 1-3 (e.g., 2, 1) $R^d$.

$R^1$ can be ($C_{1-3}$ alkylene)phenyl, wherein the phenyl is substituted with from 1-3 (e.g., 2, 1) $R^d$.

$R^1$ can be ($C_{1-3}$ alkylene)phenyl, wherein the phenyl is substituted with 1 $R^d$.

$R^d$, or at least one $R^d$ can be $C_{1-6}$ (e.g., $C_{1-4}$, $C_{1-3}$, $C_{1-2}$, $C_1$) alkyl optionally substituted with from 1-2 substituents independently selected from —OH, $C_{1-4}$ alkoxy, $C_{1-4}$ haloalkoxy, —$CO_2R^a$; —$CONR^bR^c$, cyano, and —$NR^bR^c$.

$R^d$, or at least one $R^d$ can be $C_{1-6}$ (e.g., $C_{1-4}$, $C_{1-3}$, $C_{1-2}$, $C_1$) alkyl substituted with from 1-2 substituents independently selected from —OH, $C_{1-4}$ alkoxy, $C_{1-4}$ haloalkoxy, —$CO_2R^a$; —$CONR^bR^c$, cyano, and —$NR^bR^c$. By way of example, $R^d$ can be —$CH_2NR^bR^c$, e.g., —$CH_2NH_2$.

One of $R^3$ and $R^4$ (e.g., $R^3$) can be hydrogen, and the other (e.g., $R^3$) can be a substituent other than hydrogen.

One of $R^3$ and $R^4$ (e.g., $R^3$) can be hydrogen, and the other (e.g., $R^3$) can be halo or $CO_2R^a$.

One of $R^3$ and $R^4$ (e.g., $R^3$) can be hydrogen, and the other (e.g., $R^3$) can be halo (e.g., Br).

One of $R^3$ and $R^4$ (e.g., $R^3$) can be hydrogen, and the other (e.g., $R^3$) can be $CO_2R^a$. $R^a$ can be $C_{1-6}$ alkyl optionally substituted with —OH, —$NH_2$, —$NH(C_{1-3}$ alkyl), —$N(C_{1-3}$ alkyl)$_2$, —N(H)(C(=O)$C_{1-3}$ alkyl), or cyano; e.g., $R^a$ can be unsubstituted $C_{1-6}$ alkyl (e.g., $CH_3$ or $CH_2CH_3$).

$R^3$ can be hydrogen, and $R^3$ can be hydrogen.

In some embodiments, the compound of Formula I is a compound selected from the group consisting of compounds in Table 1 below. The biological assays used to test the compounds is discussed in the examples section. A blank table cell indicates a lack of data of the type specified in the cell's corresponding column. Key to activity ranges: A=≤1 µM; B=>1 µM, ≤20 µM; C=>20 µM, ≤100 µM; D=>10 µM.

TABLE 1

| Compound | Structure | hNLRP3 Agonist EC$_{50}$ (µM) | TLR7 EC$_{50}$ (µM) | TLR8 EC$_{50}$ (µM) | LCMS [M + H]+ |
|---|---|---|---|---|---|
| 101 | 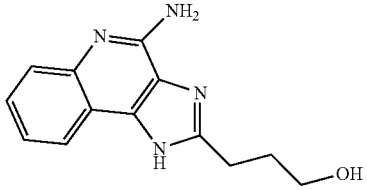 [SMILES: Nc1nc2ccccc2c2[nH]c(CCCO)nc12] | C | C | C | 243.0 |
| 102 | 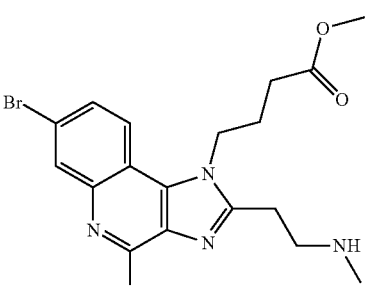 | | | | |
| 103 | 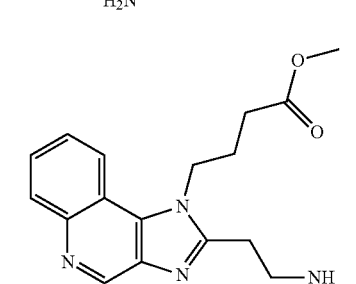 | | | | |

TABLE 1-continued

| Compound | Structure | hNLRP3 Agonist EC$_{50}$ (µM) | TLR7 EC$_{50}$ (µM) | TLR8 EC$_{50}$ (µM) | LCMS [M + H]+ |
|---|---|---|---|---|---|
| 104 | 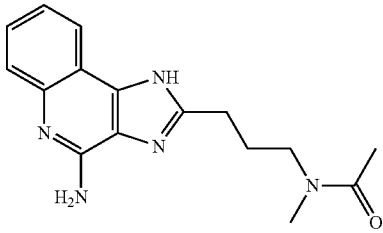 [SMILES: CC(=O)N(C)CCCc1nc2c(N)nc3ccccc3c2[nH]1] | | | | |
| 105 | 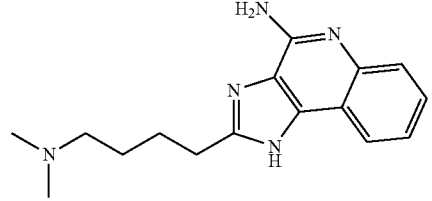 [SMILES: CN(C)CCCCc1nc2c(N)nc3ccccc3c2[nH]1] | | | | |
| 106 | 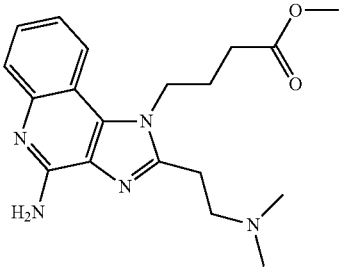 [SMILES: COC(=O)CCCn1c(CCN(C)C)nc2c(N)nc3ccccc3c21] | | | | | and pharmaceutically acceptable salts thereof.

In some embodiments, the compound of Formula I is a compound selected from the group consisting of compounds in Table 2 below. The biological assays used to test the compounds is discussed in the examples section. A blank table cell indicates a lack of data of the type specified in the cell's corresponding column. Key to activity ranges: A=≤1 µM; B=>1 µM, ≤20 µM; C=>20 µM, ≤100 µM; D=>100 µM.

TABLE 2

| Structure | Compound | hNLRP3 Agonist EC$_{50}$ (µM) | TLR7 EC$_{50}$ (µM) | TLR8 EC$_{50}$ (µM) | LCMS [M + H]+ |
|---|---|---|---|---|---|
| 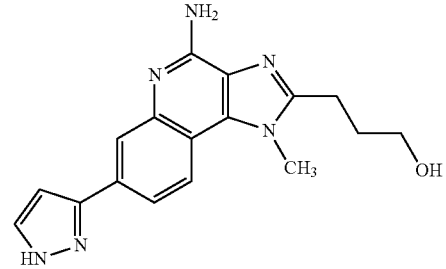 [SMILES: Cn1c(CCCO)nc2c(N)nc3cc(-c4cc[nH]n4)ccc3c21] | 107 | A | D | D | 323.2 |
| 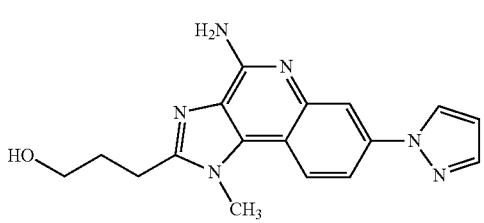 [SMILES: Cn1c(CCCO)nc2c(N)nc3cc(-n4cccn4)ccc3c21] | 108 | A | D | D | 323.2 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 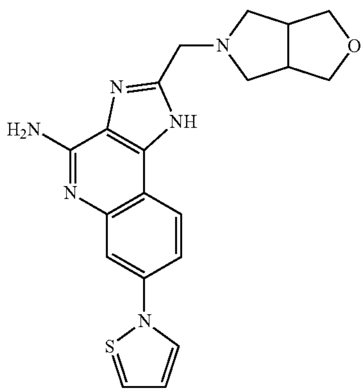 | 109 | A | | | 376.2 |
| 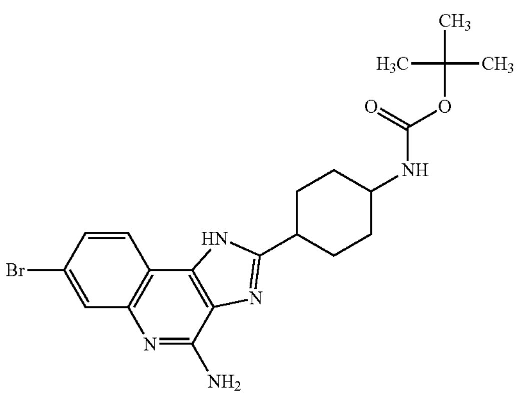 [SMILES: CC(C)(C)OC(=O)NC1CCC(c2nc3c(N)nc4cc(Br)ccc4c3[nH]2)CC1] | 110 | B | D | D | 460.2 |
| 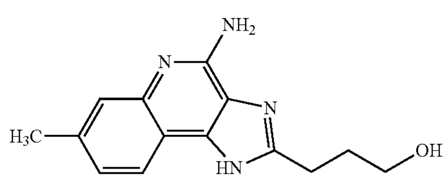 [SMILES: Cc1ccc2c(c1)nc(N)c1nc(CCCO)[nH]c12] | 111 | B | D | C | 257.1 |
| 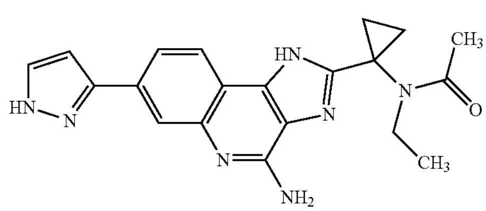 [SMILES: CCN(C(C)=O)C1(c2nc3c(N)nc4cc(-c5cc[nH]n5)ccc4c3[nH]2)CC1] | 112 | B | D | D | 376.0 |
| 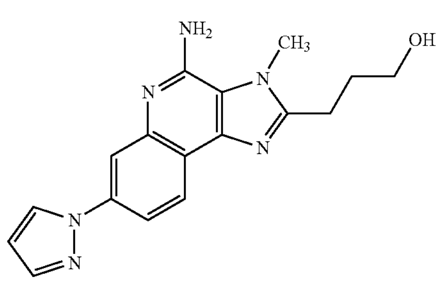 [SMILES: Cn1c(CCCO)nc2c3ccc(-n4cccn4)cc3nc(N)c21] | 113 | B | D | D | 323.2 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
| --- | --- | --- | --- | --- | --- |
| 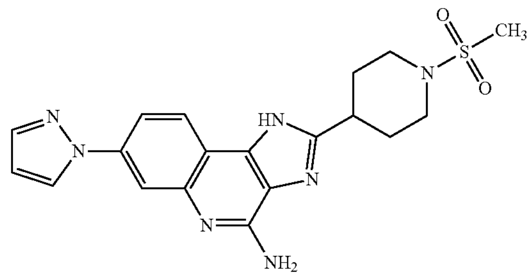 [SMILES: CS(=O)(=O)N1CCC(c2nc3c(N)nc4cc(-n5cccn5)ccc4c3[nH]2)CC1] | 114 | B | D | D | 412.1 |
| 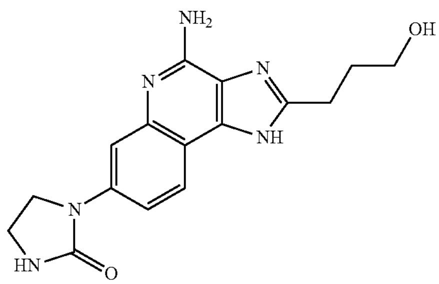 [SMILES: Nc1nc2cc(N3CCNC3=O)ccc2c2[nH]c(CCCO)nc12] | 115 | B | D | D | 327.3 |
| 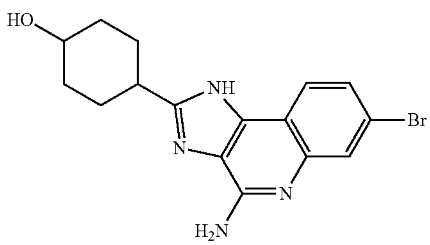 [SMILES: Nc1nc2cc(Br)ccc2c2[nH]c(C3CCC(O)CC3)nc12] | 116 | B | | | 363.3 |
| 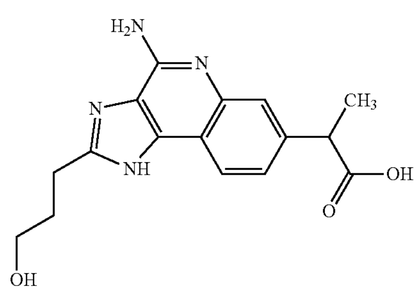 [SMILES: CC(C(=O)O)c1ccc2c(c1)nc(N)c1nc(CCCO)[nH]c12] | 117 | B | D | D | 314.9 |
| 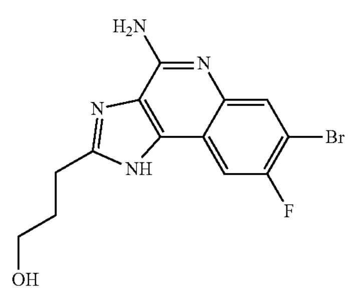 [SMILES: Nc1nc2cc(Br)c(F)cc2c2[nH]c(CCCO)nc12] | 118 | B | D | D | 341.0 |

TABLE 2-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 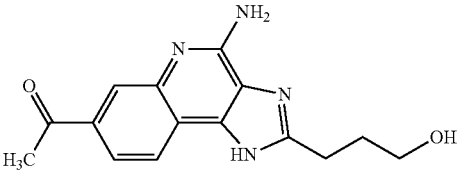 [SMILES: CC(=O)c1ccc2c(c1)nc(N)c1nc(CCCO)[nH]c12] | 119 | B | D | D | 285.1 |
| 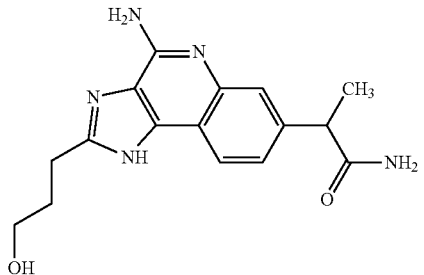 [SMILES: CC(C(N)=O)c1ccc2c(c1)nc(N)c1nc(CCCO)[nH]c12] | 120 | B | D | D | 313.9 |
| 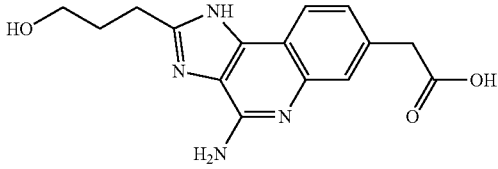 | 121 | B | D | D | 301.1 |
| 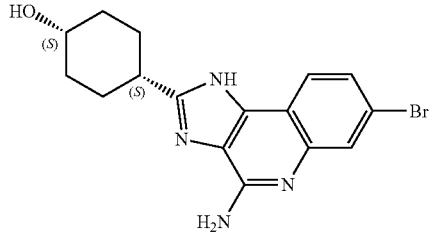 | 122 | B | D | D | 363.2 |
| 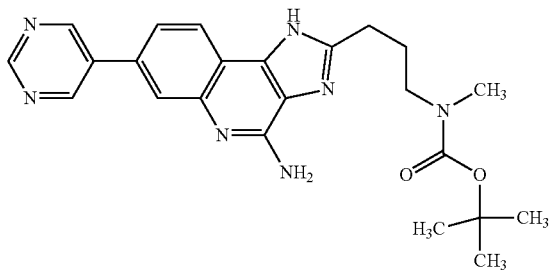 [SMILES: CN(CCCc1nc2c(N)nc3cc(-c4cncnc4)ccc3c2[nH]1)C(=O)OC(C)(C)C] | 123 | B | D | D | 434.2 |
| 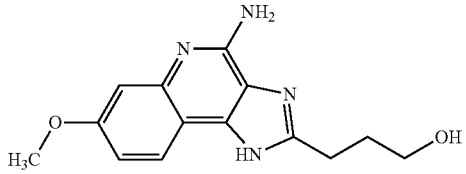 [SMILES: COc1ccc2c(c1)nc(N)c1nc(CCCO)[nH]c12] | 124 | B | D | D | 273.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 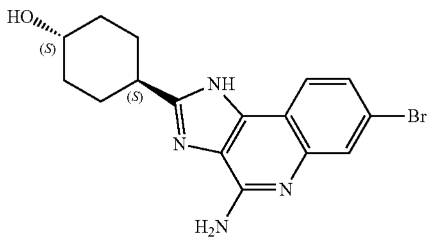 | 125 | B | D | D | 361.2 |
| 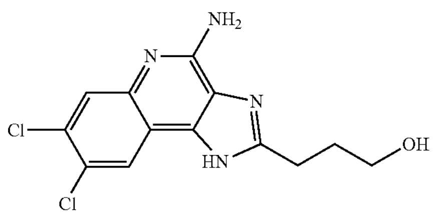 [SMILES: Nc1nc2cc(Cl)c(Cl)cc2c2[nH]c(CCCO)nc12] | 126 | B | D | D | 311.0 |
| 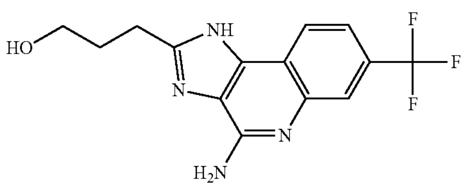 [SMILES: Nc1nc2cc(C(F)(F)F)ccc2c2[nH]c(CCCO)nc12] | 127 | C | C | D | 311.0 |
| 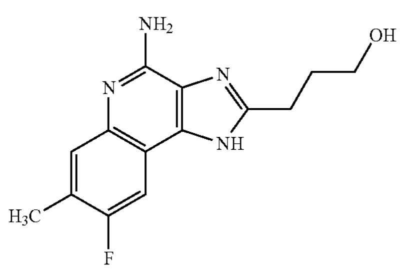 [SMILES: Cc1cc2nc(N)c3nc(CCCO)[nH]c3c2cc1F] | 128 | C | D | C | 275.1 |
| 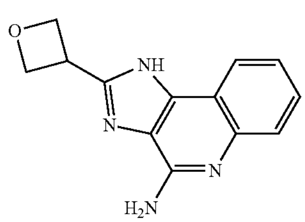 [SMILES: Nc1nc2ccccc2c2[nH]c(C3COC3)nc12] | 129 | C | D | D | 241.1 |
| 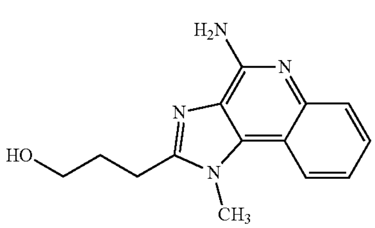 [SMILES: Cn1c(CCCO)nc2c(N)nc3ccccc3c21] | 130 | C | D | D | 257.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 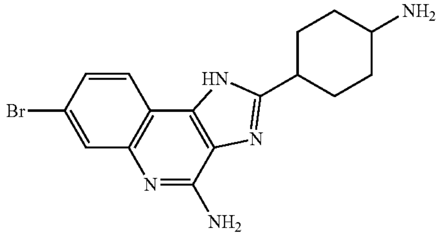 [SMILES: Nc1nc2cc(Br)ccc2c2[nH]c(C3CCC(N)CC3)nc12] | 131 | C | D | C | 362.0 |
| 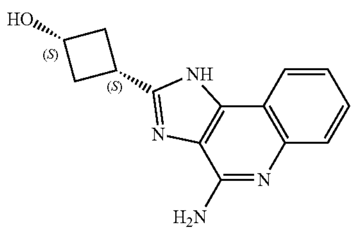 | 132 | C | D | D | 255.1 |
| 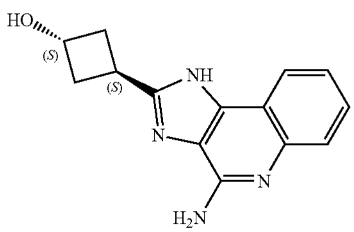 | 133 | C | D | D | 255.1 |
| 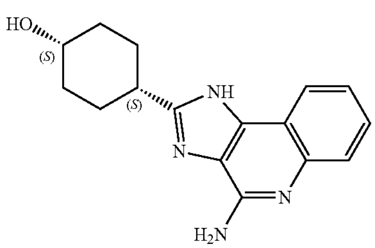 | 134 | C | D | D | 283.3 |
| 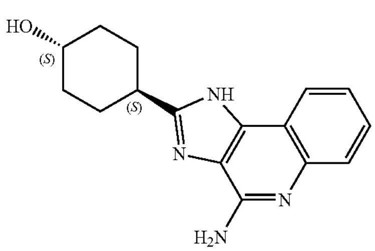 | 135 | C | D | D | 283.2 |
| 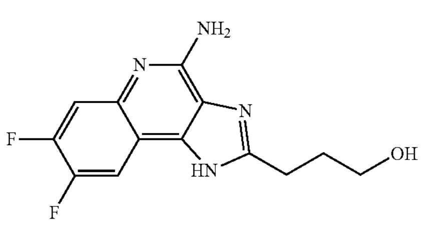 [SMILES: Nc1nc2cc(F)c(F)cc2c2[nH]c(CCCO)nc12] | 136 | C | D | D | 279.1 |

TABLE 2-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 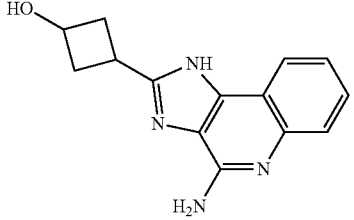 [SMILES: Nc1nc2ccccc2c2[nH]c(C3CC(O)C3)nc12] | 137 | C | D | D | 254.9 |
| 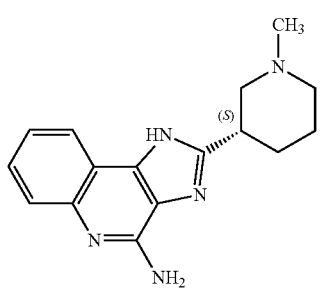 | 138 | C | D | D | 282.0 |
| 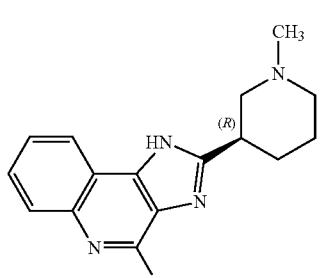 | 139 | C | D | D | 282.0 |
| 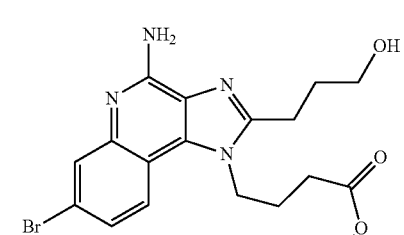 | 141 | B | D | D | 421.1 |
| 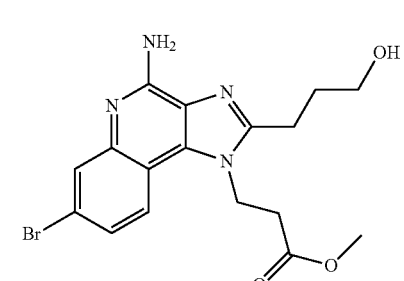 | 142 | B | D | D | 408.9 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
| --- | --- | --- | --- | --- | --- |
| 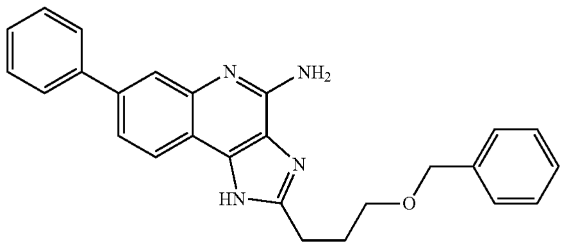 [SMILES: Nc1nc2cc(-c3ccccc3)ccc2c2[nH]c(CCCOCc3ccccc3)nc12] | 144 | | | | 409.2 |
| 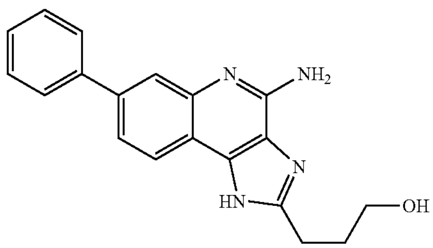 [SMILES: Nc1nc2cc(-c3ccccc3)ccc2c2[nH]c(CCCO)nc12] | 145 | A | D | D | 319.1 |
| 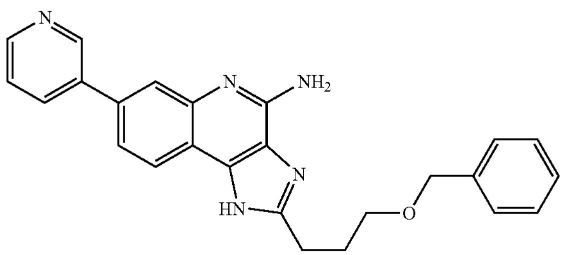 [SMILES: Nc1nc2cc(-c3cccnc3)ccc2c2[nH]c(CCCOCc3ccccc3)nc12] | 146 | C | D | D | 410.2 |
| 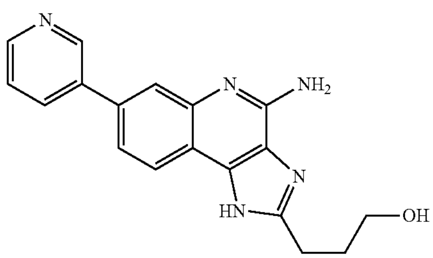 [SMILES: Nc1nc2cc(-c3cccnc3)ccc2c2[nH]c(CCCO)nc12] | 147 | B | D | D | 320.1 |
| 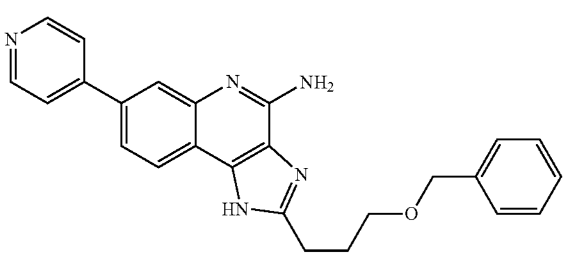 [SMILES: Nc1nc2cc(-c3ccncc3)ccc2c2[nH]c(CCCOCc3ccccc3)nc12] | 148 | C | D | D | 410.2 |
| 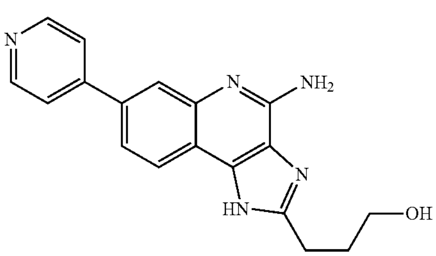 [SMILES: Nc1nc2cc(-c3ccncc3)ccc2c2[nH]c(CCCO)nc12] | 149 | B | D | D | 320.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 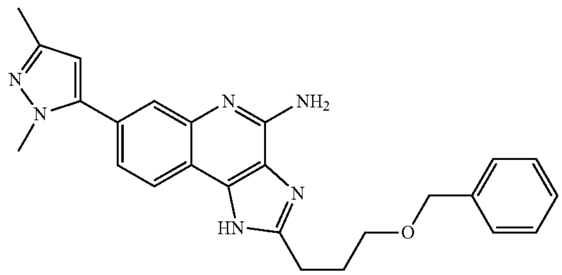 [SMILES: Cc1cc(-c2ccc3c(c2)nc(N)c2nc(CCCOCc4ccccc4)[nH]c23)n(C)n1] | 150 | D | D | D | 427.2 |
| 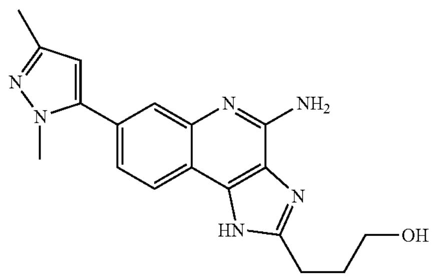 [SMILES: Cc1cc(-c2ccc3c(c2)nc(N)c2nc(CCCO)[nH]c23)n(C)n1] | 151 | B | D | D | 337.2 |
| 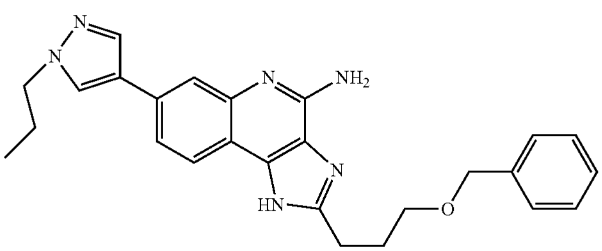 [SMILES: CCCn1cc(-c2ccc3c(c2)nc(N)c2nc(CCCOCc4ccccc4)[nH]c23)cn1] | 152 | C | D | D | 441.2 |
| 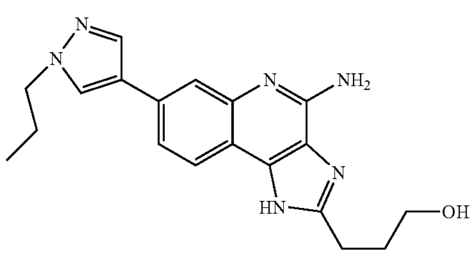 [SMILES: CCCn1cc(-c2ccc3c(c2)nc(N)c2nc(CCCO)[nH]c23)cn1] | 153 | B | D | D | 351.2 |
| 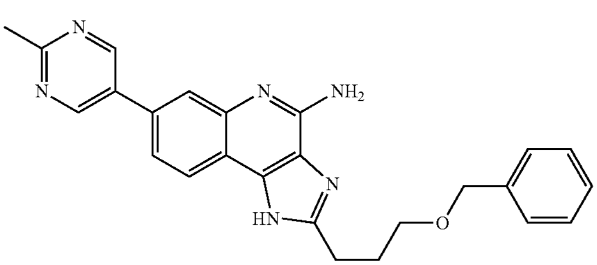 [SMILES: Cc1ncc(-c2ccc3c(c2)nc(N)c2nc(CCCOCc4ccccc4)[nH]c23)cn1] | 154 | B | D | D | 425.2 |

TABLE 2-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 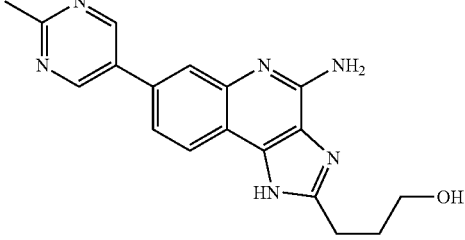 | 155 | B | D | D | 335.1 |
| 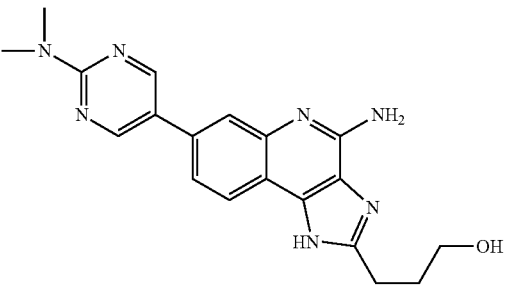 [SMILES: CN(C)c1ncc(-c2ccc3c(c2)nc(N)c2nc(CCCO)[nH]c23)cn1] | 156 | D | D | D | 364.2 |
| 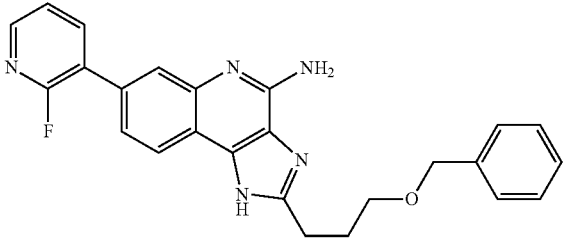 [SMILES: Nc1nc2cc(-c3cccnc3F)ccc2c2[nH]c(CCCOCc3ccccc3)nc12] | 157 | D | D | D | 428.2 |
| 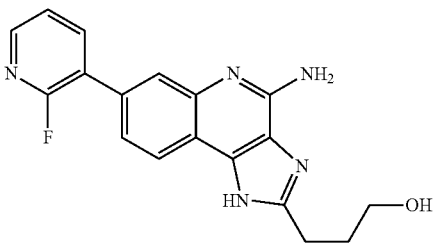 [SMILES: Nc1nc2cc(-c3cccnc3F)ccc2c2[nH]c(CCCO)nc12] | 158 | B | D | D | 338.1 |
| 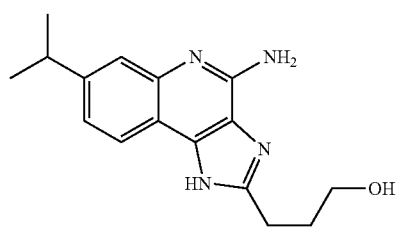 [SMILES: CC(C)c1ccc2c(c1)nc(N)c1nc(CCCO)[nH]c12] | 159 | B | C | D | 285.2 |
| 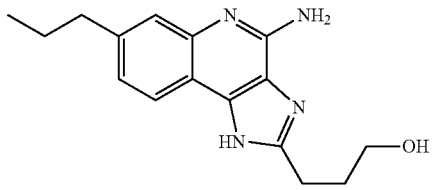 [SMILES: CCCc1ccc2c(c1)nc(N)c1nc(CCCO)[nH]c12] | 160 | A | C | D | 285.2 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 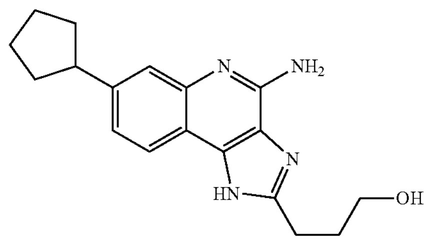 [SMILES: Nc1nc2cc(C3CCCC3)ccc2c2[nH]c(CCCO)nc12] | 161 | A | D | D | 311.2 |
| 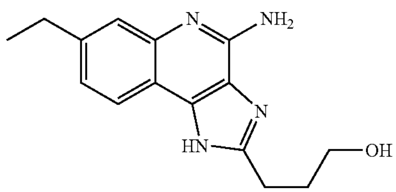 [SMILES: CCc1ccc2c(c1)nc(N)c1nc(CCCO)[nH]c12] | 162 | B | C | C | 271.1 |
| 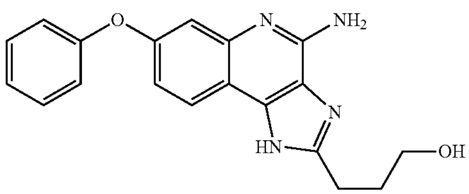 [SMILES: Nc1nc2cc(Oc3ccccc3)ccc2c2[nH]c(CCCO)nc12] | 163 | C | D | D | 335.1 |
| 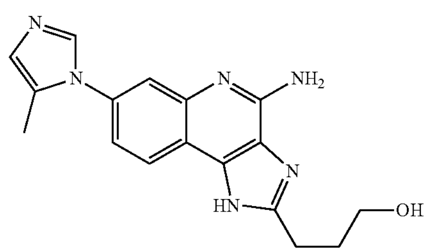 [SMILES: Cc1cncn1-c1ccc2c(c1)nc(N)c1nc(CCCO)[nH]c12] | 164 | D | D | D | 323.1 |
| 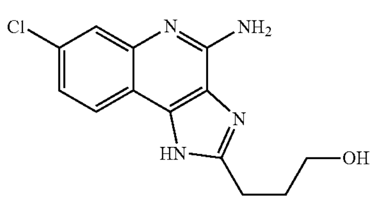 [SMILES: Nc1nc2cc(Cl)ccc2c2[nH]c(CCCO)nc12] | 165 | C | C | C | 277.1 |
| 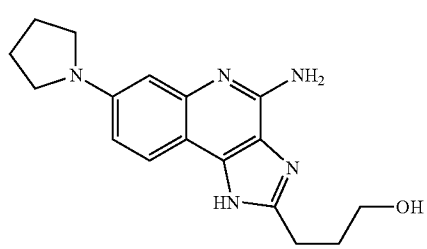 [SMILES: Nc1nc2cc(N3CCCC3)ccc2c2[nH]c(CCCO)nc12] | 166 | D | D | D | 312.2 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 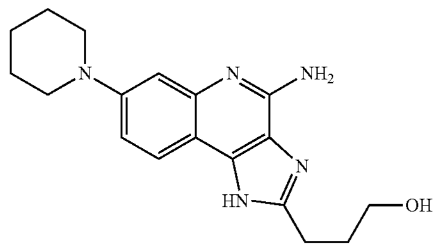 [SMILES: Nc1nc2cc(N3CCCCC3)ccc2c2[nH]c(CCCO)nc12] | 167 | D | D | D | 326.2 |
| 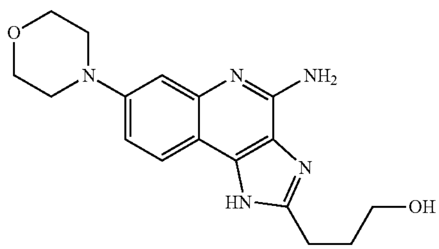 | 168 | D | D | D | 328.2 |
| 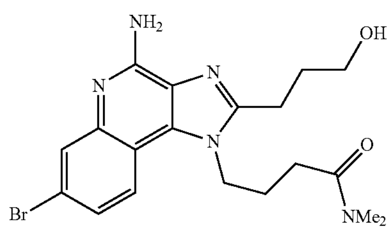 [SMILES: CN(C)C(=O)CCCn1c(CCCO)nc2c(N)nc3cc(Br)ccc3c21] | 169 | B | D | D | |
| 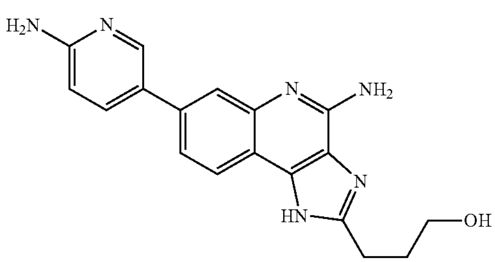 [SMILES: Nc1ccc(-c2ccc3c(c2)nc(N)c2nc(CCCO)[nH]c23)cn1] | 170 | D | D | D | 335.1 |
| 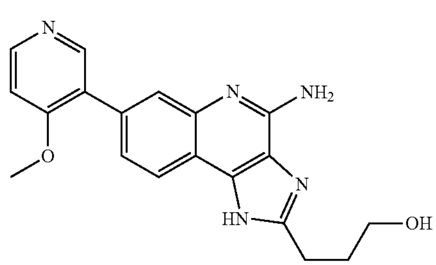 [SMILES: COc1ccncc1-c1ccc2c(c1)nc(N)c1nc(CCCO)[nH]c12] | 171 | D | D | D | 350.1 |
| 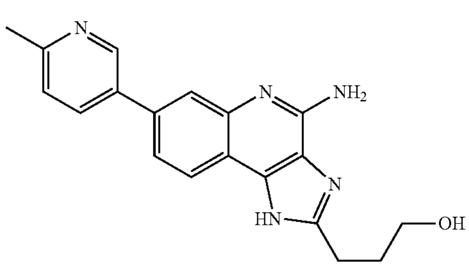 [SMILES: Cc1ccc(-c2ccc3c(c2)nc(N)c2nc(CCCO)[nH]c23)cn1] | 172 | D | D | D | 334.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 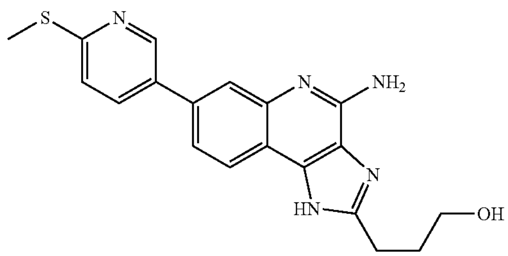 [SMILES: CSc1ccc(-c2ccc3c(c2)nc(N)c2nc(CCCO)[nH]c23)cn1] | 173 | D | D | D | 366.1 |
| 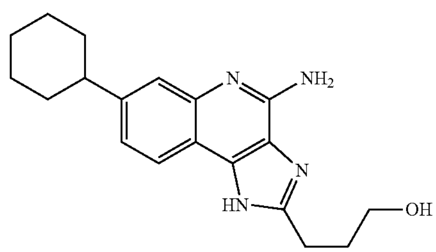 [SMILES: Nc1nc2cc(C3CCCCC3)ccc2c2[nH]c(CCCO)nc12] | 174 | C | D | D | 325.2 |
| 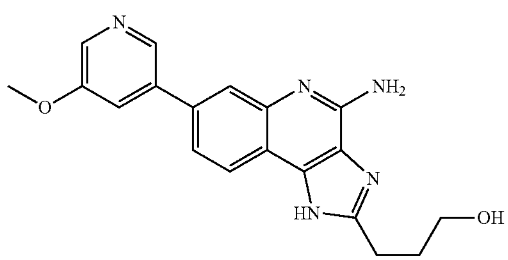 [SMILES: COc1cncc(-c2ccc3c(c2)nc(N)c2nc(CCCO)[nH]c23)c1] | 175 | D | D | D | 350.1 |
| 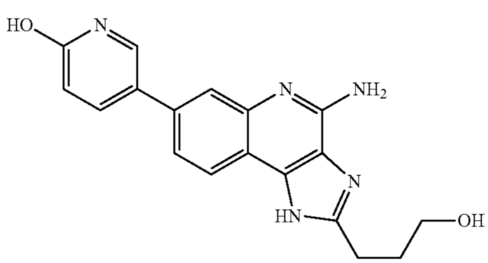 [SMILES: Nc1nc2cc(-c3ccc(O)nc3)ccc2c2[nH]c(CCCO)nc12] | 176 | D | D | D | 336.1 |
| 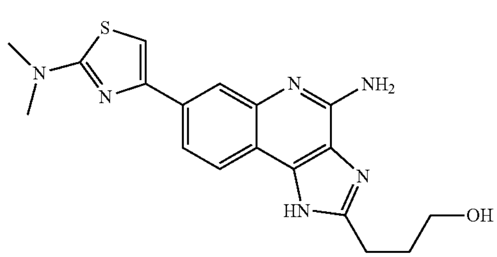 [SMILES: CN(C)c1nc(-c2ccc3c(c2)nc(N)c2nc(CCCO)[nH]c23)cs1] | 177 | D | D | D | 369.1 |
| 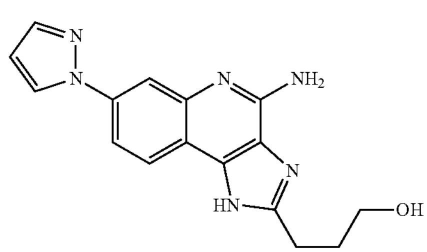 [SMILES: Nc1nc2cc(-n3cccn3)ccc2c2[nH]c(CCCO)nc12] | 178 | A | D | C | 309.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 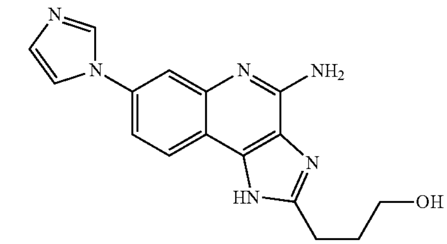 [SMILES: Nc1nc2cc(-n3ccnc3)ccc2c2[nH]c(CCCO)nc12] | 179 | D | D | D | 309.1 |
| 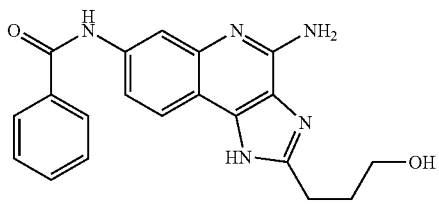 [SMILES: Nc1nc2cc(NC(=O)c3ccccc3)ccc2c2[nH]c(CCCO)nc12] | 180 | D | D | D | 362.1 |
| 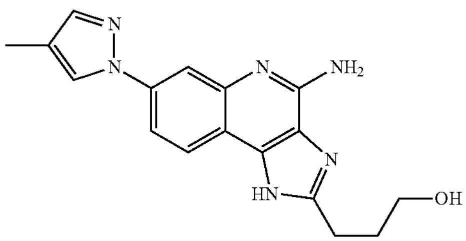 [SMILES: Cc1cnn(-c2ccc3c(c2)nc(N)c2nc(CCCO)[nH]c23)c1] | 181 | B | D | D | 323.1 |
| 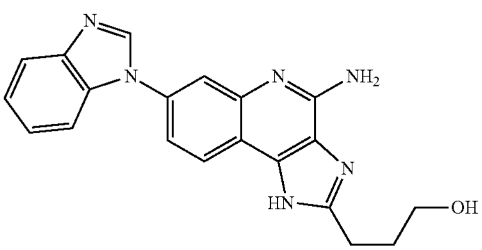 [SMILES: Nc1nc2cc(-n3cnc4ccccc43)ccc2c2[nH]c(CCCO)nc12] | 182 | D | D | D | 359.1 |
| 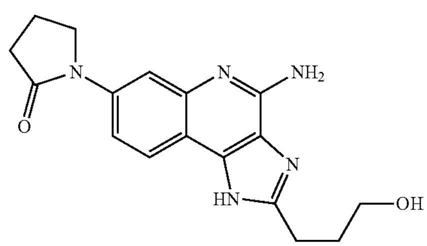 [SMILES: Nc1nc2cc(N3CCCC3=O)ccc2c2[nH]c(CCCO)nc12] | 183 | C | D | D | 326.1 |
| 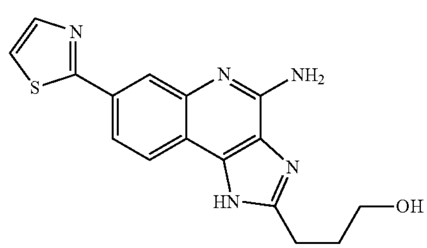 [SMILES: Nc1nc2cc(-c3nccs3)ccc2c2[nH]c(CCCO)nc12] | 184 | D | D | D | 326.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 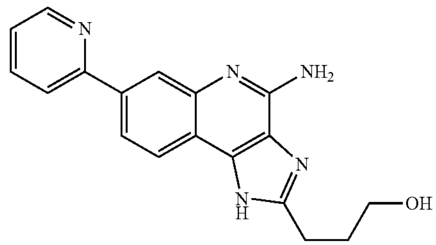 [SMILES: Nc1nc2cc(-c3ccccn3)ccc2c2[nH]c(CCCO)nc12] | 185 | A | D | D | 320.1 |
| 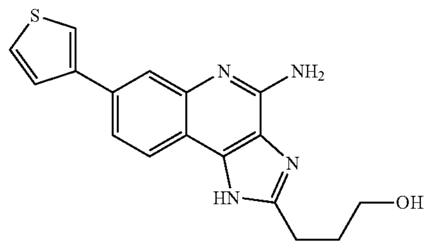 [SMILES: Nc1nc2cc(-c3ccsc3)ccc2c2[nH]c(CCCO)nc12] | 186 | A | D | D | 325.1 |
| 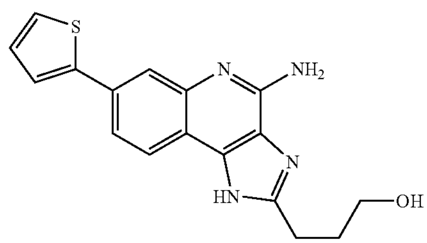 [SMILES: Nc1nc2cc(-c3cccs3)ccc2c2[nH]c(CCCO)nc12] | 187 | A | D | D | 325.1 |
| 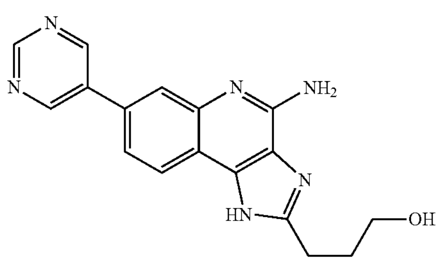 [SMILES: Nc1nc2cc(-c3cncnc3)ccc2c2[nH]c(CCCO)nc12] | 188 | C | D | D | 321.1 |
| 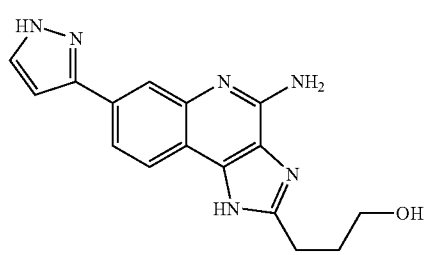 [SMILES: Nc1nc2cc(-c3cc[nH]n3)ccc2c2[nH]c(CCCO)nc12] | 189 | A | D | D | 309.1 |
| 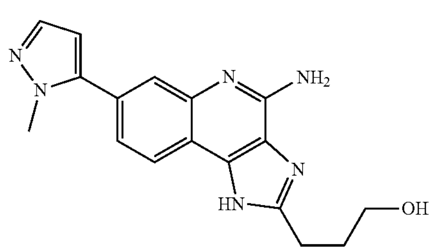 [SMILES: Cn1nccc1-c1ccc2c(c1)nc(N)c1nc(CCCO)[nH]c12] | 190 | C | D | D | 323.1 |

TABLE 2-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 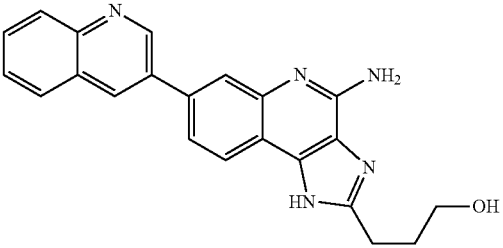 [SMILES: Nc1nc2cc(-c3cnc4ccccc4c3)ccc2c2[nH]c(CCCO)nc12] | 191 | D | D | D | 370.1 |
| 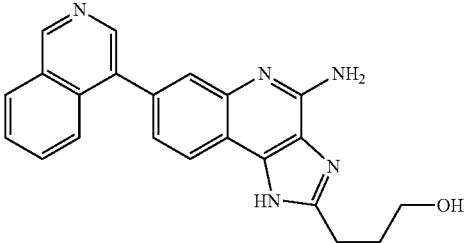 [SMILES: Nc1nc2cc(-c3cncc4ccccc34)ccc2c2[nH]c(CCCO)nc12] | 192 | D | D | D | 370.1 |
| 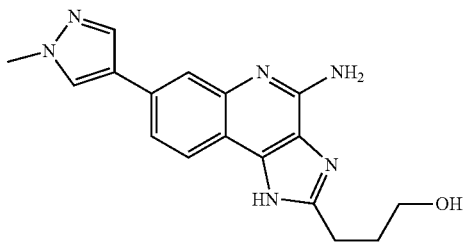 [SMILES: Cn1cc(-c2ccc3c(c2)nc(N)c2nc(CCCO)[nH]c23)cn1] | 193 | C | D | D | 323.1 |
| 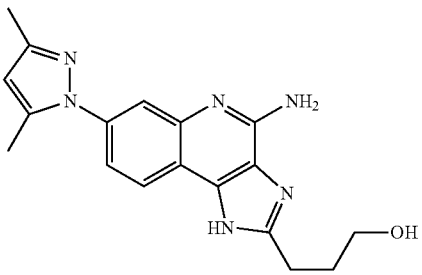 [SMILES: Cc1cc(C)n(-c2ccc3c(c2)nc(N)c2nc(CCCO)[nH]c23)n1] | 194 | C | C | D | 337.2 |
| 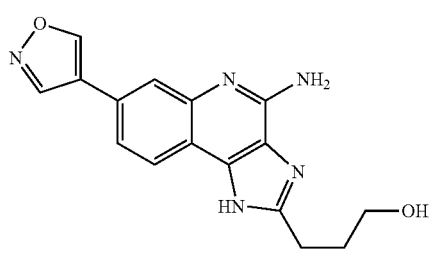 [SMILES: Nc1nc2cc(-c3cnoc3)ccc2c2[nH]c(CCCO)nc12] | 195 | D | D | D | 310.1 |
| 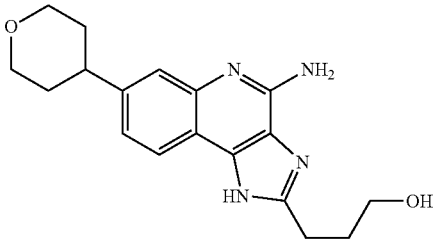 | 196 | D | D | D | 327.2 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 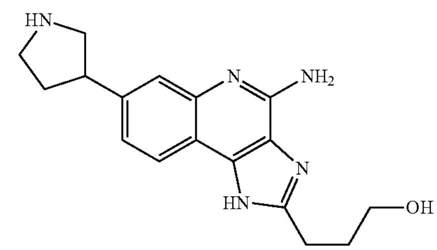 [SMILES: Nc1nc2cc(C3CCNC3)ccc2c2[nH]c(CCCO)nc12] | 197 | D | D | | 312.2 |
| 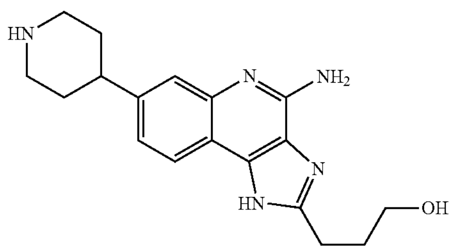 [SMILES: Nc1nc2cc(C3CCNCC3)ccc2c2[nH]c(CCCO)nc12] | 198 | D | D | | 326.2 |
| 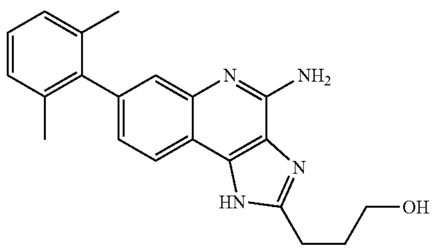 [SMILES: Cc1cccc(C)c1-c1ccc2c(c1)nc(N)c1nc(CCCO)[nH]c12] | 199 | D | D | D | 333.2 |
| 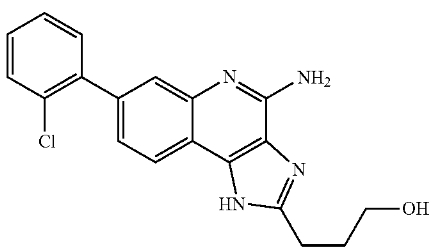 [SMILES: Nc1nc2cc(-c3ccccc3Cl)ccc2c2[nH]c(CCCO)nc12] | 200 | D | D | D | 353.1 |
| 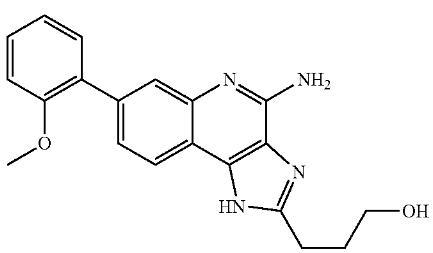 [SMILES: COc1ccccc1-c1ccc2c(c1)nc(N)c1nc(CCCO)[nH]c12] | 201 | D | D | D | 349.1 |
| 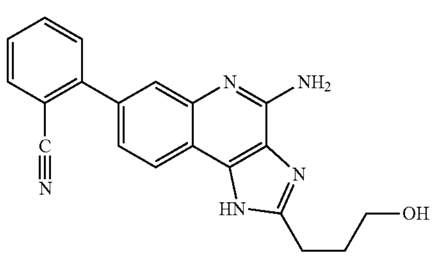 [SMILES: N#Cc1ccccc1-c1ccc2c(c1)nc(N)c1nc(CCCO)[nH]c12] | 202 | D | D | D | 344.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 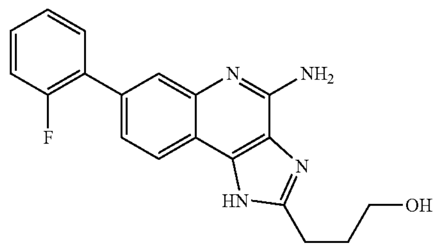 [SMILES: Nc1nc2cc(-c3ccccc3F)ccc2c2[nH]c(CCCO)nc12] | 203 | D | D | D | 337.1 |
| 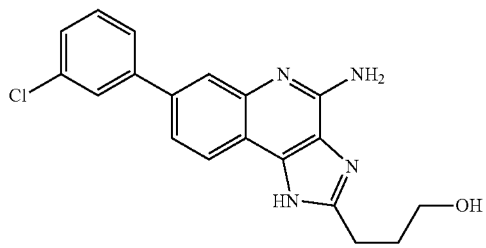 [SMILES: Nc1nc2cc(-c3cccc(Cl)c3)ccc2c2[nH]c(CCCO)nc12] | 204 | D | D | D | 353.1 |
| 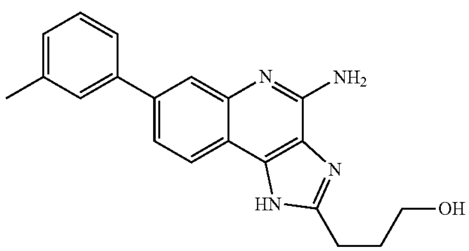 [SMILES: Cc1cccc(-c2ccc3c(c2)nc(N)c2nc(CCCO)[nH]c23)c1] | 205 | C | D | D | 333.2 |
| 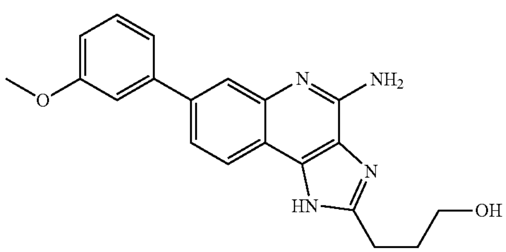 [SMILES: COc1cccc(-c2ccc3c(c2)nc(N)c2nc(CCCO)[nH]c23)c1] | 206 | D | D | D | 349.1 |
| 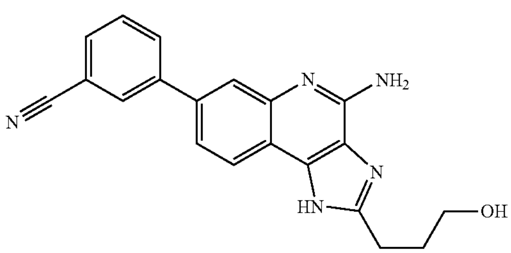 [SMILES: N#Cc1cccc(-c2ccc3c(c2)nc(N)c2nc(CCCO)[nH]c23)c1] | 207 | D | D | D | 344.1 |
| 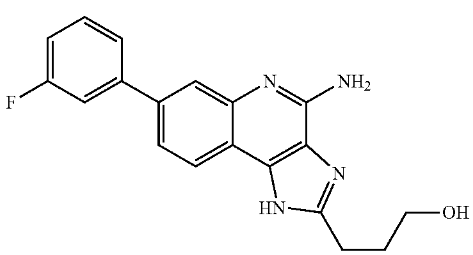 [SMILES: Nc1nc2cc(-c3cccc(F)c3)ccc2c2[nH]c(CCCO)nc12] | 208 | D | D | D | 337.1 |

TABLE 2-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 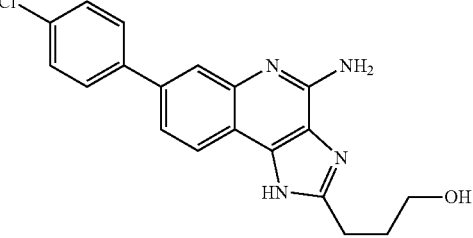 | 209 | D | D | D | 353.1 |
| 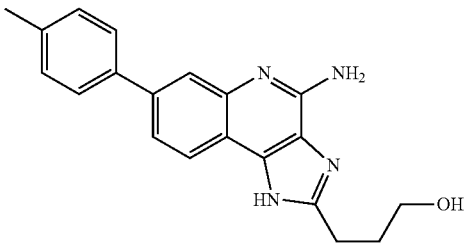 [SMILES: Cc1ccc(-c2ccc3c(c2)nc(N)c2nc(CCCO)[nH]c23)cc1] | 210 | D | D | D | 333.2 |
| 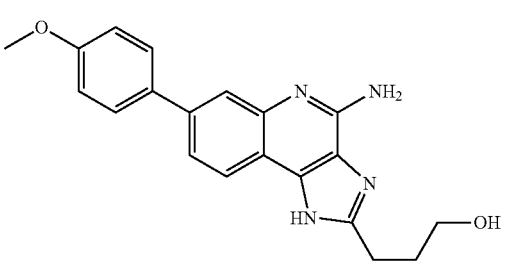 | 211 | D | D | D | 349.1 |
| 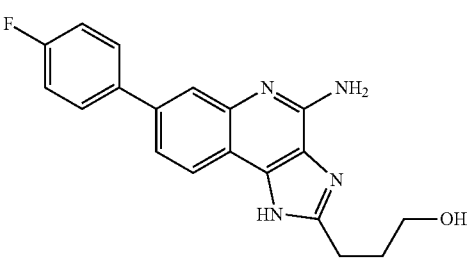 [SMILES: Nc1nc2cc(-c3ccc(F)cc3)ccc2c2[nH]c(CCCO)nc12] | 212 | D | D | C | 337.1 |
| 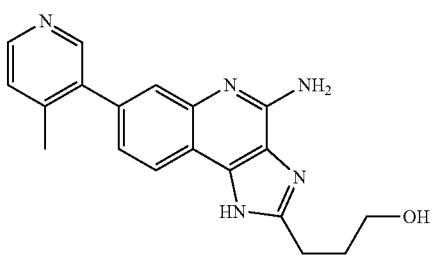 | 213 | D | B | D | 334.1 |
| 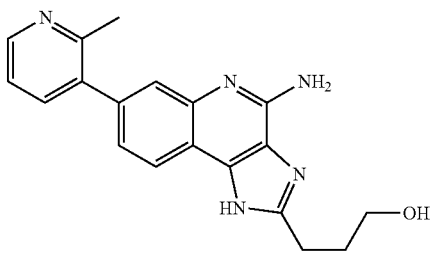 [SMILES: Cc1ncccc1-c1ccc2c(c1)nc(N)c1nc(CCCO)[nH]c12] | 214 | D | C | D | 334.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 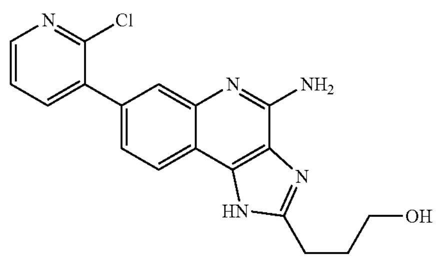 [SMILES: Nc1nc2cc(-c3cccnc3Cl)ccc2c2[nH]c(CCCO)nc12] | 215 | D | C | C | 354.1 |
| 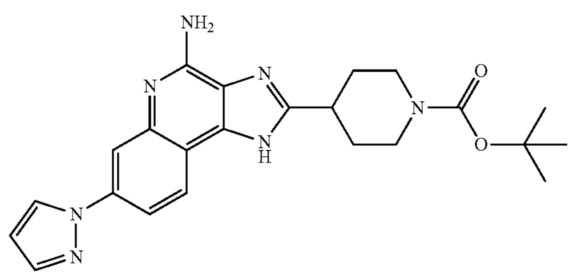 [SMILES: CC(C)(C)OC(=O)N1CCC(c2nc3c(N)nc4cc(-n5cccn5)ccc4c3[nH]2)CC1] | 218 | A | D | D | 434.3 |
| 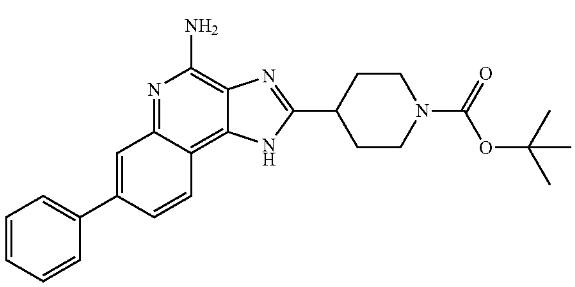 [SMILES: CC(C)(C)OC(=O)N1CCC(c2nc3c(N)nc4cc(-c5ccccc5)ccc4c3[nH]2)CC1] | 219 | A | D | D | 444.3 |
| 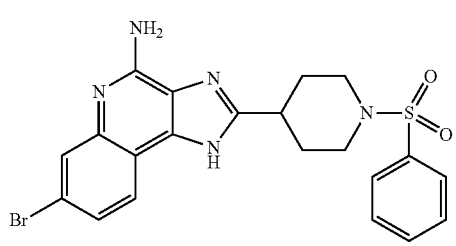 [SMILES: Nc1nc2cc(Br)ccc2c2[nH]c(C3CCN(S(=O)(=O)c4ccccc4)CC3)nc12] | 220 | B | D | D | 488.2 |
| 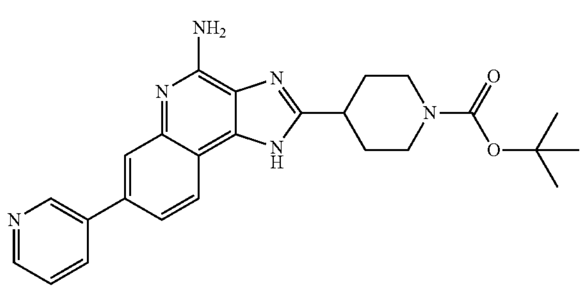 [SMILES: CC(C)(C)OC(=O)N1CCC(c2nc3c(N)nc4cc(-c5cccnc5)ccc4c3[nH]2)CC1] | 221 | B | D | D | 445.3 |

TABLE 2-continued
| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 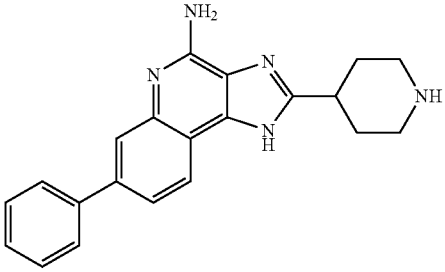 [SMILES: Nc1nc2cc(-c3ccccc3)ccc2c2[nH]c(C3CCNCC3)nc12] | 222 | B | D | D | 344.3 |
| 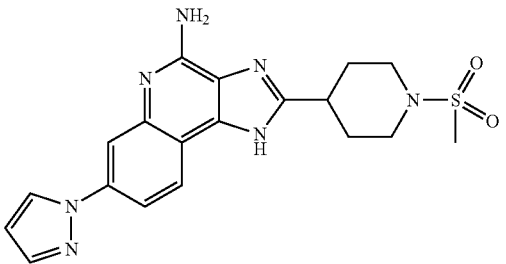 [SMILES: CS(=O)(=O)N1CCC(c2nc3c(N)nc4cc(-n5cccn5)ccc4c3[nH]2)CC1] | 223 | B | D | D | 412.1 |
| 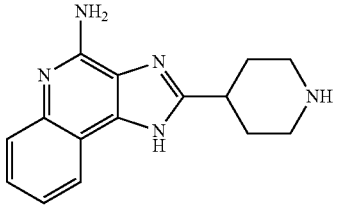 [SMILES: Nc1nc2ccccc2c2[nH]c(C3CCNCC3)nc12] | 224 | C | D | D | 268.2 |
| 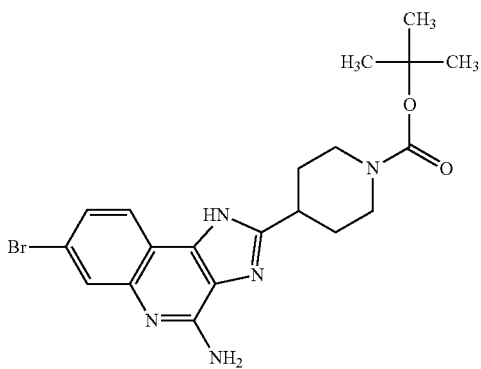 [SMILES: CC(C)(C)OC(=O)N1CCC(c2nc3c(N)nc4cc(Br)ccc4c3[nH]2)CC1] | 225 | B | D | D | 446.1 |
| 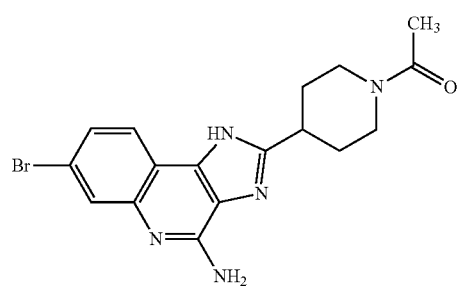 [SMILES: CC(=O)N1CCC(c2nc3c(N)nc4cc(Br)ccc4c3[nH]2)CC1] | 226 | C | D | D | 388.1 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 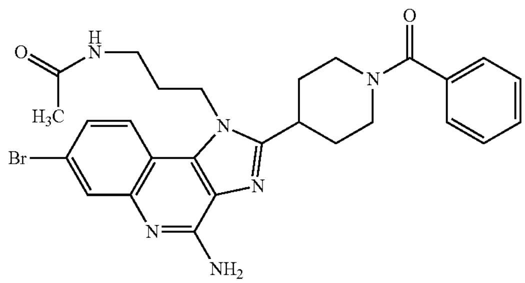 [SMILES: CC(=O)NCCCn1c(C2CCN(C(=O)c3ccccc3)CC2)nc2c(N)nc3cc(Br)ccc3c21] | 227 | C | D | D | 551.3 |
| 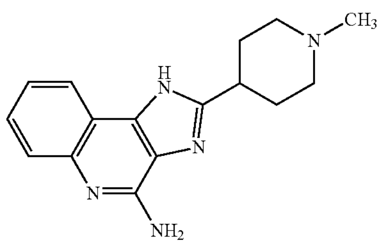 [SMILES: CN1CCC(c2nc3c(N)nc4ccccc4c3[nH]2)CC1] | 228 | C | D | D | 282.1 |
| 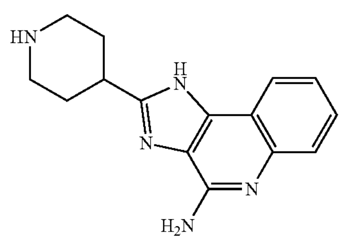 [SMILES: Nc1nc2ccccc2c2[nH]c(C3CCNCC3)nc12] | 229 | C | D | D | 348.1 |
| 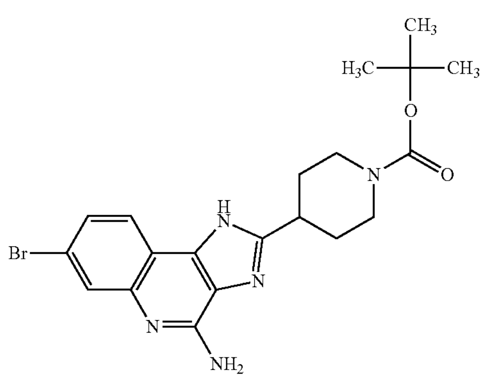 [SMILES: CC(C)(C)OC(=O)N1CCC(c2nc3c(N)nc4cc(Br)ccc4c3[nH]2)CC1] | 230 | B | D | D | 446.1 |
| 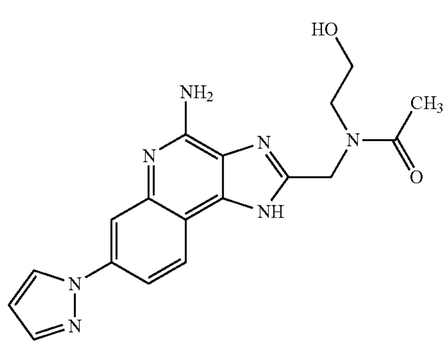 [SMILES: CC(=O)N(CCO)Cc1nc2c(N)nc3cc(-n4cccn4)ccc3c2[nH]1] | 231 | B | | | 366.0 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 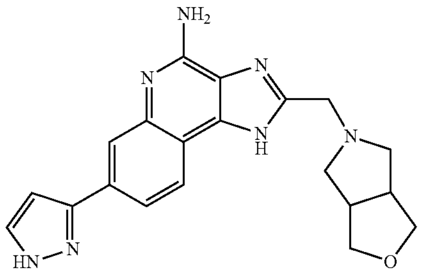 [SMILES: Nc1nc2cc(-c3cc[nH]n3)ccc2c2[nH]c(CN3CC4COCC4C3)nc12] | 232 | B | D | D | 376.2 |
| 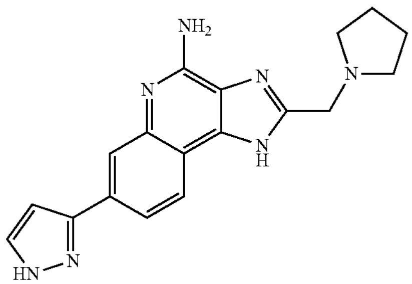 [SMILES: Nc1nc2cc(-c3cc[nH]n3)ccc2c2[nH]c(CN3CCCC3)nc12] | 233 | A | D | D | 334.3 |
| 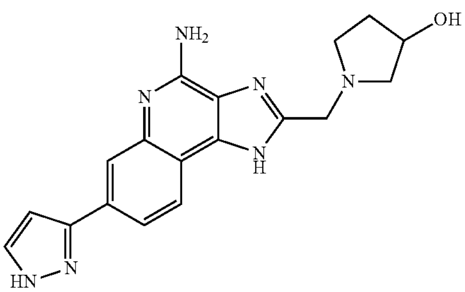 [SMILES: Nc1nc2cc(-c3cc[nH]n3)ccc2c2[nH]c(CN3CCC(O)C3)nc12] | 234 | | | | |
| 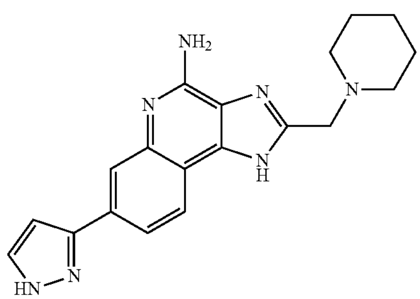 [SMILES: Nc1nc2cc(-c3cc[nH]n3)ccc2c2[nH]c(CN3CCCCC3)nc12] | 235 | | | | |
| 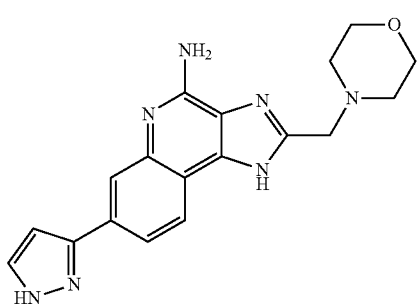 [SMILES: Nc1nc2cc(-c3cc[nH]n3)ccc2c2[nH]c(CN3CCOCC3)nc12] | 236 | | | | |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 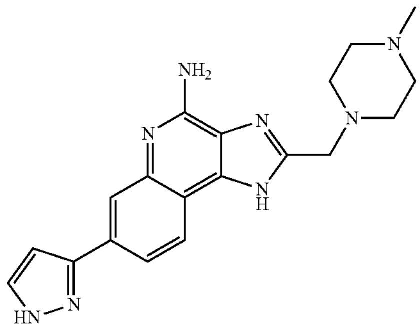 [SMILES: CN1CCN(Cc2nc3c(N)nc4cc(-c5cc[nH]n5)ccc4c3[nH]2)CC1] | 237 | | | | |
| 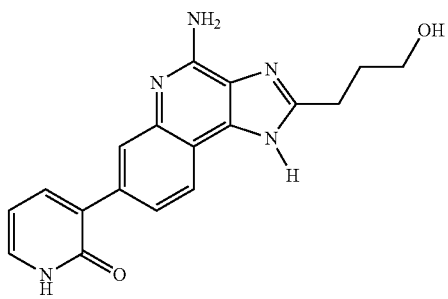 [SMILES: Nc1nc2cc(-c3ccc[nH]c3=O)ccc2c2[nH]c(CCCO)nc12] | 238 | B | D | D | 336.3 |
| 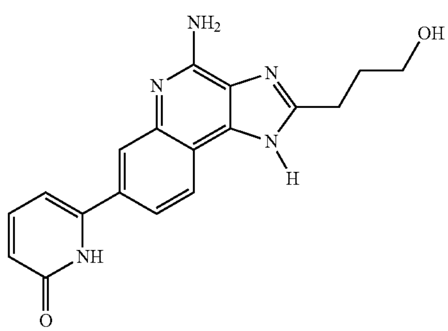 [SMILES: Nc1nc2cc(-c3cccc(=O)[nH]3)ccc2c2[nH]c(CCCO)nc12] | 239 | B | D | D | 336.1 |
| 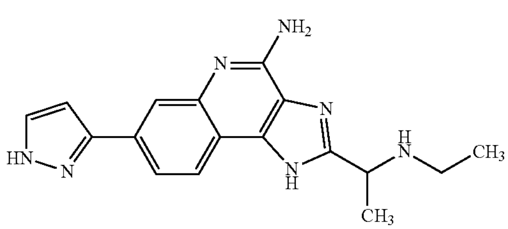 [SMILES: CCNC(C)c1nc2c(N)nc3cc(-c4cc[nH]n4)ccc3c2[nH]1] | 240 | B | D | D | |
| 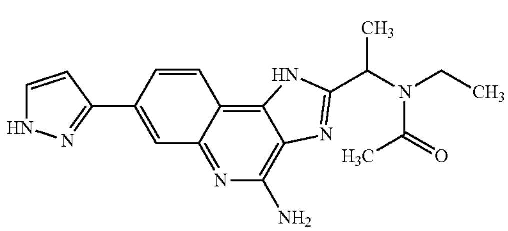 [SMILES: CCN(C(C)=O)C(C)c1nc2c(N)nc3cc(-c4cc[nH]n4)ccc3c2[nH]1] | 241 | B | D | D | |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| 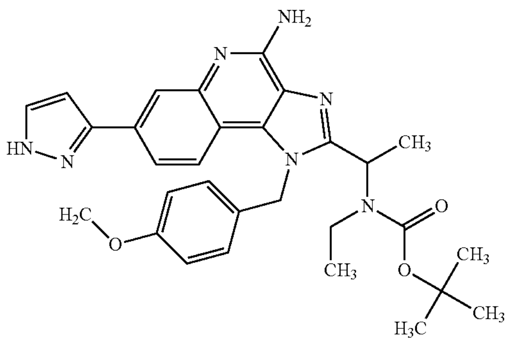 [SMILES: CCN(C(=O)OC(C)(C)C)C(C)c1nc2c(N)nc3cc(-c4cc[nH]n4)ccc3c2n1Cc1ccc(OC)cc1] | 242 | B | D | D | |
| 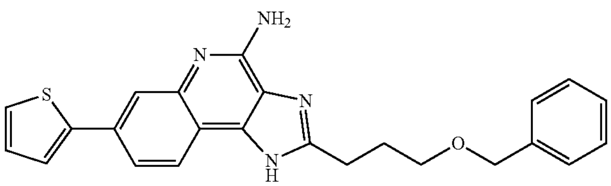 [SMILES: Nc1nc2cc(-c3cccs3)ccc2c2[nH]c(CCCOCc3ccccc3)nc12] | 243 | B | | | 415.2 |
| 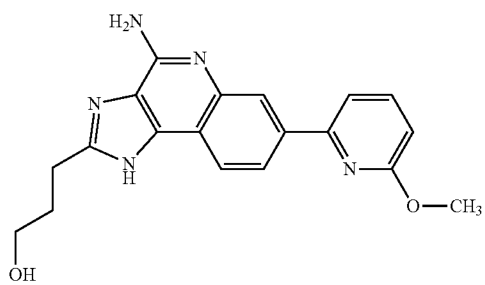 [SMILES: COc1cccc(-c2ccc3c(c2)nc(N)c2nc(CCCO)[nH]c23)n1] | 246 | B | D | D | 350.3 |
| 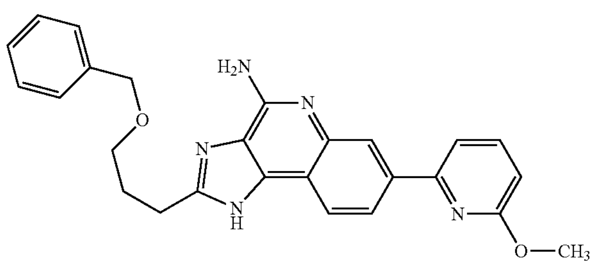 [SMILES: COc1cccc(-c2ccc3c(c2)nc(N)c2nc(CCCOCc4ccccc4)[nH]c23)n1] | 247 | B | D | D | 440.1 |
| 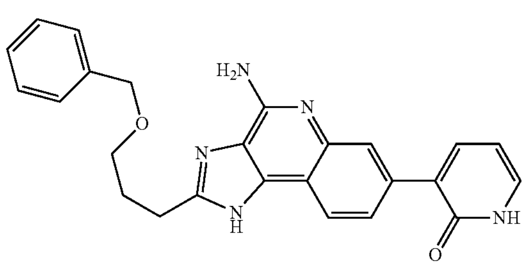 [SMILES: Nc1nc2cc(-c3ccc[nH]c3=O)ccc2c2[nH]c(CCCOCc3ccccc3)nc12] | 249 | B | D | D | 426.4 |

TABLE 2-continued

| Structure | Compound | hNLRP3 Agonist EC$_{50}$ (μM) | TLR7 EC$_{50}$ (μM) | TLR8 EC$_{50}$ (μM) | LCMS [M + H]+ |
|---|---|---|---|---|---|
| (structure) | 251 | B | D | D | 336.1 |
| (structure) | 252 | B | D | D | 556.6 |
| (structure) | 253 | B | D | D | 378.4 | and pharmaceutically acceptable salts thereof.

Pharmaceutical compositions and Administration

General

In some embodiments, a chemical entity (e.g., a compound that modulates (e.g., agonizes or partially agonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%.

Actual methods of preparing such dosage forms are known, or will be apparent, to those skilled in this art; for example, see *Remington: The Science and Practice of Pharmacy*, 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP3 activity (e.g., a decrease, e.g., repressed or impaired NLRP3 signaling) contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In any of the methods described herein, the subject can have an infectious disease. In some examples of any of the methods described herein, the subject has been identified as having an infectious disease, or has been diagnosed as having an infectious disease. For example, an infectious disease can be caused by a bacterium, virus, fungus, parasite, or a mycobacterium.

Non-limiting examples of infectious disease include: *Acinobacter* infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, *Burkholderi* infection, Buruli ulcer, *Calicivirus* infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, *Desmodesmus* infection, deintamoebiasis, diphtheria, diphyllobothriasis, dracunculiasis, ebola hemorrhagic fever, echinococcosis, ehrlichiosis, enterobiasis, *Enterococcus* infection, *Enterovirus* infection, epidemic typhus, erythema infection, exanthema subitum, fasciolopsiasis, fasciolosis, fatal familial insomnia, filariasis, food poisoning by *Clostridium myonecrosis*, free-living amebic infection, *Fusobacterium* infection, gas gangrene, geotrichosis, Gerstmann-Sträussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, *Kingella kingae* infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea versicolor, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional chemotherapeutic agent is an immunomodulatory moiety, e.g., an immune checkpoint inhibitor. In certain of these embodiments, the immune checkpoint inhibitor targets an immune checkpoint receptor selected from the group consisting of CTLA-4, PD-1, PD-L1, PD-1—PD-L1, PD-1—PD-L2, T cell immunoglobulin and mucin 3 (TIM3 or HAVCR2), Galectin 9—TIM3, Phosphatidylserine—TIM3, lymphocyte activation gene 3 protein (LAG3), MHC class II—LAG3, 4-1BB-4-1BB ligand, OX40-OX40 ligand, GITR, GITR ligand—GITR, CD27, CD70-CD27, TNFRSF25, TNFRSF25-TL1A, CD40L, CD4-CD40 ligand, HVEM-LIGHT-LTA, HVEM, HVEM—BTLA, HVEM—CD160, HVEM—LIGHT, HVEM-BTLA-CD160, CD80, CD80—PDL-1, PDL2—CD80, CD244, CD48—CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86—CD28, CD86—CTLA, CD80—CD28, Phosphatidylserine, TIM3, Phosphatidylserine—TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12. See, e.g., Postow, M. *J. Clin. Oncol.* 2015, 33, 1.

In certain of these embodiments, the immune checkpoint inhibitor is selected from the group consisting of: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS-986016, MGA271, Lirilumab, IPH2201, Emactuzumab, INCB024360, Galunisertib, Ulocuplumab, BKT140, Bavituximab, CC-90002, Bevacizumab, and MNRP1685A, and MGA271.

In certain embodiments, the additional chemotherapeutic agent is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., —OCH$_3$ or replacement, e.g., —F or N$_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semisynthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an antimetabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. Vinca alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited, to Taxol, Paclitaxel and/or Docetaxel. In a further embodiment a plant alkaloid or terpernoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butyl-amide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafur-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613, which is incorporated herein by reference in its entirety.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity.

By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the chemical entities, methods, and compositions described herein can be administered to certain treatment-resistant patient populations (e.g., patients resistant to checkpoint inhibitors).

EXAMPLES

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224, the contents of each of which are hereby incorporated by reference in their entirety. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fiesers Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

The following abbreviations have the indicated meanings:
ACN=acetonitrile
$CH_2Cl_2$=dichloromethane
$CH_3ReO_3$=methyltrioxorhenium
d=doublet
DCM=dichloromethane
DIEA=N,N-diethylisopropylamine
DMF=N,N-dimethylformamide
DMSO=dimethylsulfoxide
ES=electrospray ionization
EtOAc=ethyl acetate
EtOH=ethanol
equiv=equivalents
g=grams
h=hours
HCl=hydrogen chloride (usually as a solution)
$H_2O$=water
$H_2O_2$=hydrogen peroxide
HATU=1-[Bis(dimethylamino)methylene]-1H-1,2,3-triazolo[4,5-b]pyridinium 3-oxide hexafluorophosphate
HPLC=high-performance liquid chromatography
$K_2CO_3$=potassium carbonate
LC/MS=liquid chromatography mass spectrometer
$LiBH_4$=lithium borohydride
m=multiplet
M=molar
m-CPBA=meta-chloroperoxybenzoic acid
mg=milligram(s)
MeOH=methanol
MHz=megahertz
mL=milliliter(s)

mmol=millimole(s)
NaHCO₃=sodium hydrogen carbonate
Na₂CO₃=sodium carbonate
NaOH=sodium hydroxide
Na₂SO₄=sodium sulfate
NEt₃=trimethylamine
NH₄OH or NH₃H₂O=ammonium hydroxide
NH₄HCO₃=ammonium hydrogen carbonate
nm=nanometer
PdCl₂(PPh₃)₂=bis(triphenylphosphine)palladium (II) dichloride
Pd(dppf)Cl₂=1,1'-Bis(diphenylphosphino)ferrocene
PMB=para-methoxybenzyl
POCl₃=phosphorous oxychloride
ppm=parts per million
s=singlet
t=triplet
TFA=trifluoroacetic acid
TLC=thin layer chromatography
TsCl=para-toluenesulfonyl chloride
° C.=degrees Celsius
μmol=micromolar Schemes 1 and 2 show examples of methods of preparation of compounds disclosed herein:

Scheme 1.

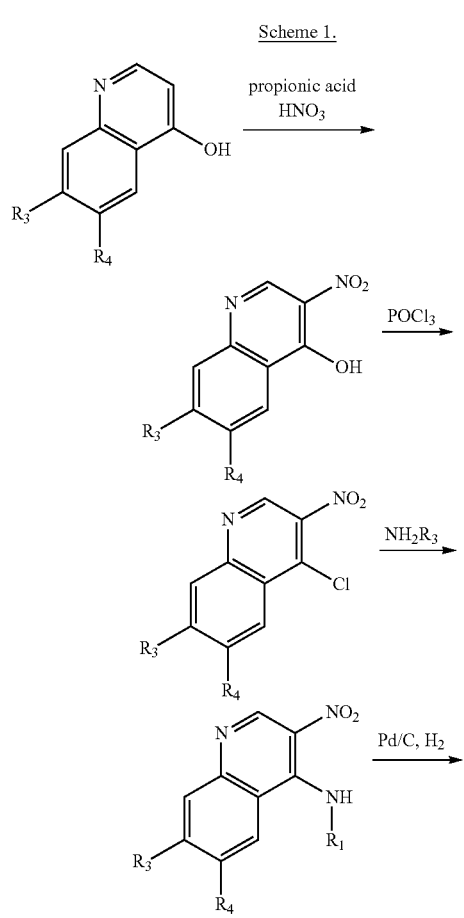

-continued

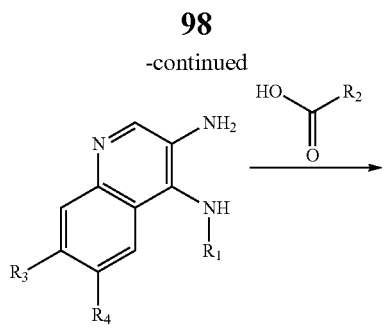

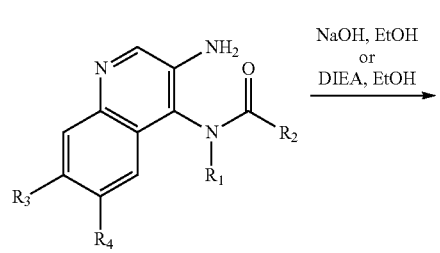

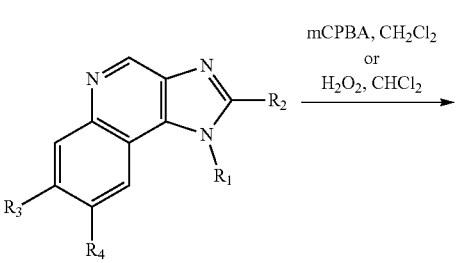

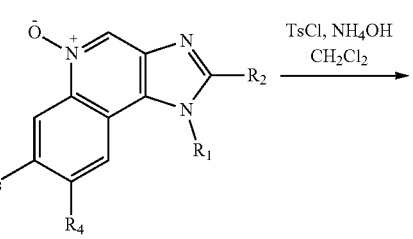

Scheme 2.

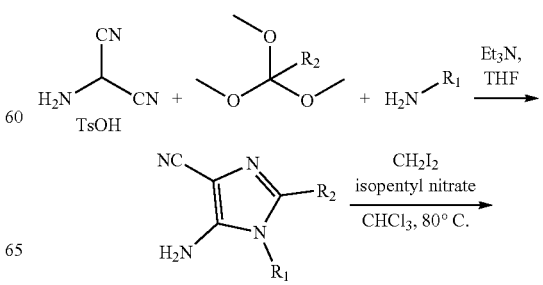

-continued

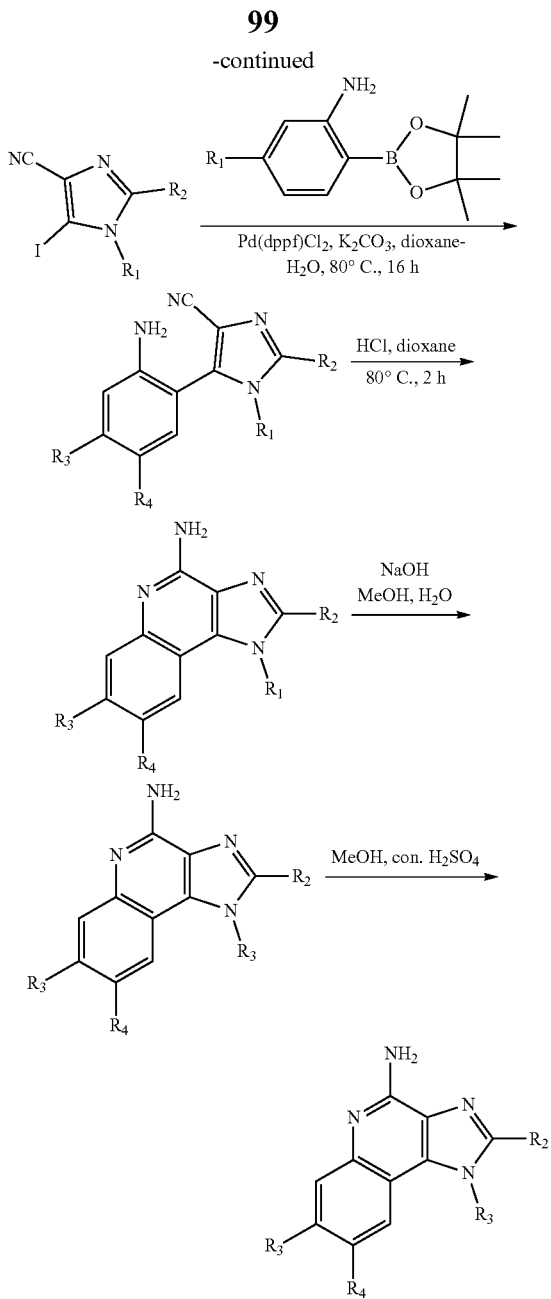

Representative Preparative Examples

Preparative Example 1—Compound 101

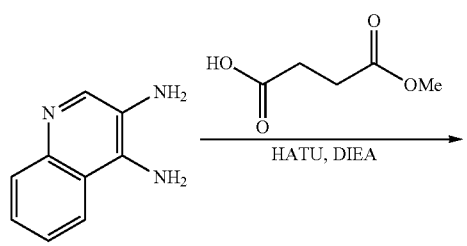

-continued

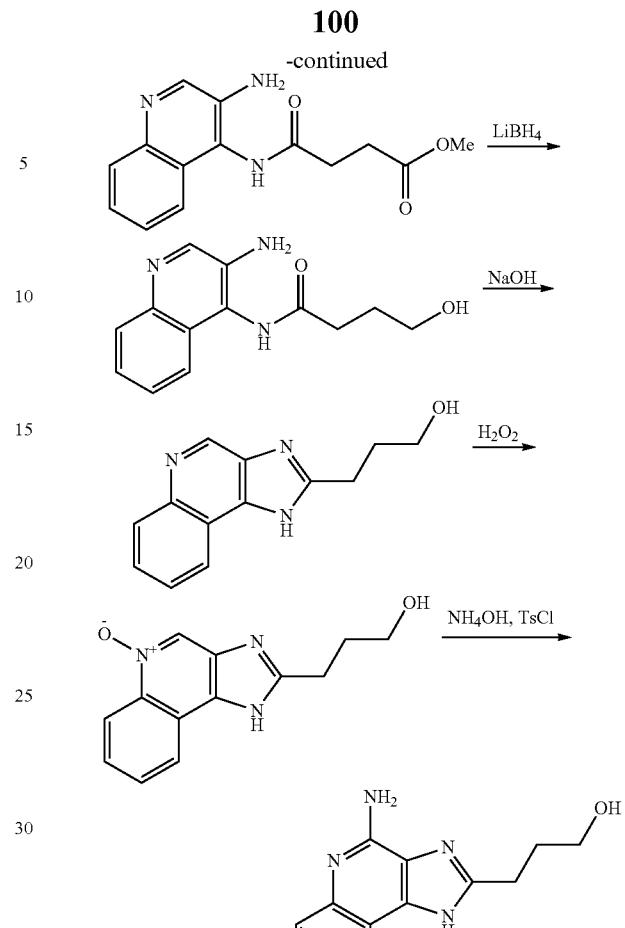

1. Synthesis of Methyl 3-[(3-aminoquinolin-4-yl) carbamoyl]propanoate

Into a 250-mL round-bottom flask purged and maintained with an inert atmosphere of nitrogen, was placed a solution of 4-methoxy-4-oxobutanoic acid (1.98 g, 15.00 mmol, 1.00 equiv), DIEA (2.9 g, 22.50 mmol, 1.50 equiv) and HATU (8.55 g, 22.50 mmol, 1.50 equiv) in N,N-dimethylformamide (50 mL). The resulting solution was stirred for 1.5 h at 0° C. in a water and ice bath. Then to the mixture was added a solution of quinoline-3,4-diamine (2.385 g, 15.00 mmol, 1.00 equiv) in N,N-dimethylformamide (5 mL). The resulting solution was allowed to stir for an additional 4 h at room temperature. The resulting solution was diluted with 100 mL of DCM. The solids were collected by filtration and dried in an oven under reduced pressure. This resulted in 2.139 g (62%) of methyl 3-[(3-aminoquinolin-4-yl)carbamoyl]propanoate as a white solid.

LC-MS-PH-IFM-2-022-5: (ES, m/z): [M+H]$^+$=274.1

2. Synthesis of N-(3-aminoquinolin-4-yl)-4-hydrozybutanamide

Into a 100-mL round-bottom flask, was placed a solution of methyl 3-[(3-aminoquinolin-4-yl)carbamoyl]propanoate (2.139 g, 7.83 mmol, 1.00 equiv) in tetrahydrofuran (50 mL). To the solution was added LiBH$_4$ (259 mg, 11.75 mmol, 1.50 equiv). The resulting solution was stirred for 3 h at room temperature. The reaction was then quenched by the addition of brine. The resulting solution was extracted with dichloromethane and the combined organic layers were concentrated under vacuum. The residue was loaded on a silica gel column with dichloromethane/methanol (30:1) and chromatographed. This resulted in 1.674 g (87%) of N-(3-aminoquinolin-4-yl)-4-hydroxybutanamide as a light yellow solid.

LC-MS-PH-IFM-2-022-7: (ES, m/z): [M+H]⁺=246.1

3. Synthesis of 3-[1H-imidazo[4,5-c]quinolin-2-yl]propan-1-ol

Into a 100-mL round-bottom flask, was placed a solution of N-(3-aminoquinolin-4-yl)-4-hydroxybutanamide (1.674 g, 6.82 mmol, 1.00 equiv) in ethanol/H₂O (55 mL, 10:1). To the solution was added NaOH (2.733 g, 68.33 mmol, 10.00 equiv). The resulting solution was stirred overnight at 80° C. in an oil bath. The resulting solution was concentrated under vacuum and the residue was loaded on a silica gel column with dichloromethane/methanol (30:1) and chromatographed. This resulted in 935 mg (60%) of 3-[1H-imidazo[4,5-c]quinolin-2-yl]propan-1-ol as a light yellow solid.

LC-MS-PH-IFM-2-022-11: (ES, m/z): [M+H]⁺=228.1

4. Synthesis of 2-(3-hydroxypropyl)-1H-imidazo[4,5-c]quinolin-5-ium-5-olate

Into a 50-mL round-bottom flask, was placed a solution of 3-[1H-imidazo[4,5-c]quinolin-2-yl]propan-1-ol (340 g, 1.50 mol, 1.00 equiv) in dichloromethane (5 mL). To the solution were added H₂O₂ (5 mL) and CH₃ReO₃ (50 mg, 0.20 mmol). The resulting solution was stirred for 1 h at room temperature. The reaction was then quenched by the addition of aqueous sodium bicarbonate. The resulting mixture was concentrated under vacuum. The residue was applied onto a silica gel column with dichloromethane/methanol (20:1) and chromatographed. This resulted in 300 mg of 2-(3-hydroxypropyl)-1H-imidazo[4,5-c]quinolin-5-ium-5-olate as a light yellow solid.

LC-MS-PH-IFM-2-022-12: (ES, m/z): [M+H]⁺=244.1

5. Synthesis of 3-[4-amino-1H-imidazo[4,5-c]quinolin-2-yl]propan-1-ol (Compound 101)

Into a 50-mL round-bottom flask, was placed a solution of 2-(3-hydroxypropyl)-1H-imidazo[4,5-c]quinolin-5-ium-5-olate (666 mg, 2.74 mmol, 1.00 equiv) in dichloromethane (8 mL). To the solution were added TsCl (781 mg, 4.11 mmol, 1.50 equiv) and NH₃H₂O (8 mL). The resulting solution was stirred for 1 day at room temperature. After removing the solvent, the crude product was purified by preparative HPLC with the following conditions (Prep_H-PLC_17): Column, X Bridge C18 OBD Prep Column, 10 μm, 19 mm×250 mm; mobile phase, Water (10 MMOL/L NH₄HCO₃) and ACN (8.0% ACN up to 16.0% in 15 min); Detector, UV 254/220 nm. This resulted in 103.7 mg (16%) of 3-[4-amino-1H-imidazo[4,5-c]quinolin-2-yl]propan-1-ol as a white solid.

LC-MS-PH-IFM-2-022-0: (ES, m/z): [M+H]⁺=243.1

H-NMR-PH-IFM-2-022-0: (CD₃OD, 300 MHz, ppm): δ 7.98-7.95 (m, 1H), 7.63-7.60 (m, 1H), 7.47-7.41 (m, 1H), 7.30-7.25 (m, 1H), 3.67-3.61 (m, 2H), 3.06-2.96 (m, 2H), 2.12-2.01 (m, 2H).

Preparative Example 2—Compound 102

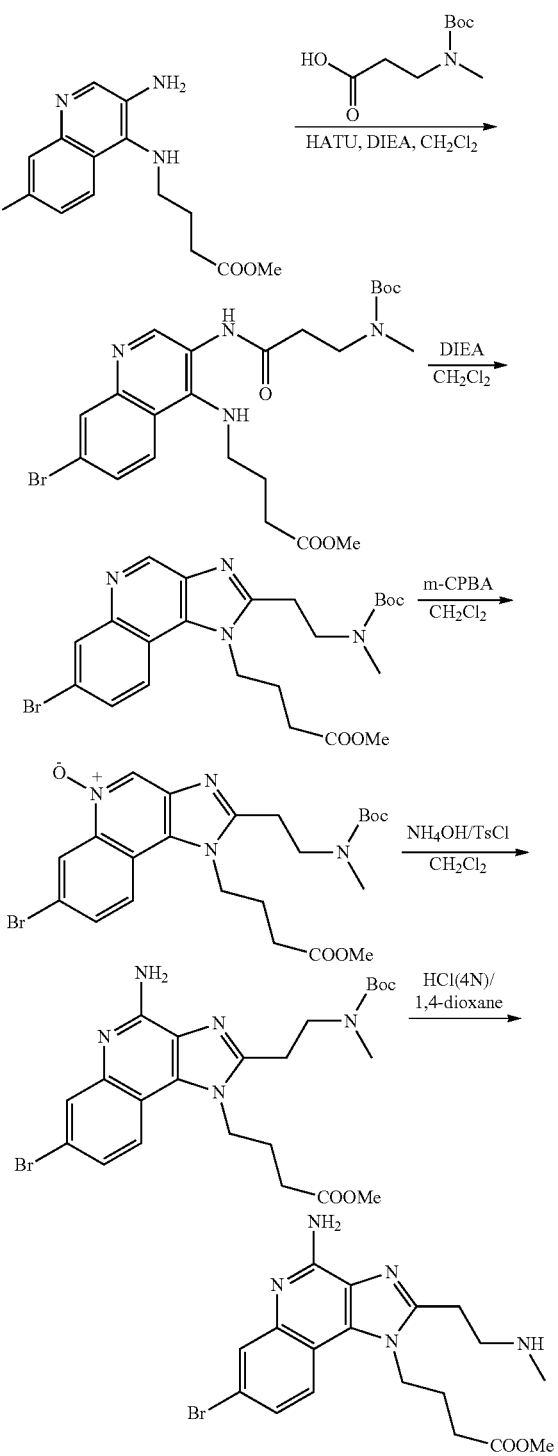

1. Synthesis of Methyl 4-[[7-bromo-3-(3-[[(tert-butoxy)carbonyl](methyl)amino]propanamido)quinolin-4-yl]amino]butanoate Into a 100-mL round-bottom flask, was placed a solution of methyl 4-[(3-amino-7-bromoquinolin-4-yl)amino]butanoate (900 mg, 2.66 mmol, 1.00 equiv) in dichloromethane (50 mL). To the solution were added 3-[[(tert-butoxy)carbonyl](methyl)amino]propanoic acid (650 mg, 3.20 mmol, 1.20 equiv), HATU (3 g, 7.89 mmol, 3.00 equiv) and DIEA (1.7 g, 13.15 mmol, 5.00 equiv). The resulting solution was stirred overnight at room temperature. The resulting solution was diluted with H$_2$O. The resulting solution was extracted with of dichloromethane and the combined organic layers were dried over anhydrous sodium sulfate and concentrated under vacuum. The residue was purified by preparative TLC (dichloromethane/MeOH=10:1). This resulted in 620 mg (crude) of methyl 4-[[7-bromo-3-(3-[[(tert-butoxy)carbonyl](methyl)amino]propanamido)quinolin-4-yl]amino]butanoate as a yellow solid.

LC-MS-PH-IFM-7-106-5: (ES, m/z): [M+H]$^+$=523.4

2. Synthesis of Methyl 4-[7-bromo-2-(2-[[(tert-butoxy)carbonyl](methyl)amino]ethyl)-1H-imidazo[4,5-c]quinolin-1-yl]butanoate Into a 25-mL round-bottom flask, was placed a solution of methyl 4-[[7-bromo-3-(3-[[(tert-butoxy)carbonyl](methyl)amino]propanamido)quinolin-4-yl]amino]butanoate (350 mg, 0.67 mmol, 1.00 equiv) in methanol (6 mL). To the solution was added DIEA (3 mL). The resulting solution was stirred overnight at 80° C. The resulting mixture was concentrated under vacuum. The residue was purified by Prep-TLC (dichloromethane/MeOH=10:1). This resulted in 170 mg (50%) of methyl 4-[7-bromo-2-(2-[[(tert-butoxy)carbonyl](methyl)amino]ethyl)-1H-imidazo[4,5-c]quinolin-1-yl]butanoate as a yellow solid.

LC-MS-PH-IFM-7-106-6: (ES, m/z): [M+H]$^+$=505.4

3. Synthesis of 7-bromo-2-(2-[[(tert-butoxy)carbonyl](methyl)amino]ethyl)-1-(4-methoxy-4-oxobutyl)-1H-imidazo[4,5-c]quinolin-5-ium-5-olate Into a 50-mL round-bottom flask, was placed a solution of methyl 4-[7-bromo-2-(2-[[(tert-butoxy)carbonyl](methyl)amino]ethyl)-1H-imidazo[4,5-c]quinolin-1-yl]butanoate (170 mg, 0.34 mmol, 1.00 equiv) in dichloromethane (25 mL). To the solution was added m-CPBA (125 mg, 1.50 equiv). The resulting solution was stirred for 2 h at room temperature. The resulting mixture was concentrated under vacuum. The residue was purified by preparative TLC (dichloromethane/MeOH=10:1). This resulted in 120 mg (68%) of 7-bromo-2-(2-[[(tert-butoxy)carbonyl](methyl)amino]ethyl)-1-(4-methoxy-4-oxobutyl)-1H-imidazo[4,5-c]quinolin-5-ium-5-olate as a yellow solid.

LC-MS-PH-IFM-7-106-7: (ES, m/z): [M+H]$^+$=521.2

4. Synthesis of Methyl 4-[4-amino-7-bromo-2-(2-[[(tert-butoxy)carbonyl](methyl)amino]ethyl)-1H-imidazo[4,5-c]quinolin-1-yl]butanoate Into a 50-mL round-bottom flask, was placed a solution of 7-bromo-2-(2-[[(tert-butoxy)carbonyl](methyl)amino]ethyl)-1-(4-methoxy-4-oxobutyl)-1H-imidazo[4,5-c]quinolin-5-ium-5-olate (120 mg, 0.23 mmol, 1.00 equiv) in dichloromethane (10 mL). To the solution was added TsCl (66 mg, 0.35 mmol, 1.50 equiv) and NH$_4$OH (3 mL). The resulting solution was stirred for 2 h at room temperature. The resulting mixture was concentrated under vacuum. The residue was purified by preparative TLC (dichloromethane/MeOH=6:1). This resulted in 100 mg of methyl 4-[4-amino-7-bromo-2-(2-[[(tert-butoxy)carbonyl](methyl)amino]ethyl)-1H-imidazo[4,5-c]quinolin-1-yl]butanoate as a yellow solid.

LC-MS-PH-IFM-7-106-8: (ES, m/z): [M+H]$^+$=520.2

5. Synthesis of Methyl 4-[4-amino-7-bromo-2-[2-(methylamino)ethyl]-1H-imidazo[4,5-c]quinolin-1-yl]butanoate (Compound 102)

Into a 25-mL round-bottom flask, was placed a solution of methyl 4-[4-amino-7-bromo-2-(2-[[(tert-butoxy)carbonyl](methyl)amino]ethyl)-1H-imidazo[4,5-c]quinolin-1-yl]butanoate (100 mg, 0.19 mmol, 1.00 equiv) in 4N hydrogen chloride/1,4-dioxane (10 mL). The resulting solution was stirred for 2 h at room temperature. The resulting mixture was concentrated under vacuum. The crude product was purified by preparative HPLC with the following conditions: Column: X Bridge Prep C18 OBD, 19*150 mm 5 um C-0013; Mobile phase: Phase A: Water (10 MMOL/L NH$_4$HCO$_3$), Phase B: CAN (20% B to 45% B in 9 min). This resulted in 33.8 mg (42%) of methyl 4-[4-amino-7-bromo-2-[2-(methylamino)ethyl]-1H-imidazo[4,5-c]quinolin-1-yl]butanoate as a white solid.

LC-MS-PH-IFM-7-106-0: (ES, m/z): [M+H]$^+$=422.1

H-NMR-PH-IFM-7-106-0: $^1$H NMR (300 MHz, DMSO-d$_6$): δ 8.08 (d, J=9.0 Hz, 1H), 7.73 (d, J=2.4 Hz, 1H), 7.37-7.33 (m, 1H), 6.75 (s, 2H), 4.55-4.50 (m, 2H), 3.66 (s, 3H), 3.04 (t, J=6.3 Hz, 2H), 2.95 (t, J=6.3 Hz, 2H), 2.58-2.54 (m, 2H), 2.34 (s, 3H), 2.09-2.02 (m, 2H).

Preparative Example 3: General Procedure for Synthesis of 7-Bromo-N$^4$-(4-methoxybenzyl)quinoline-3,4-diamine

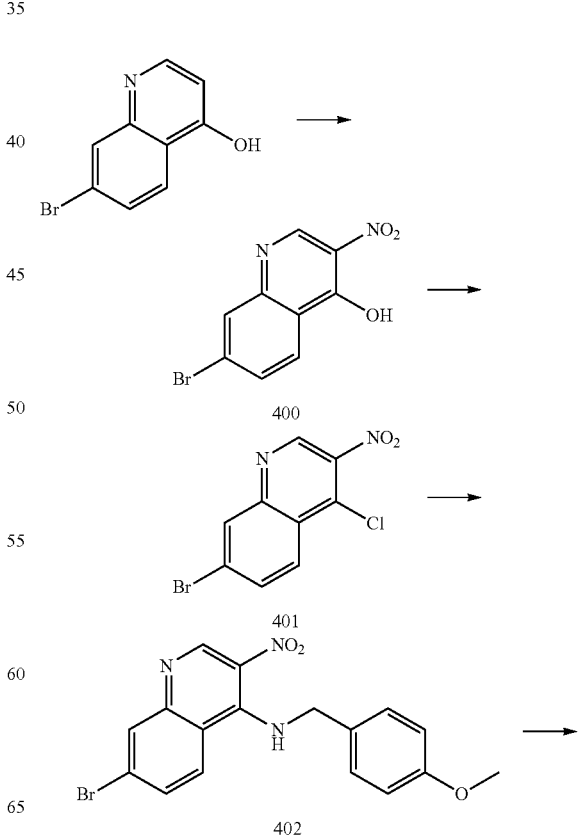

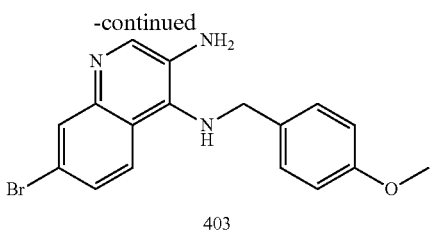

403

1. Preparation of 7-bromo-3-nitroquinolin-4-ol (400)

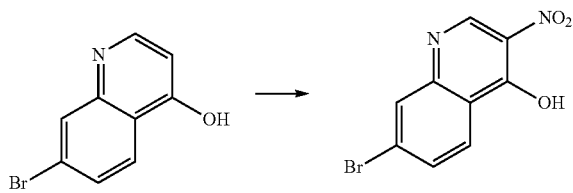 [SMILES: Oc1ccnc2cc(Br)ccc12 ; O=[N+]([O-])c1cnc2cc(Br)ccc2c1O]

7-bromoquinolin-4-ol (4.5 g, 20.0 mol) was dissolved in propionic acid (34 mL). The mixture was heated to 130° C., and nitric acid (1.7 mL, 70%) was added. The reaction was heated at 130° C. (bath temperature) for 4 hours at which time it was cooled to room temperature and filtered. The resulting solid was washed with water (3×20 mL), 2-propanol (20 mL), and hexanes (20 mL). The product was then dried under high vacuum to provide 3.8 g (70.6%) of 7-bromo-3-nitroquinolin-4-ol (400) as a tan powder and used in the next step without further purification. (ES, m/z): [M+H]$^+$=269.2/271.3.

2. Preparation of 7-bromo-4-chloro-3-nitroquinoline (401)

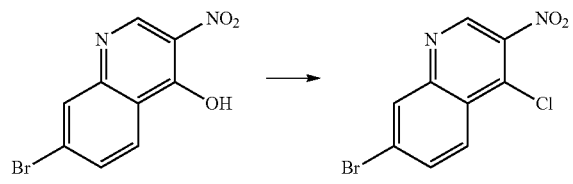 [SMILES: O=[N+]([O-])c1cnc2cc(Br)ccc2c1O ; O=[N+]([O-])c1cnc2cc(Br)ccc2c1Cl]

7-Bromo-3-nitroquinolin-4-ol (400, 3.8 g, 14.12 mmol) was suspended in POCl$_3$ (20 mL). Anhydrous DMF (1 mL) was added. The mixture was then heated to 120° C. under an atmosphere of nitrogen for 3 hours at which time the reaction was cooled to room temperature. The precipitate was collected by filtration, washed with water, and then partitioned between CH$_2$Cl$_2$ (60 mL) and a saturated aqueous solution of Na$_2$CO$_3$. The organic layer was separated, washed with brine, dried over Na$_2$SO$_4$, filtered, and concentrated to afford 3.3 g (11.5 mmol, 81%) of 7-bromo-4-chloro-3-nitroquinoline (401) as a beige-colored solid. (ES, m/z): [M+H]$^+$=287.1/288.9.

Note: It was discovered that if higher temperatures and longer reaction times are used, a significant amount of Cl—Br exchange occurs which affords an intermediate that does not undergo subsequent cross-coupling reactions.

3. Preparation of 7-bromo-N-(4-methoxybenzyl)-3-nitroquinolin-4-amine (402)

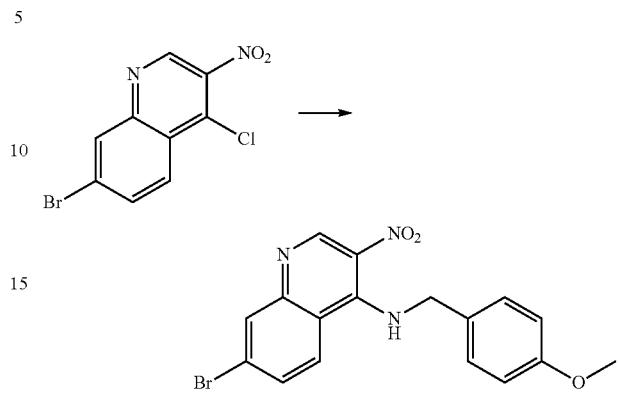

7-bromo-4-chloro-3-nitroquinoline (401, 1.9 g, 6.62 mmol) was dissolved in CH$_2$Cl$_2$ (20 mL). 4-methoxy benzylamine (0.85 mL, 6.7 mmol) was added, followed by NEt$_3$ (0.95 mL, 6.7 mmol). The mixture was stirred at room temperature for 4 h at which time it was diluted with CH$_2$Cl$_2$ (30 mL), washed with water, washed with brine, dried over Na$_2$SO$_4$, and filtered. The resulting solution was evaporated to dryness to afford (7-bromo-3-nitro-quinolin-4-yl)-(4-methoxy-benzyl)-amine (402) as a yellow foam (2.5 g, 6.44 mmol, 97%). This material was used in the next step without further purification. (ES, m/z): [M+H]$^+$=388.3/390.1.

4. Preparation of 7-bromo-N$^4$-(4-methoxybenzyl)quinoline-3,4-diamine (403)

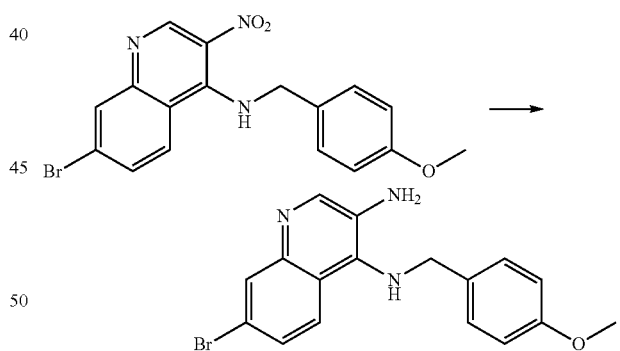

(7-Bromo-3-nitro-quinolin-4-yl)-(4-methoxy-benzyl)-amine (402, 2.5 g, 6.44 mmol) was dissolved in ethanol (60 mL) at room temperature. Tin (II) chloride hydrate (4.8 g, 21.2 mmol) was added in one portion. The mixture was stirred at 65° C. for 3 h at which time water (50 mL) was added, followed by a saturated aqueous solution of NaHCO$_3$ to pH ~9. The mixture was extracted with EtOAc (3×60 mL), and the combined organic layers were dried over Na$_2$SO$_4$, filtered, and concentrated to afford 7-bromo-N$^4$-(4-methoxy-benzyl)-quinoline-3,4-diamine (403, 1.5 g, 4.2 mmol, 65%). This material was used in the next step without further purification. (ES, m/z): [M+H]$^+$=357.9/360.1

Preparative Example 4: Example Preparation Method of Analogs Wherein R²=Hydroxyalkylene and R³=Aryl, Heteroaryl, Heterocyclyl, or Amino

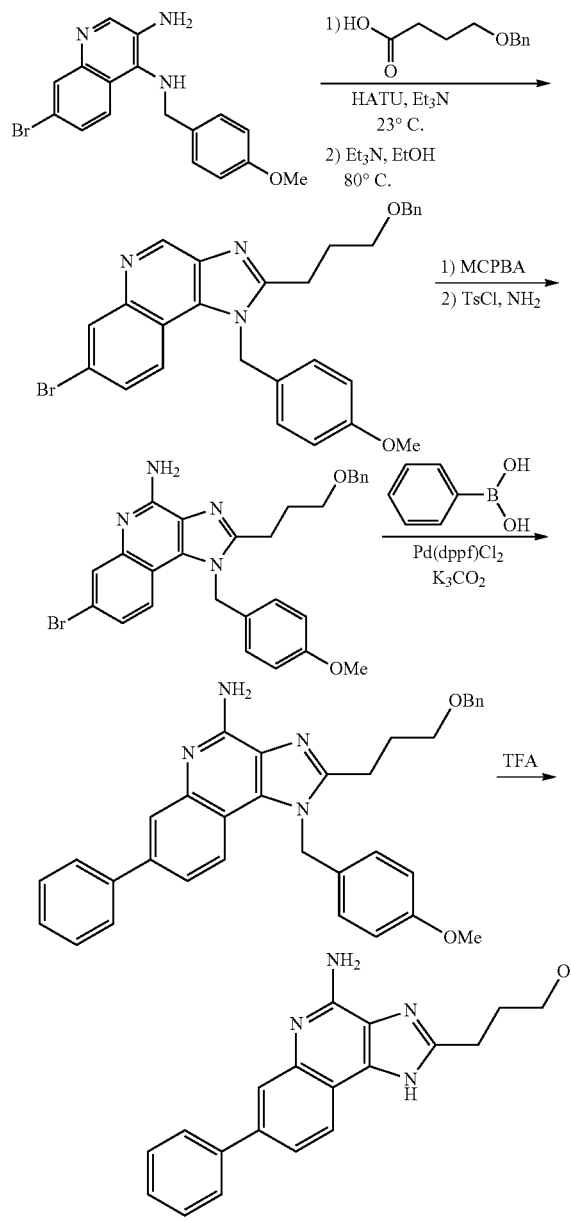

1. Preparation of 2-(3-(benzyloxy)propyl)-7-bromo-1-(4-methoxybenzyl)-1H-imidazo[4,5-c]quinolone

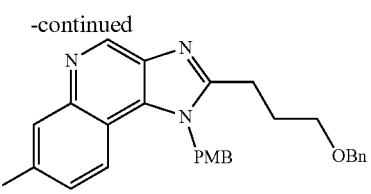

To a solution of 7-bromo-N⁴-(4-methoxy-benzyl)-quinoline-3, 4-diamine (403, 1 g, 2.8 mmol) and 4-benzyloxybutyric acid (0.5 mL, 2.82 mmol)) in CH₂Cl₂ (10 mL) was added HATU (1.2 g, 3.15 mmol) and NEt₃ (1 mL, 7.17 mmol). The mixture was stirred at room temperature for 12 hours at which time it was concentrated to remove all volatiles. EtOH (10 mL) was added, followed by NEt₃ (3 mL). The mixture was stirred in a 70° C. oil bath for 15 hours at which time it was cooled to room temperature. Most volatiles were evaporated in vacuo and the residue was partitioned between CH₂Cl₂ (30 mL) and water (30 mL). The CH₂Cl₂ layer was further washed with water (30 mL), washed with brine, dried over Na₂SO₄, filtered, and concentrated. The crude 2-(3-benzyloxy-propyl)-7-bromo-1-(4-methoxy-benzyl)-1H-imidazo[4,5-c]quinoline (1.2 g, 2.3 mmol, 80%) was used in the next step without further purification. (ES, m/z): [M+H]⁺=516.4/518.1.

2. Preparation of 2-(3-(benzyloxy)propyl)-7-bromo-1-(4-methoxybenzyl)-1H-imidazo[4,5-c]quinoline 5-oxide

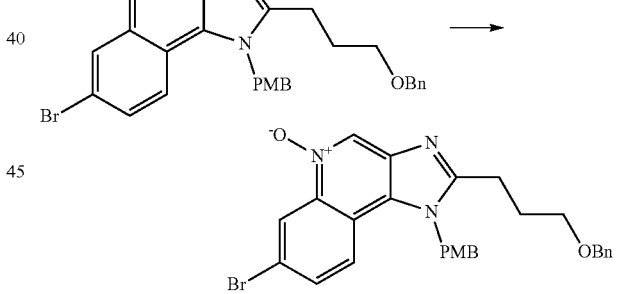

To a solution of 2-(3-benzyloxy-propyl)-7-bromo-1-(4-methoxy-benzyl)-1H-imidazo-[4,5-c]quinoline (xx, 1.2 g, 2.3 mmol) in CH₂Cl₂ (15 mL) were added H₂O₂ (6 mL) and m-chloroperoxybenzoic acid (70% grade, 573 mg, 0.23 mmol, 0.10 equiv). The mixture was stirred for 14 hours at room temperature at which time it was diluted with a saturated aqueous solution of NaHCO₃ and extracted with CH₂Cl₂ (3×20 mL). The combined organic layers were washed with brine, dried over Na₂SO₄, filtered, and concentrated to give crude 2-(3-benzyloxy-propyl)-7-bromo-1-(4-methoxy-benzyl)-1H-imidazo[4,5-c]quinoline 5-oxide (1.1 g, 2 mmol, 89%) as a yellowish foam. (ES, m/z): [M+H]⁺=532.1/534.3

3. Preparation of 2-(3-(benzyloxy)propyl)-7-bromo-1-(4-methoxybenzyl)-1H-imidazo[4,5-c]quinolin-4-amine

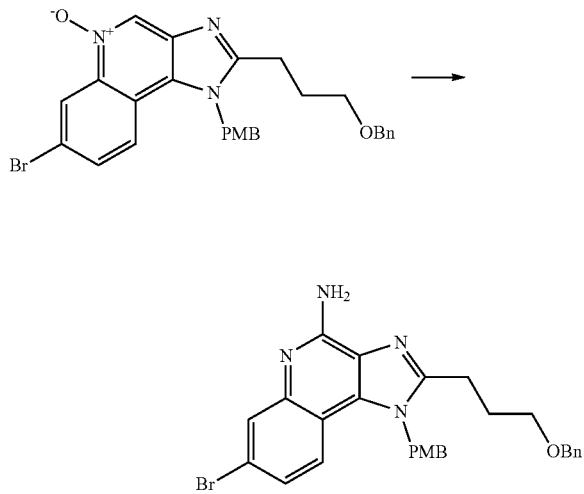

To a solution of 2-(3-benzyloxy-propyl)-7-bromo-1-(4-methoxy-benzyl)-1H-imidazo-[4,5-c]quinolone-5-oxide (1.1 g, 2 mmol) and NH₄OH (25 mL) in dichloromethane (25 mL) cooled in a ice water bath, was added p-toluenesulfonyl chloride (850 mg, 4.45 mmol) in CH₂Cl₂ (5 mL) dropwise. The resulting solution was stirred another 30 min after addition was complete. Water (20 mL) was added and the layers were separated. The aqueous layer was extracted one more time with CH₂Cl₂ (30 mL). The combined organic layers were filtered through a pad of Na₂SO₄ and the filtrate was concentrated in vacuo. The residue was triturated with EtOAc/hexanes (1/3) and dried under high vacuum to afford 2-(3-(benzyloxy)propyl)-7-bromo-1-(4-methoxybenzyl)-1H-imidazo[4,5-c]quinolin-4-amine as a yellow solid (880 mg, 1.64 mmol, 82%). (ES, m/z): [M+H]⁺=516.4/518.1.

4. Coupling with Aryl Bromide a. General Procedure for Suzuki Coupling of Arylboronic Acids and Esters

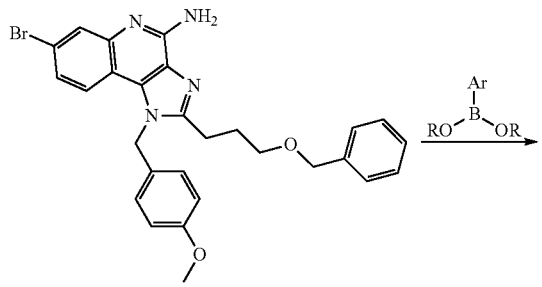

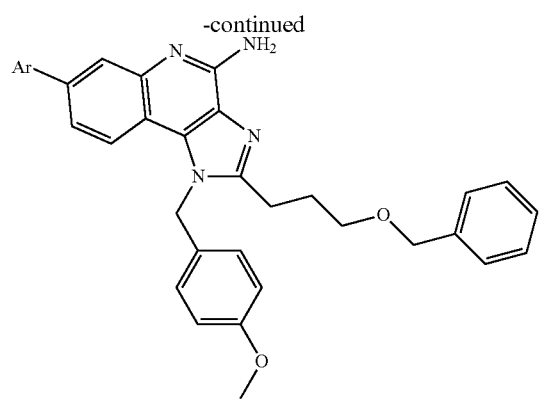

To a solution of 1-(4-methoxybenzyl)-2-(3-(benzyloxy)propyl)-7-bromo-1H-imidazo[4,5-c]quinolin-4-amine (40 mg, 75 μmol) was added an aryl(heteroaryl)boronic acid (or arylboronate ester) (2 equiv), Pd(dppf)Cl₂·CH₂Cl₂ (5 mg), and an aqueous solution of K₂CO₃ (1 mL, 2M aqueous) sequentially. The mixture was heated in a Biotage Initiator microwave reactor at 120° C. for 10 min. The organic layer was diluted with EtOAc and separated, and the aqueous layer was extracted with EtOAc. The combined organic phases were filtered and evaporated, and the crude residue used in the deprotection step without further purification.

b. Alternative Procedure: Ullman Coupling of N-Heterocycles, Lactams, and Amines

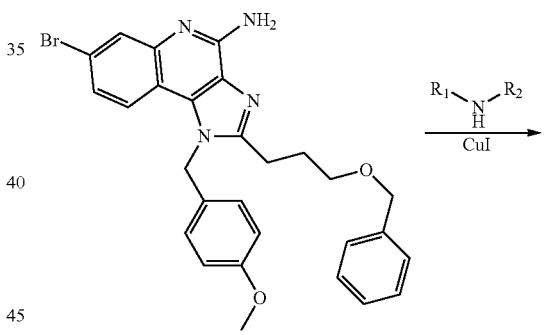

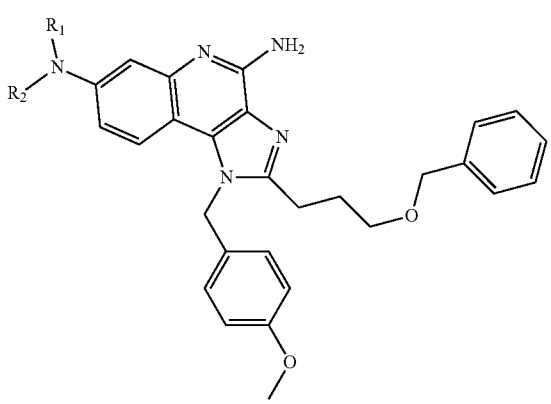

To a solution of 2-(3-(benzyloxy)propyl)-7-bromo-1-(4-methoxybenzyl)-1H-imidazo[4,5-c]quinolin-4-amine (25 mg, 47 μmol) in dry DMSO (2 mL) was added the N-heterocycle (or lactam or amine) (2 equiv), CuI (25 mg, 2 equiv), and Na₂CO₃ (30 mg, 4 equiv) in sequence. The mixture was degassed with argon and N,N'-dimethyl-ethylenediamine (20 mg, 3 equiv) was added. The resulting mixture was stirred at 120° C. for 2 hours. The cooled mixture was diluted with EtOAc, filtered, and the solvent evaporated in vacuo. The crude residue was used in the deprotection step without further purification.

c. Alternative Procedure: Stile Coupling of Stannanes

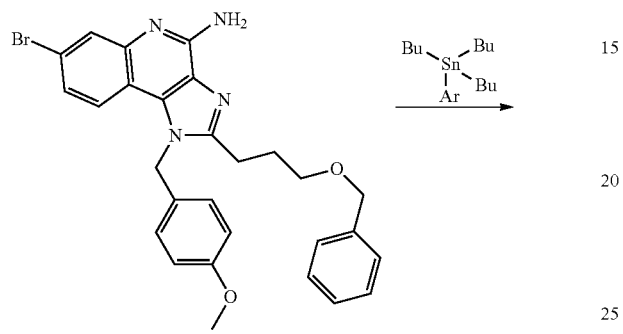
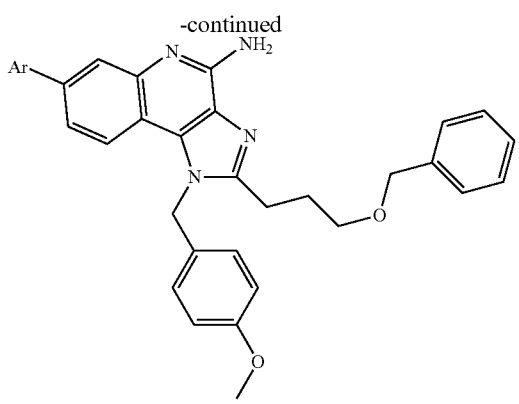

To a solution of 2-(3-(benzyloxy)propyl)-7-bromo-1-(4-methoxybenzyl)-1H-imidazo[4,5-c]quinolin-4-amine (25 mg, 47 μmol) and the aryl(heteroaryl)stannane (2 equiv) in dry 1,4-dioxane (2 mL) was added PdCl₂(PPh₃)₂ (5 mg). The resulting mixture was purged with nitrogen and stirred at 110° C. overnight. The cooled reaction mixture was diluted with EtOAc, the solution filtered, and the solvents evaporated in vacuo. The residue was used in the deprotection step without further purification.

5. General Deprotection/Partial Deprotection Procedure

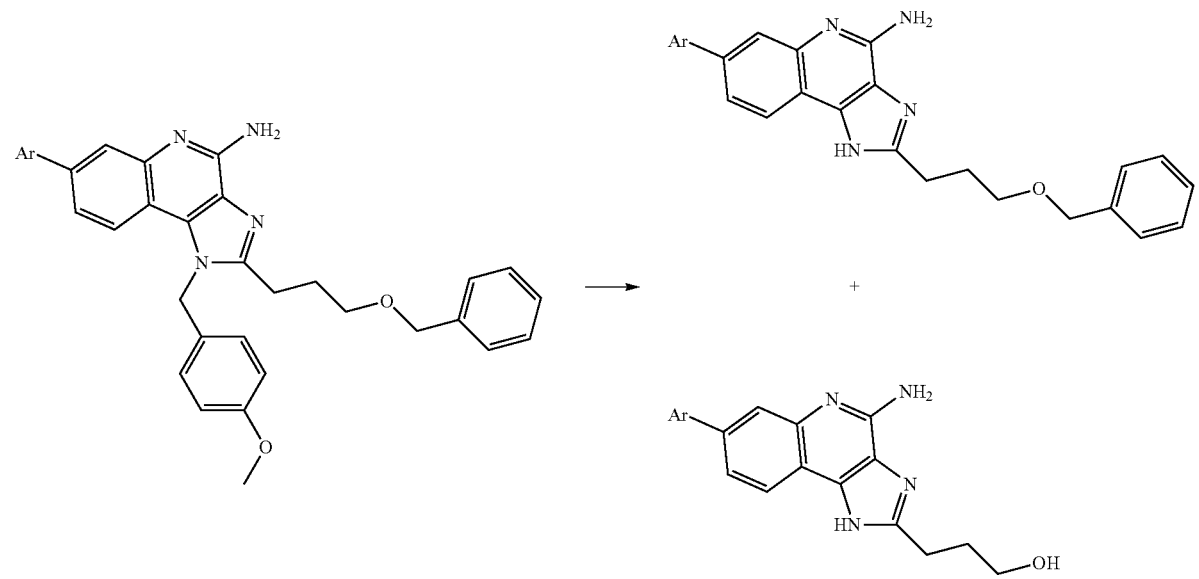

The crude product from the previous step was dissolved in TFA (2 mL) and stirred at 70° C. for approximately 3 hours while following the progress of the reaction by LC/MS. Once the PMB protecting group was completely cleaved and the benzyl was cleaved to the extent of approximately 50% as indicated by LC/MS (note: the incipient primary alcohol appeared as the trifluoroacetate), the mixture was evaporated. The resulting residue was dissolved in MeOH and treated with an aqueous 2M solution of NaOH to obtain a mixture of free alcohol and benzyl ether products. Acetic acid was added to neutralize the mixture, which was then evaporated and purified by HPLC to separate the alcohol and benzyl ether as their respective hydrochloride salts. Alternatively, the TFA solution above was heated at 70° C. until the benzyl group was completely cleaved to furnish the completely deprotected alcohol.

The compounds depicted in Table 3 were made according to the above synthetic procedures.

TABLE 3

| Structure | Compound | IUPAC NAME | LCMS [M + H]+ |
|---|---|---|---|
| 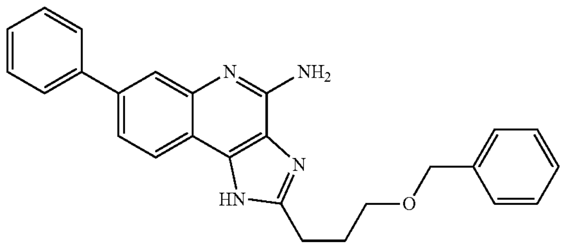 [SMILES: Nc1nc2cc(-c3ccccc3)ccc2c2[nH]c(CCCOCc3ccccc3)nc12] | 144 | 7-phenyl-2-(3-phenylmethoxypropyl)-1H-imidazo[4,5-c]quinolin-4-amine | 409.2 |
| 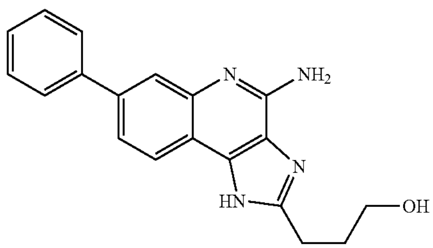 [SMILES: Nc1nc2cc(-c3ccccc3)ccc2c2[nH]c(CCCO)nc12] | 145 | 3-(4-amino-7-phenyl-1H-imidazo[4,5-c]quinolin-2-yl)propan-1-ol | 319.1 |
| 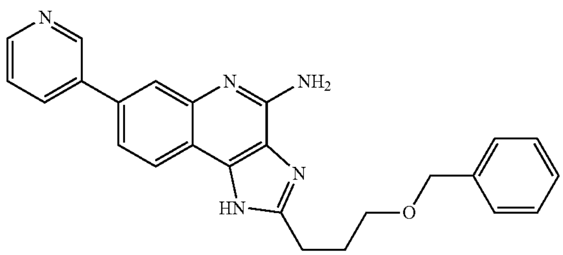 [SMILES: Nc1nc2cc(-c3cccnc3)ccc2c2[nH]c(CCCOCc3ccccc3)nc12] | 146 | 2-(3-phenylmethoxypropyl)-7-pyridin-3-yl-1H-imidazo[4,5-c]quinolin-4-amine | 410.2 |
| 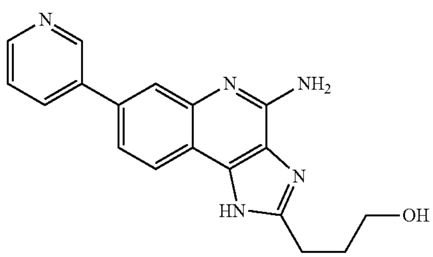 [SMILES: Nc1nc2cc(-c3cccnc3)ccc2c2[nH]c(CCCO)nc12] | 147 | 3-(4-amino-7-pyridin-3-yl-1H-imidazo[4,5-c]quinolin-2-yl)propan-1-ol | 320.1 |
| 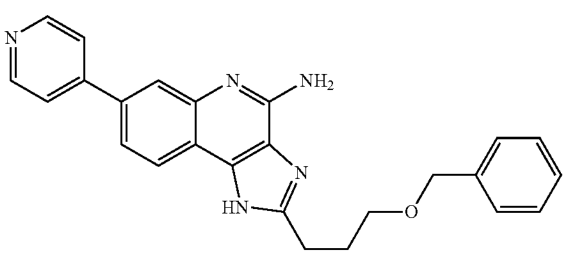 [SMILES: Nc1nc2cc(-c3ccncc3)ccc2c2[nH]c(CCCOCc3ccccc3)nc12] | 148 | 2-(3-phenylmethoxypropyl)-7-pyridin-4-yl-1H-imidazo[4,5-c]quinolin-4-amine | 410.2 |
| 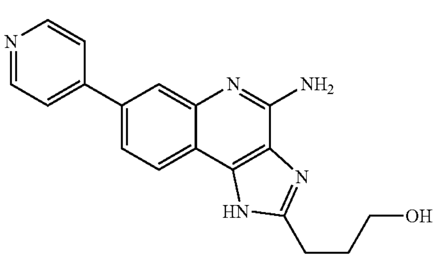 [SMILES: Nc1nc2cc(-c3ccncc3)ccc2c2[nH]c(CCCO)nc12] | 149 | 3-(4-amino-7-pyridin-4-yl-1H-imidazo[4,5-c]quinolin-2-yl)propan-1-ol | 320.1 |

TABLE 3-continued

| Structure | Compound | IUPAC NAME | LCMS [M + H]+ |
|---|---|---|---|
| 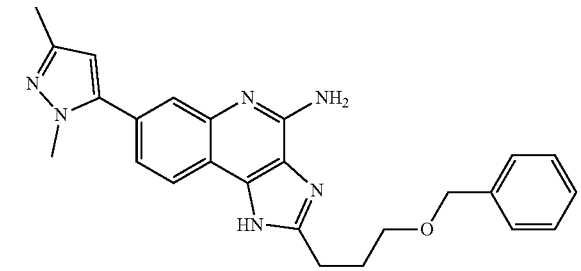 [SMILES: Cc1cc(-c2ccc3c(c2)nc(N)c2nc(CCCOCc4ccccc4)[nH]c23)n(C)n1] | 150 | 7-(2,5-dimethylpyrazol-3-yl)-2-(3-phenylmethoxypropyl)-1H-imidazo[4,5-c]quinolin-4-amine | 427.2 |
| 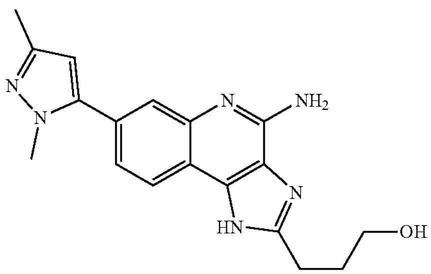 [SMILES: Cc1cc(-c2ccc3c(c2)nc(N)c2nc(CCCO)[nH]c23)n(C)n1] | 151 | 3-[4-amino-7-(2,5-dimethylpyrazol-3-yl)-1H-imidazo[4,5-c]quinolin-2-yl]propan-1-ol | 337.2 |
| 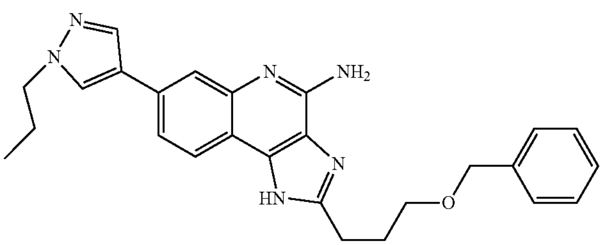 [SMILES: CCCn1cc(-c2ccc3c(c2)nc(N)c2nc(CCCOCc4ccccc4)[nH]c23)cn1] | 152 | 2-(3-phenylmethoxypropyl)-7-(1-propylpyrazol-4-yl)-1H-imidazo[4,5-c]quinolin-4-amine | 441.2 |
| 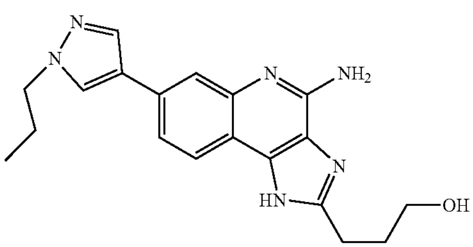 [SMILES: CCCn1cc(-c2ccc3c(c2)nc(N)c2nc(CCCO)[nH]c23)cn1] | 153 | 3-[4-amino-7-(1-propylpyrazol-4-yl)-1H-imidazo[4,5-c]quinolin-2-yl]propan-1-ol | 351.2 |
| 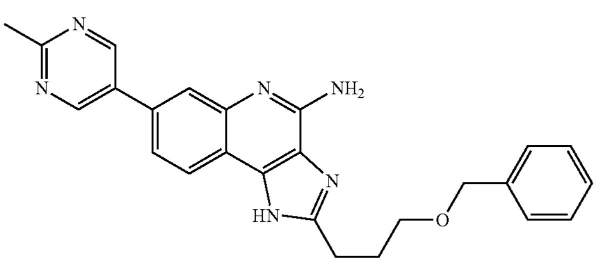 [SMILES: Cc1ncc(-c2ccc3c(c2)nc(N)c2nc(CCCOCc4ccccc4)[nH]c23)cn1] | 154 | 7-(2-methylpyrimidin-5-yl)-2-(3-phenylmethoxypropyl)-1H-imidazo[4,5-c]quinolin-4-amine | 425.2 |
| 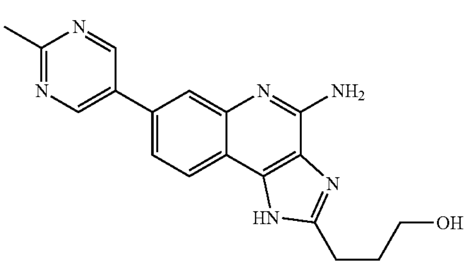 | 155 | 3-[4-amino-7-(2-methylpyrimidin-5-yl)-1H-imidazo[4,5-c]quinolin-2-yl]propan-1-ol | 335.1 |

TABLE 3-continued

| Structure | Compound | IUPAC NAME | LCMS [M + H]+ |
|---|---|---|---|
| 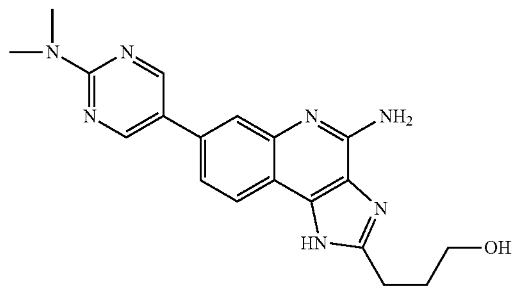 [SMILES: CN(C)c1ncc(-c2ccc3c(c2)nc(N)c2nc(CCCO)[nH]c23)cn1] | 156 | 3-[4-amino-7-[2-(dimethylamino)pyrimidin-5-yl]-1H-imidazo[4,5-c]quinolin-2-yl]propan-1-ol | 364.2 |
| 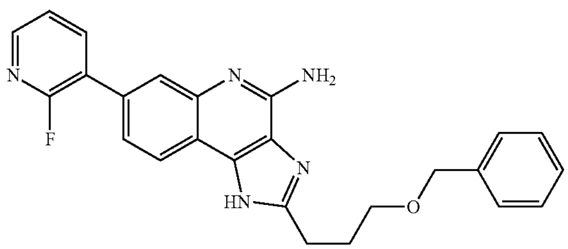 [SMILES: Nc1nc2cc(-c3cccnc3F)ccc2c2[nH]c(CCCOCc3ccccc3)nc12] | 157 | 7-(2-fluoropyridin-3-yl)-2-(3-phenylmethoxypropyl)-1H-imidazo[4,5-c]quinolin-4-amine | 428.2 |
| 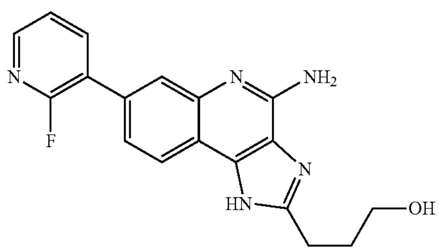 [SMILES: Nc1nc2cc(-c3cccnc3F)ccc2c2[nH]c(CCCO)nc12] | 158 | 3-[4-amino-7-(2-fluoropyridin-3-yl)-1H-imidazo[4,5-c]quinolin-2-yl]propan-1-ol | 338.1 |
| 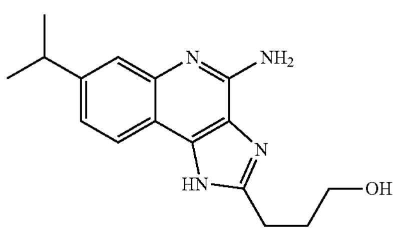 [SMILES: CC(C)c1ccc2c(c1)nc(N)c1nc(CCCO)[nH]c12] | 159 | 3-(4-amino-7-propan-2-yl-1H-imidazo[4,5-c]quinolin-2-yl)propan-1-ol | 285.2 |
| 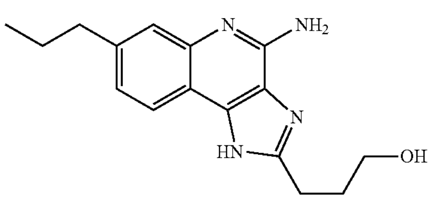 [SMILES: CCCc1ccc2c(c1)nc(N)c1nc(CCCO)[nH]c12] | 160 | 3-(4-amino-7-propyl-1H-imidazo[4,5-c]quinolin-2-yl)propan-1-ol | 285.2 |
| 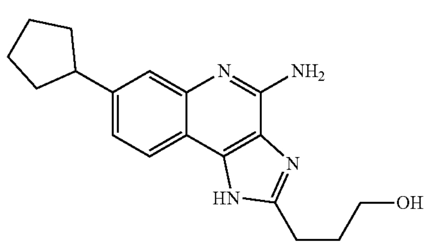 [SMILES: Nc1nc2cc(C3CCCC3)ccc2c2[nH]c(CCCO)nc12] | 161 | 3-(4-amino-7-cyclopentyl-1H-imidazo[4,5-c]quinolin-2-yl)propan-1-ol | 311.2 |

TABLE 3-continued

| Structure | Compound | IUPAC NAME | LCMS [M + H]+ |
|---|---|---|---|
| 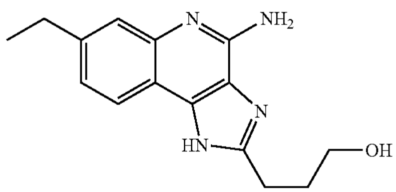 [SMILES: CCc1ccc2c(c1)nc(N)c1nc(CCCO)[nH]c12] | 162 | 3-(4-amino-7-ethyl-1H-imidazo[4,5-c]quinolin-2-yl)propan-1-ol | 271.1 |
| 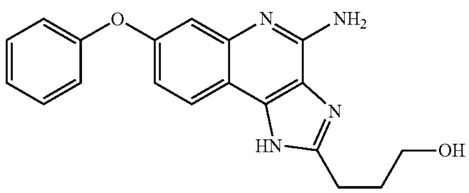 [SMILES: Nc1nc2cc(Oc3ccccc3)ccc2c2[nH]c(CCCO)nc12] | 163 | 3-(4-amino-7-phenoxy-1H-imidazo[4,5-c]quinolin-2-yl)propan-1-ol | 335.1 |
| 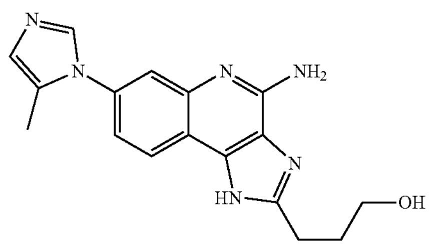 [SMILES: Cc1cncn1-c1ccc2c(c1)nc(N)c1nc(CCCO)[nH]c12] | 164 | 3-[4-amino-7-(2-methylimidazol-1-yl)-1H-imidazo[4,5-c]quinolin-2-yl]propan-1-ol | 323.1 |
| 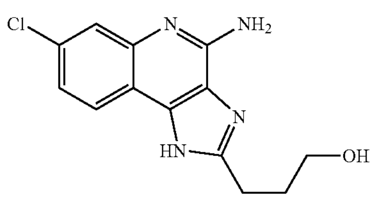 [SMILES: Nc1nc2cc(Cl)ccc2c2[nH]c(CCCO)nc12] | 165 | 3-(4-amino-7-chloro-1H-imidazo[4,5-c]quinolin-2-yl)propan-1-ol | 277.1 |
| 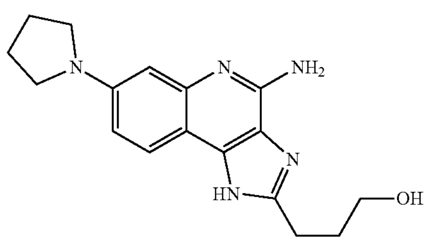 [SMILES: Nc1nc2cc(N3CCCC3)ccc2c2[nH]c(CCCO)nc12] | 166 | 3-(4-amino-7-pyrrolidin-1-yl-1H-imidazo[4,5-c]quinolin-2-yl)propan-1-ol | 312.2 |
| 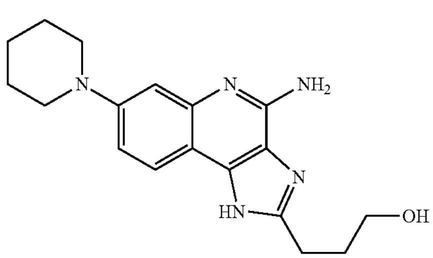 [SMILES: Nc1nc2cc(N3CCCCC3)ccc2c2[nH]c(CCCO)nc12] | 167 | 3-(4-amino-7-piperidin-1-yl-1H-imidazo[4,5-c]quinolin-2-yl)propan-1-ol | 326.2 |

TABLE 3-continued

| Structure | Compound | IUPAC NAME | LCMS [M + H]+ |
|---|---|---|---|
| 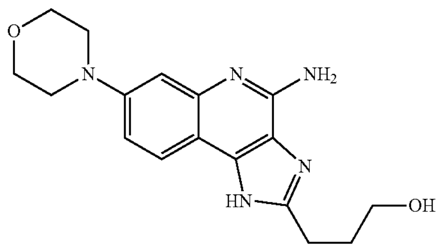 [SMILES: Nc1nc2cc(N3CCOCC3)ccc2c2[nH]c(CCCO)nc12] | 168 | 3-(4-amino-7-morpholin-4-yl-1H-imidazo[4,5-c]quinolin-2-yl)propan-1-ol | 328.2 |
| 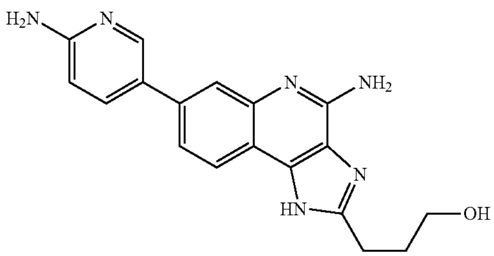 [SMILES: Nc1ccc(-c2ccc3c(c2)nc(N)c2nc(CCCO)[nH]c23)cn1] | 170 | 3-[4-amino-7-(6-aminopyridin-3-yl)-1H-imidazo[4,5-c]quinolin-2-yl]propan-1-ol | 335.1 |
| 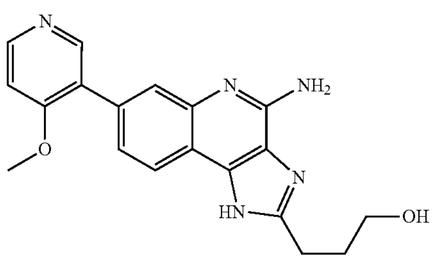 [SMILES: COc1ccncc1-c1ccc2c(c1)nc(N)c1nc(CCCO)[nH]c12] | 171 | 3-[4-amino-7-(4-methoxypyridin-3-yl)-1H-imidazo[4,5-c]quinolin-2-yl]propan-1-ol | 350.1 |
| 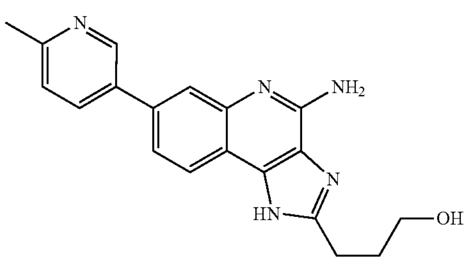 | 172 | 3-[4-amino-7-(6-methylpyridin-3-yl)-1H-imidazo[4,5-c]quinolin-2-yl]propan-1-ol | 334.1 |
| 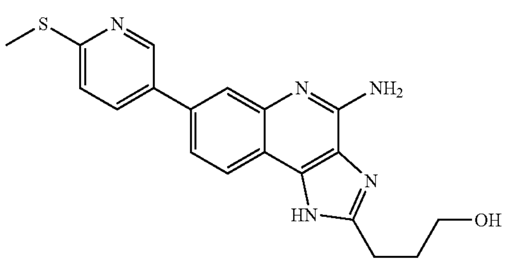 [SMILES: CSc1ccc(-c2ccc3c(c2)nc(N)c2nc(CCCO)[nH]c23)cn1] | 173 | 3-[4-amino-7-(6-methylsulfanylpyridin-3-yl)-1H-imidazo[4,5-c]quinolin-2-yl]propan-1-ol | 366.1 |
| 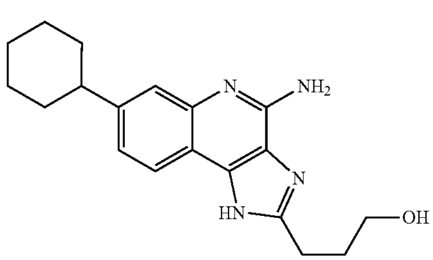 [SMILES: Nc1nc2cc(C3CCCCC3)ccc2c2[nH]c(CCCO)nc12] | 174 | 3-(4-amino-7-cyclohexyl-1H-imidazo[4,5-c]quinolin-2-yl)propan-1-ol | 325.2 |

TABLE 3-continued

| Structure | Compound | IUPAC NAME | LCMS [M + H]+ |
|---|---|---|---|
| 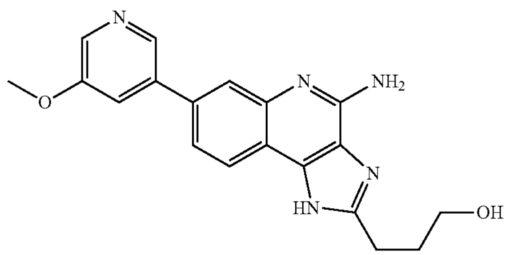 [SMILES: COc1cncc(-c2ccc3c(c2)nc(N)c2nc(CCCO)[nH]c23)c1] | 175 | 3-[4-amino-7-(5-methoxypyridin-3-yl)-1H-imidazo[4,5-c]quinolin-2-yl]propan-1-ol | 350.1 |
| 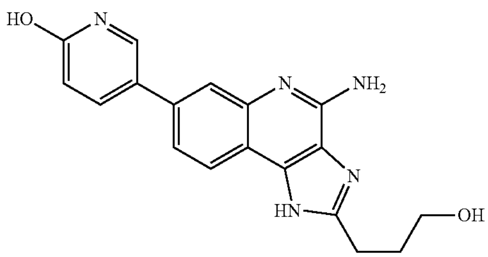 [SMILES: Nc1nc2cc(-c3ccc(O)nc3)ccc2c2[nH]c(CCCO)nc12] | 176 | 5-[4-amino-2-(3-hydroxypropyl)-1H-imidazo[4,5-c]quinolin-7-yl]pyridin-2-ol | 336.1 |
| 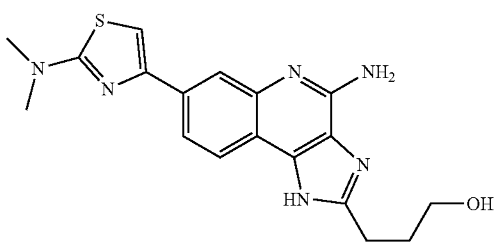 [SMILES: CN(C)c1nc(-c2ccc3c(c2)nc(N)c2nc(CCCO)[nH]c23)cs1] | 177 | 3-[4-amino-7-[2-(dimethylamino)-1,3-thiazol-4-yl]-1H-imidazo[4,5-c]quinolin-2-yl]propan-1-ol | 369.1 |
| 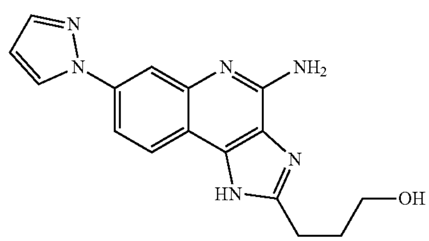 [SMILES: Nc1nc2cc(-n3cccn3)ccc2c2[nH]c(CCCO)nc12] | 178 | 3-(4-amino-7-pyrazol-1-yl-1H-imidazo[4,5-c]quinolin-2-yl)propan-1-ol | 309.1 |
| 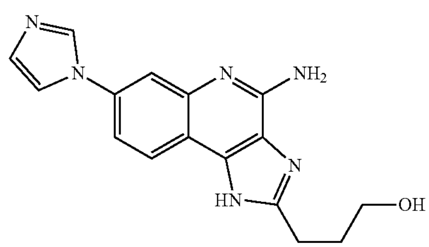 [SMILES: Nc1nc2cc(-n3ccnc3)ccc2c2[nH]c(CCCO)nc12] | 179 | 3-(4-amino-7-imidazol-1-yl-1H-imidazo[4,5-c]quinolin-2-yl)propan-1-ol | 309.1 |
| 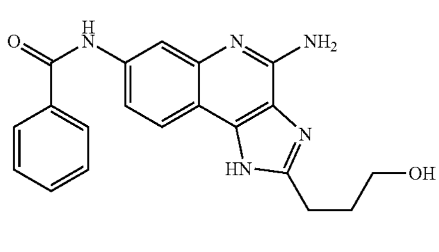 [SMILES: Nc1nc2cc(NC(=O)c3ccccc3)ccc2c2[nH]c(CCCO)nc12] | 180 | N-[4-amino-2-(3-hydroxypropyl)-1H-imidazo[4,5-c]quinolin-7-yl]benzamide | 362.1 |

TABLE 3-continued

| Structure | Compound | IUPAC NAME | LCMS [M + H]+ |
|---|---|---|---|
| 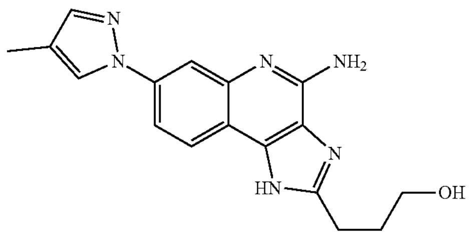 [SMILES: Cc1cnn(-c2ccc3c(c2)nc(N)c2nc(CCCO)[nH]c23)c1] | 181 | 3-[4-amino-7-(4-methylpyrazol-1-yl)-1H-imidazo[4,5-c]quinolin-2-yl]propan-1-ol | 323.1 |
| 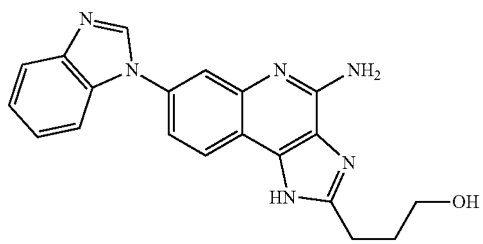 [SMILES: Nc1nc2cc(-n3cnc4ccccc43)ccc2c2[nH]c(CCCO)nc12] | 182 | 3-[4-amino-7-(benzimidazol-1-yl)-1H-imidazo[4,5-c]quinolin-2-yl]propan-1-ol | 359.1 |
| 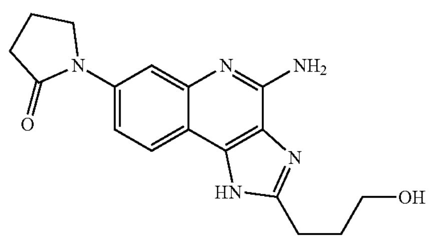 [SMILES: Nc1nc2cc(N3CCCC3=O)ccc2c2[nH]c(CCCO)nc12] | 183 | 1-[4-amino-2-(3-hydroxypropyl)-1H-imidazo[4,5-c]quinolin-7-yl]pyrrolidin-2-one | 326.1 |
| 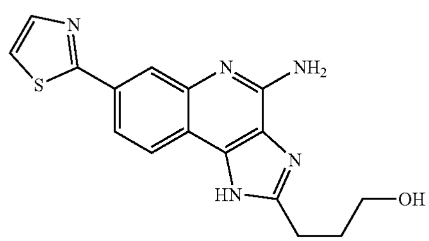 [SMILES: Nc1nc2cc(-c3nccs3)ccc2c2[nH]c(CCCO)nc12] | 184 | 3-[4-amino-7-(1,3-thiazol-2-yl)-1H-imidazo[4,5-c]quinolin-2-yl]propan-1-ol | 326.1 |
| 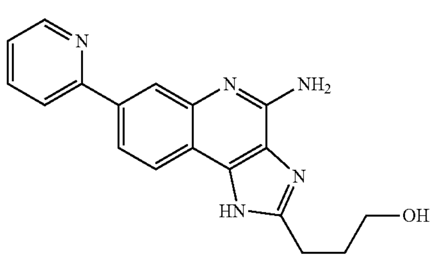 | 185 | 3-(4-amino-7-pyridin-2-yl-1H-imidazo[4,5-c]quinolin-2-yl)propan-1-ol | 320.1 |
| 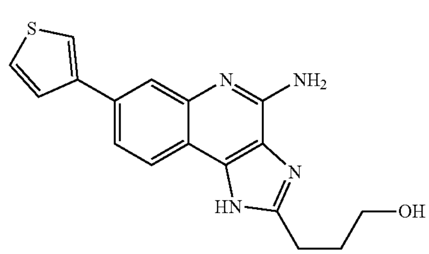 [SMILES: Nc1nc2cc(-c3ccsc3)ccc2c2[nH]c(CCCO)nc12] | 186 | 3-(4-amino-7-thiophen-3-yl-1H-imidazo[4,5-c]quinolin-2-yl)propan-1-ol | 325.1 |

TABLE 3-continued

| Structure | Compound | IUPAC NAME | LCMS [M + H]+ |
|---|---|---|---|
| 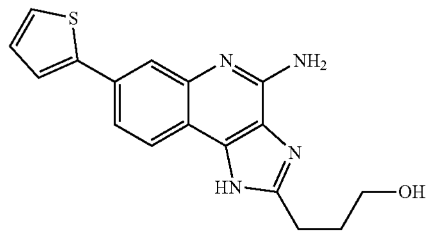 [SMILES: Nc1nc2cc(-c3cccs3)ccc2c2[nH]c(CCCO)nc12] | 187 | 3-(4-amino-7-thiophen-2-yl-1H-imidazo[4,5-c]quinolin-2-yl)propan-1-ol | 325.1 |
| 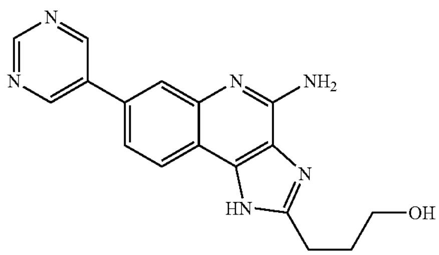 [SMILES: Nc1nc2cc(-c3cncnc3)ccc2c2[nH]c(CCCO)nc12] | 188 | 3-(4-amino-7-pyrimidin-5-yl-1H-imidazo[4,5-c]quinolin-2-yl)propan-1-ol | 321.1 |
| 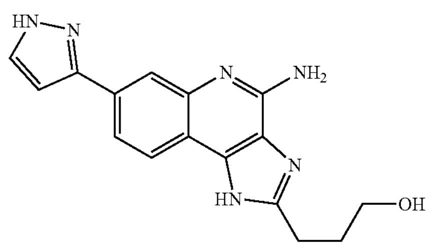 [SMILES: Nc1nc2cc(-c3cc[nH]n3)ccc2c2[nH]c(CCCO)nc12] | 189 | 3-[4-amino-7-(1H-pyrazol-3-yl)-1H-imidazo[4,5-c]quinolin-2-yl]propan-1-ol | 309.1 |
| 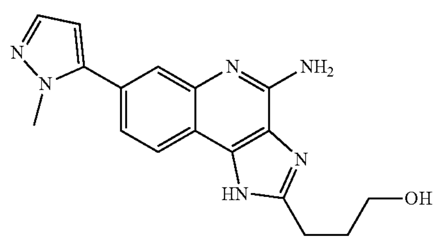 [SMILES: Cn1nccc1-c1ccc2c(c1)nc(N)c1nc(CCCO)[nH]c12] | 190 | 3-[4-amino-7-(2-methylpyrazol-3-yl)-1H-imidazo[4,5-c]quinolin-2-yl]propan-1-ol | 323.1 |
| 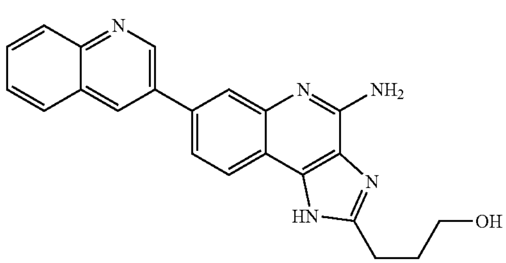 [SMILES: Nc1nc2cc(-c3cnc4ccccc4c3)ccc2c2[nH]c(CCCO)nc12] | 191 | 3-(4-amino-7-quinolin-3-yl-1H-imidazo[4,5-c]quinolin-2-yl)propan-1-ol | 370.1 |
| 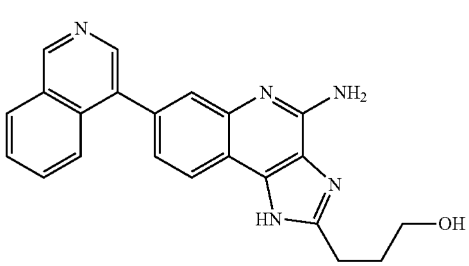 [SMILES: Nc1nc2cc(-c3cncc4ccccc34)ccc2c2[nH]c(CCCO)nc12] | 192 | 3-(4-amino-7-isoquinolin-4-yl-1H-imidazo[4,5-c]quinolin-2-yl)propan-1-ol | 370.1 |

TABLE 3-continued

| Structure | Compound | IUPAC NAME | LCMS [M + H]+ |
|---|---|---|---|
| 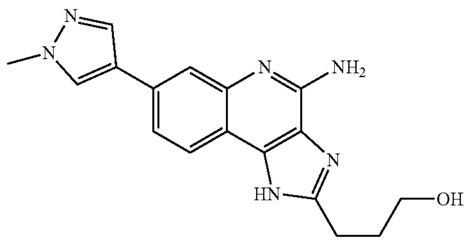 [SMILES: Cn1cc(-c2ccc3c(c2)nc(N)c2nc(CCCO)[nH]c23)cn1] | 193 | 3-[4-amino-7-(1-methylpyrazol-4-yl)-1H-imidazo[4,5-c]quinolin-2-yl]propan-1-ol | 323.1 |
| 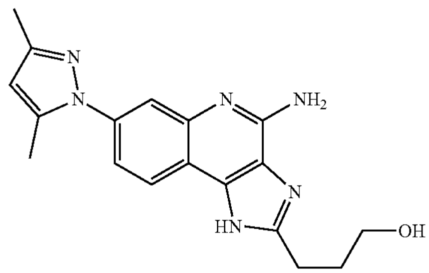 [SMILES: Cc1cc(C)n(-c2ccc3c(c2)nc(N)c2nc(CCCO)[nH]c23)n1] | 194 | 3-[4-amino-7-(3,5-dimethylpyrazol-1-yl)-1H-imidazo[4,5-c]quinolin-2-yl]propan-1-ol | 337.2 |
| 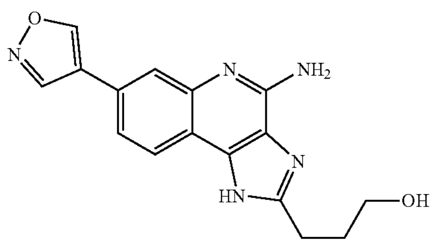 [SMILES: Nc1nc2cc(-c3cnoc3)ccc2c2[nH]c(CCCO)nc12] | 195 | 3-[4-amino-7-(1,2-oxazol-4-yl)-1H-imidazo[4,5-c]quinolin-2-yl]propan-1-ol | 310.1 |
| 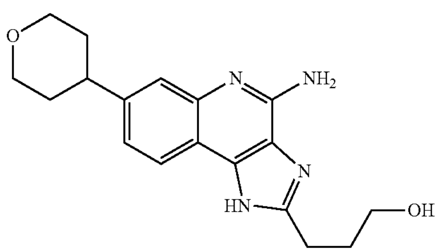 [SMILES: Nc1nc2cc(C3CCOCC3)ccc2c2[nH]c(CCCO)nc12] | 196 | 3-[4-amino-7-(oxan-4-yl)-1H-imidazo[4,5-c]quinolin-2-yl]propan-1-ol | 327.2 |
| 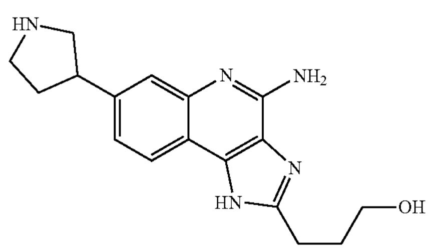 [SMILES: Nc1nc2cc(C3CCNC3)ccc2c2[nH]c(CCCO)nc12] | 197 | 3-(4-amino-7-pyrrolidin-3-yl-1H-imidazo[4,5-c]quinolin-2-yl)propan-1-ol | 312.2 |
| 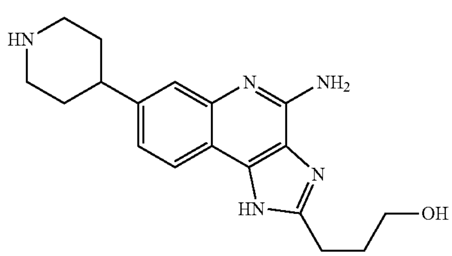 [SMILES: Nc1nc2cc(C3CCNCC3)ccc2c2[nH]c(CCCO)nc12] | 198 | 3-(4-amino-7-piperidin-4-yl-1H-imidazo[4,5-c]quinolin-2-yl)propan-1-ol | 326.2 |

TABLE 3-continued

| Structure | Compound | IUPAC NAME | LCMS [M + H]+ |
|---|---|---|---|
| 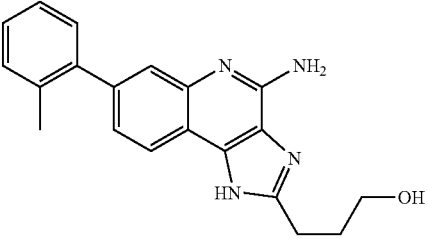 [SMILES: Cc1ccccc1-c1ccc2c(c1)nc(N)c1nc(CCCO)[nH]c12] | 199 | 3-[4-amino-7-(2-methylphenyl)-1H-imidazo[4,5-c]quinolin-2-yl]propan-1-ol | 333.2 |
| 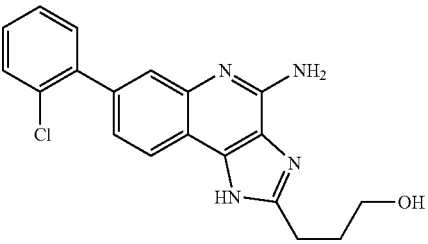 | 200 | 3-[4-amino-7-(2-chlorophenyl)-1H-imidazo[4,5-c]quinolin-2-yl]propan-1-ol | 353.1 |
| 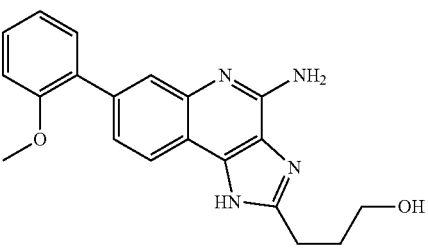 [SMILES: COc1ccccc1-c1ccc2c(c1)nc(N)c1nc(CCCO)[nH]c12] | 201 | 3-[4-amino-7-(2-methoxyphenyl)-1H-imidazo[4,5-c]quinolin-2-yl]propan-1-ol | 349.1 |
| 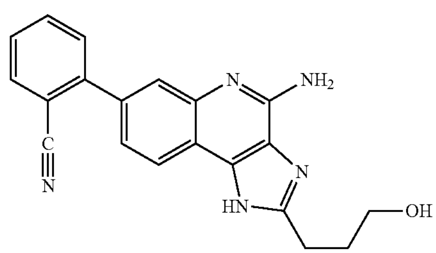 [SMILES: N#Cc1ccccc1-c1ccc2c(c1)nc(N)c1nc(CCCO)[nH]c12] | 202 | 2-[4-amino-2-(3-hydroxypropyl)-1H-imidazo[4,5-c]quinolin-7-yl]benzonitrile | 344.1 |
| 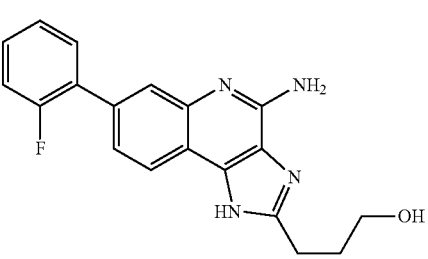 | 203 | 3-[4-amino-7-(2-fluorophenyl)-1H-imidazo[4,5-c]quinolin-2-yl]propan-1-ol | 337.1 |
| 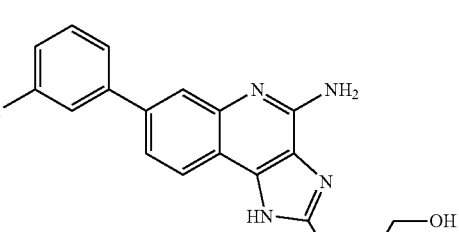 | 204 | 3-[4-amino-7-(3-chlorophenyl)-1H-imidazo[4,5-c]quinolin-2-yl]propan-1-ol | 353.1 |

TABLE 3-continued

| Structure | Compound | IUPAC NAME | LCMS [M + H]+ |
|---|---|---|---|
| 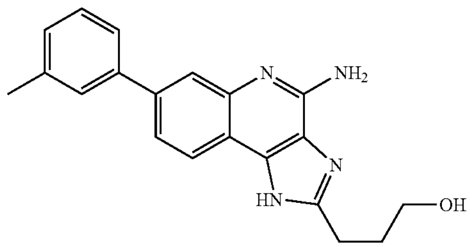 [SMILES: Cc1cccc(-c2ccc3c(c2)nc(N)c2nc(CCCO)[nH]c23)c1] | 205 | 3-[4-amino-7-(3-methylphenyl)-1H-imidazo[4,5-c]quinolin-2-yl]propan-1-ol | 333.2 |
| 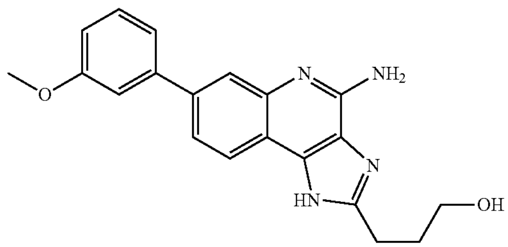 [SMILES: COc1cccc(-c2ccc3c(c2)nc(N)c2nc(CCCO)[nH]c23)c1] | 206 | 3-[4-amino-7-(3-methoxyphenyl)-1H-imidazo[4,5-c]quinolin-2-yl]propan-1-ol | 349.1 |
| 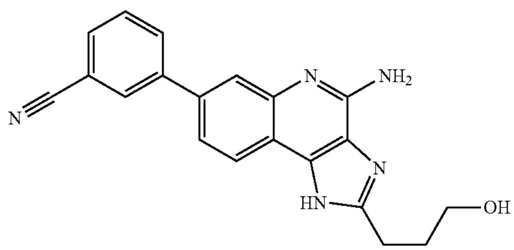 [SMILES: N#Cc1cccc(-c2ccc3c(c2)nc(N)c2nc(CCCO)[nH]c23)c1] | 207 | 3-[4-amino-2-(3-hydroxypropyl)-1H-imidazo[4,5-c]quinolin-7-yl]benzonitrile | 344.1 |
| 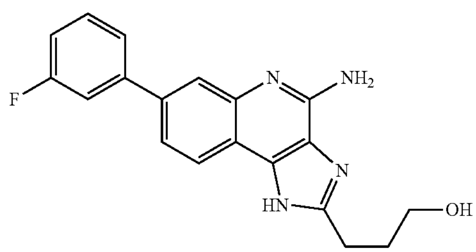 [SMILES: Nc1nc2cc(-c3cccc(F)c3)ccc2c2[nH]c(CCCO)nc12] | 208 | 3-[4-amino-7-(3-fluorophenyl)-1H-imidazo[4,5-c]quinolin-2-yl]propan-1-ol | 337.1 |
| 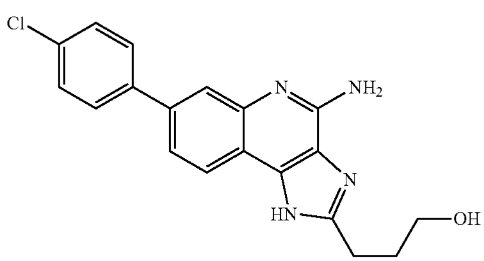 [SMILES: Nc1nc2cc(-c3ccc(Cl)cc3)ccc2c2[nH]c(CCCO)nc12] | 209 | 3-[4-amino-7-(4-chlorophenyl)-1H-imidazo[4,5-c]quinolin-2-yl]propan-1-ol | 353.1 |
| 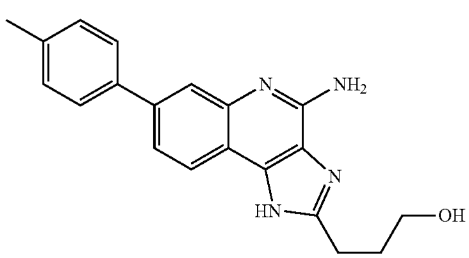 [SMILES: Cc1ccc(-c2ccc3c(c2)nc(N)c2nc(CCCO)[nH]c23)cc1] | 210 | 3-[4-amino-7-(4-methylphenyl)-1H-imidazo[4,5-c]quinolin-2-yl]propan-1-ol | 333.2 |

TABLE 3-continued

| Structure | Compound | IUPAC NAME | LCMS [M + H]+ |
|---|---|---|---|
| 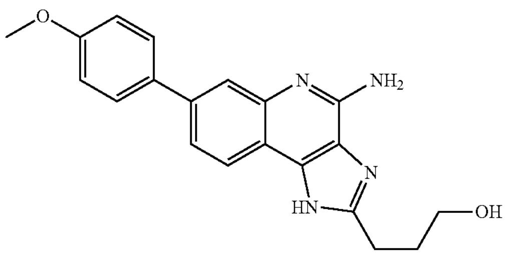 [SMILES: COc1ccc(-c2ccc3c(c2)nc(N)c2nc(CCCO)[nH]c23)cc1] | 211 | 3-[4-amino-7-(4-methoxyphenyl)-1H-imidazo[4,5-c]quinolin-2-yl]propan-1-ol | 349.1 |
| 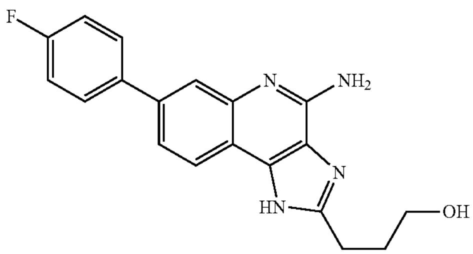 [SMILES: Nc1nc2cc(-c3ccc(F)cc3)ccc2c2[nH]c(CCCO)nc12] | 212 | 3-[4-amino-7-(4-fluorophenyl)-1H-imidazo[4,5-c]quinolin-2-yl]propan-1-ol | 337.1 |
| 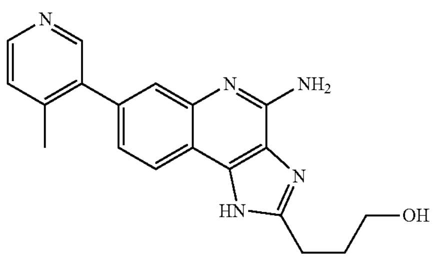 [SMILES: Cc1ccncc1-c1ccc2c(c1)nc(N)c1nc(CCCO)[nH]c12] | 213 | 3-[4-amino-7-(4-methylpyridin-3-yl)-1H-imidazo[4,5-c]quinolin-2-yl]propan-1-ol | 334.1 |
| 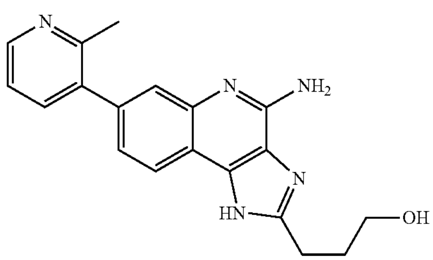 | 214 | 3-[4-amino-7-(2-methylpyridin-3-yl)-1H-imidazo[4,5-c]quinolin-2-yl]propan-1-ol | 334.1 |
| 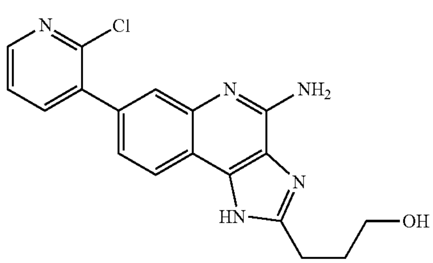 [SMILES: Nc1nc2cc(-c3cccnc3Cl)ccc2c2[nH]c(CCCO)nc12] | 215 | 3-[4-amino-7-(2-chloropyridin-3-yl)-1H-imidazo[4,5-c]quinolin-2-yl]propan-1-ol | 354.1 |

Example 4: Bioassay

Inhibition of IL-1β Production in PMA-Differentiated THP-1 Cells

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 µg/ml), and maintained in log phase prior to experimental setup. Prior to the experiment THP-1 were treated with PMA (Phorbol 12-myristate 13-acetate) (10 µg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×106 cells/ml, and 100 µl was plated in a 96 well plate. Cells were incubated with compounds for 4 hours. Cell free supernatant was collected and the production of IL-1β was evaluated by ELISA.

Compounds were dissolved in dimethyl sulfoxide (DMSO) and added to the culture medium to achieve desired concentration (e.g. 100, 30, 10, 3, 1, 0.3 or 0.1 μM). A vehicle only control was run concurrently with each experiment. Final DMSO concentration was 1%. Compounds exhibit a dose-related increase of IL-1β production in PMA-differentiated THP-1 cells.

A number of embodiments of the invention have been described. Nevertheless, it will be understood that various modifications may be made without departing from the spirit and scope of the invention. Accordingly, other embodiments are within the scope of the following claims.

What is claimed is:

1. A compound selected from:

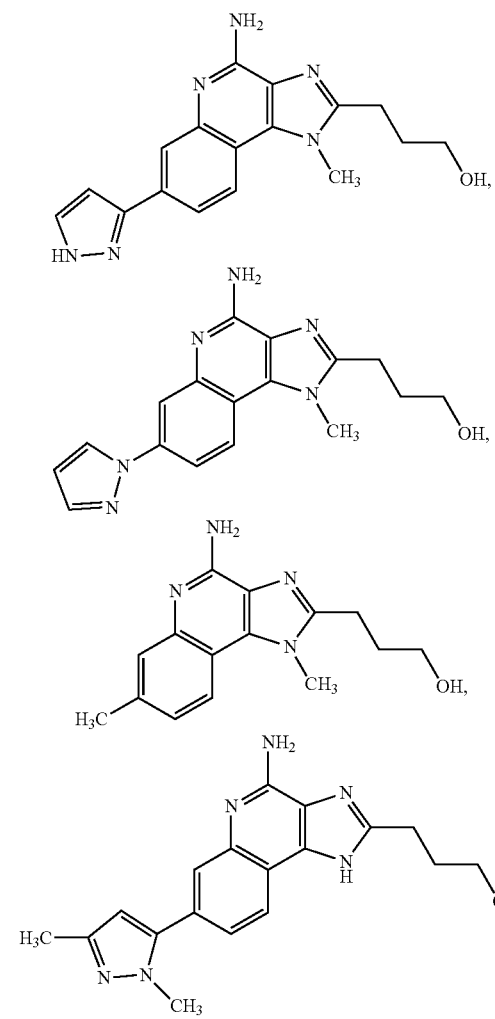

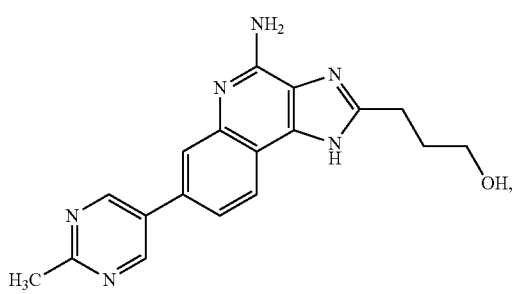

-continued

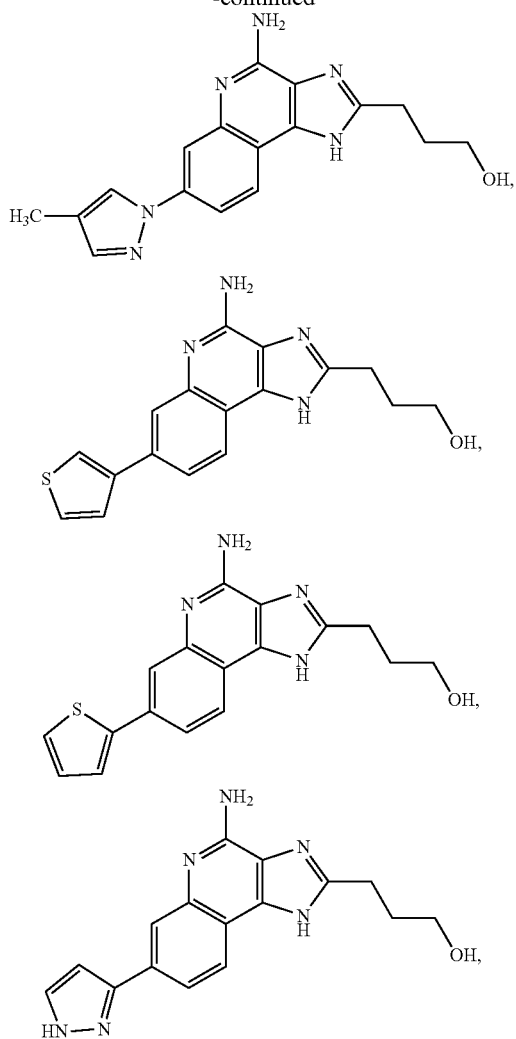

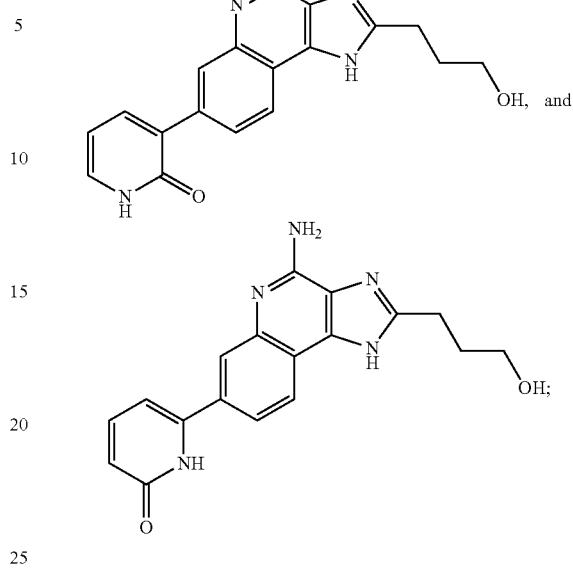

or a pharmaceutically acceptable salt thereof.

2. A pharmaceutical composition comprising a compound or salt as claimed in claim 1 and one or more pharmaceutically acceptable excipients.

3. A method of treating melanoma or basal cell carcinoma, comprising administering to a subject in need of such treatment an effective amount of a compound as claimed in claim 1.

4. The method of claim 3, wherein the compound is administered in combination with one or more additional cancer therapies.

5. The method of claim 4, wherein the one or more additional cancer therapies comprises surgery, radiotherapy, chemotherapy, toxin therapy, immunotherapy, cryotherapy or gene therapy, or a combination thereof.

* * * * *

UNITED STATES PATENT AND TRADEMARK OFFICE
CERTIFICATE OF CORRECTION

PATENT NO. : 10,556,903 B2
APPLICATION NO. : 16/093990
DATED : February 11, 2020
INVENTOR(S) : Gary D Glick et al.

Page 1 of 1

It is certified that error appears in the above-identified patent and that said Letters Patent is hereby corrected as shown below:

In the Claims

Column 137
Lines 38-45 (Approx.)

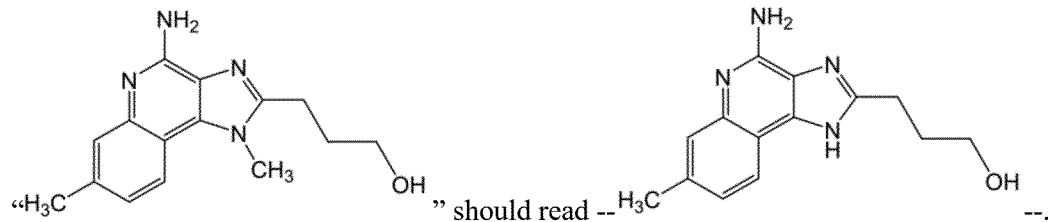

Signed and Sealed this
Twenty-third Day of June, 2020

Andrei Iancu
*Director of the United States Patent and Trademark Office*